United States Patent
Matsuo et al.

(10) Patent No.: US 11,098,364 B2
(45) Date of Patent: Aug. 24, 2021

(54) INHIBITING THE ONSET OF GOUT

(71) Applicant: The University Of Tokyo, Tokyo (JP)

(72) Inventors: Hirotaka Matsuo, Saitama (JP); Nariyoshi Shinomiya, Saitama (JP); Tappei Takada, Tokyo (JP)

(73) Assignee: Hirotaka Matsuo, Saitama (JP)

(*) Notice: Subject to any disclaimer, the term of this patent is extended or adjusted under 35 U.S.C. 154(b) by 112 days.

(21) Appl. No.: 16/405,812

(22) Filed: May 7, 2019

(65) Prior Publication Data

US 2019/0338361 A1 Nov. 7, 2019

Related U.S. Application Data

(63) Continuation of application No. 15/112,067, filed as application No. PCT/JP2015/051232 on Jan. 19, 2015, now abandoned.

(30) Foreign Application Priority Data

Jan. 17, 2014 (JP) ................................ 2014-006806
Sep. 5, 2014 (JP) ................................ 2014-181642

(51) Int. Cl.
| | | |
|---|---|---|
| C12Q 1/68 | (2018.01) | |
| C12P 19/34 | (2006.01) | |
| C12Q 1/6883 | (2018.01) | |
| A61K 38/00 | (2006.01) | |
| C07K 14/47 | (2006.01) | |
| G01N 33/68 | (2006.01) | |
| A61K 38/17 | (2006.01) | |
| A61K 38/44 | (2006.01) | |
| A61K 38/45 | (2006.01) | |
| A61K 38/53 | (2006.01) | |
| C12N 9/00 | (2006.01) | |
| A61K 48/00 | (2006.01) | |

(52) U.S. Cl.
CPC ............ *C12Q 1/6883* (2013.01); *A61K 38/00* (2013.01); *A61K 38/177* (2013.01); *A61K 38/1709* (2013.01); *A61K 38/44* (2013.01); *A61K 38/45* (2013.01); *A61K 38/53* (2013.01); *C07K 14/47* (2013.01); *G01N 33/6893* (2013.01); *A61K 48/00* (2013.01); *C12N 9/00* (2013.01); *C12Q 2600/156* (2013.01); *C12Y 102/01003* (2013.01); *C12Y 207/11025* (2013.01); *C12Y 603/04* (2013.01); *G01N 2800/107* (2013.01)

(58) Field of Classification Search
CPC ........ A61K 38/00; A61K 48/00; C12Q 1/6883; C12Q 2600/156
See application file for complete search history.

(56) References Cited

PUBLICATIONS

Bruno, B.J. et al. "Basics and recent advances in peptide and protein drug delivery" Ther Deliv. Nov. 2013; 4(11): 1443-1467 (Year: 2013).*
Sulem, P., Gudbjartsson, D., Walters, G. et al. Identification of low-frequency variants associated with gout and serum uric acid levels. Nat Genet 43, 1127-1130 (2011), including Supplementary Information. (Year: 2011).*
Reference SNP (refSNP) Cluster Report: rs2231142, from www.ncbi.nlm.nih.gov, pp. 1-6 printed on Jan. 21, 2020 (Year: 2020).*
Reference SNP (refSNP) Cluster Report: rs7903456, from www.ncbi.nlm.nih.gov, pp. 1-4 printed on Jan. 21, 2020 (Year: 2020).*

* cited by examiner

*Primary Examiner* — Stephen T Kapushoc
(74) *Attorney, Agent, or Firm* — Defillo & Associates, Inc.; Evelyn A. Defillo

(57) ABSTRACT

To specify a molecule associated with the onset of gout so as to provide a method for evaluating a diathesis of uric acid-related diseases and a diathesis of inflammation-related diseases, an evaluation kit for carrying out the method, an inspection object, and a drug, on the basis of the molecule specified above, for contributing to the early treatment and prevention of the uric acid-related diseases and inflammation-related diseases. The molecule includes any one protein and cDNA of CNIH2-PACS1, ALDH2, MYL2-CUX2, GCKR, MAP3K11, NPT4, ABCG2, HIST1H2BF/HIST1H4E, HIST1H2BE/HIST1H4D and FAM35A, or proteins of combination thereof with GLUT9, NPT1, URAT1, or NXRN2, and is capable of selectively inducing gout. A molecule includes protein and cDNA of an ABCG2 variant and is capable of selectively and ATP-dependently decreasing urate excretion.

2 Claims, 49 Drawing Sheets

Specification includes a Sequence Listing.

| | | | | | Freq. | | GWAS[d] | | Freq. | | Replication study[e] | | Meta-analysis[f] | |
|---|---|---|---|---|---|---|---|---|---|---|---|---|---|---|
| SNP[a] | Chr. | Position (bp)[b] | Gene | A1/A2[c] | Cases | Controls | OR (95% CI) | P value | Cases | Controls | OR (95% CI) | P value | OR (95% CI) | P value |
| rs2728125 | 4 | 89001893 | ABCG2 | C/T | 0.40 | 0.25 | 2.05 (1.80-2.34) | $1.5 \times 10^{-27}$ | 0.40 | 0.24 | 2.03 (1.79-2.30) | $8.3 \times 10^{-29}$ | 2.04 (1.86-2.23) | $7.2 \times 10^{-54}$ |
| rs3775948 | 4 | 9995182 | SLC2A9 | G/C | 0.68 | 0.56 | 1.64 (1.45-1.86) | $6.7 \times 10^{-15}$ | 0.67 | 0.56 | 1.57 (1.40-1.77) | $7.6 \times 10^{-14}$ | 1.61 (1.47-1.75) | $5.5 \times 10^{-27}$ |
| rs2188380 | 12 | 111386127 | MYL2-CUX2 | T/C | 0.85 | 0.76 | 1.78 (1.52-2.08) | $5.7 \times 10^{-15}$ | 0.86 | 0.78 | 1.73 (1.48-2.02) | $2.0 \times 10^{-12}$ | 1.75 (1.57-1.96) | $1.6 \times 10^{-23}$ |
| rs1260326 | 2 | 27730940 | GCKR | T/C | 0.62 | 0.54 | 1.39 (1.23-1.57) | $1.2 \times 10^{-7}$ | 0.61 | 0.55 | 1.32 (1.18-1.49) | $2.8 \times 10^{-6}$ | 1.36 (1.25-1.48) | $1.9 \times 10^{-12}$ |
| rs4073582 | 11 | 66050712 | CNIH-2 | G/A | 0.95 | 0.91 | 1.78 (1.39-2.29) | $5.3 \times 10^{-6}$ | 0.94 | 0.91 | 1.55 (1.23-1.96) | $1.6 \times 10^{-4}$ | 1.66 (1.40-1.96) | $6.4 \times 10^{-9}$ |
| rs10791821[*] | 11 | 65368323 | MAP3K11 | G/A | 0.94 | 0.90 | 1.75 (1.38-2.22) | $2.8 \times 10^{-6}$ | 0.94 | 0.92 | 1.41 (1.12-1.77) | $3.4 \times 10^{-3}$ | 1.57 (1.33-1.85) | $1.0 \times 10^{-7}$ |

Chr., chromosome; Freq., Frequency of A1; OR, odds ratio; CI, confidence interval.

[a]dbSNP rs number. A suggestive SNP is marked with "*".

[b]SNP positions are based on NCBI human genome reference sequence Build 37.4.

[c]A1 is risk-associated allele and A2 is non-risk-associated allele.

[d]945 gout cases and 1,213 controls.

[e]1,048 gout cases and 1,334 controls.

[f]Meta-analyses of the combined GWAS and replication samples (1,993 gout cases and 2,547 controls).

FIGURE 10

| SNP[a] | Gene | ROL type v.s. controls[b] | | RUE type v.s. controls[b] | | Case-subtype heterogeneity test | |
|---|---|---|---|---|---|---|---|
| | | OR (95% CI) | P value | OR (95% CI) | P value | OR (95% CI) | P value[c] |
| rs3775948 | *SLC2A9* | 1.38 (1.14-1.68) | $1.0 \times 10^{-3}$ | 1.94 (1.63-2.31) | $1.0 \times 10^{-13}$ | 0.66 (0.53-0.83) | $2.7 \times 10^{-4}$ |
| rs2188380 | *MYL2-CUX2* | 1.45 (1.11-1.89) | $6.5 \times 10^{-3}$ | 1.47 (1.16-1.86) | $1.2 \times 10^{-3}$ | 0.92 (0.68-1.25) | 0.60 |
| rs1260326 | *GCKR* | 1.25 (1.04-1.50) | 0.016 | 1.35 (1.15-1.58) | $3.0 \times 10^{-4}$ | 0.94 (0.77-1.14) | 0.51 |
| rs4073582 | *CNIH-2* | 1.96 (1.30-2.95) | $1.2 \times 10^{-3}$ | 1.51 (1.09-2.08) | 0.013 | 1.26 (0.80-1.99) | 0.32 |
| rs10791821 | *MAP3K11* | 1.37 (0.96-1.96) | 0.084 | 1.79 (1.26-2.54) | $1.2 \times 10^{-3}$ | 0.79 (0.51-1.23) | 0.30 |
| rs72552713 | *ABCG2* | 4.35 (2.82-6.72) | $3.0 \times 10^{-11}$ | 1.28 (0.78-2.12) | 0.32 | 2.90 (1.77-4.75) | $2.4 \times 10^{-5}$ |
| rs2231142 | *ABCG2* | 3.37 (2.76-4.12) | $2.8 \times 10^{-32}$ | 1.88 (1.58-2.24) | $2.5 \times 10^{-12}$ | 1.76 (1.43-2.17) | $1.0 \times 10^{-7}$ |

ROL, renal overload; RUE, renal underexcretion; OR, odds ratio; CI, confidence interval.

[a] dbSNP rs number.

[b] We performed multivariate logistic regression analyses, in which all the seven SNPs, alcohol drinking and BMI were included in the model. 1,613 gout patients and 1,334 controls with genotypes for rs72552713 and rs2231142 of *ABCG2*, which were not on the illumina OmniExpress platform, were used. 375 and 509 gout patients were grouped into ROL type and RUE type, respectively.

[c] P values smaller than 0.05 are shown in bold letters.

FIGURE 12

| SNP A | SNP A | | rs671 | |
|---|---|---|---|---|
| | P value† | OR (95% CI) | P value‡ | OR (95% CI) |
| rs7978484 | 0.390 | 0.94 (0.74-1.19) | 2.6 × 10⁻¹⁶ | 0.57 (0.46-0.70) |
| rs16940688 | 0.054 | 0.93 (0.79-1.10) | 1.6 × 10⁻¹⁸ | 0.54 (0.47-0.63) |
| rs2071629 | 0.226 | 0.80 (0.63-1.00) | 7.8 × 10⁻²⁰ | 0.57 (0.49-0.67) |
| rs2188380 | 0.593 | 0.89 (0.73-1.08) | 2.1 × 10⁻¹⁷ | 0.56 (0.47-0.67) |
| rs11065783 | 0.195 | 1.11 (0.95-1.31) | 6.8 × 10⁻¹⁶ | 0.48 (0.41-0.56) |
| rs3809297 | 0.213 | 0.85 (0.66-1.10) | 3.1 × 10⁻⁵ | 0.59 (0.46-0.76) |
| rs4766566 | 0.032 | 0.82 (0.69-0.98) | 3.2 × 10⁻⁸ | 0.61 (0.50-0.75) |
| rs2555004 | 0.353 | 1.07 (0.93-1.24) | 9.4 × 10⁻¹⁹ | 0.52 (0.45-0.60) |

Result of analysis of only rs671 (without adjustment) showed P=1.7 × 10⁻¹⁸ and or = 53 (0.45-0.61)

P values smaller than 6.3 × 10⁻³ (adjusting for 8 tests with Bonferroni correction) are shown in bold letters. OR = odds ratio; CI = confidence interval.

†P values of each of the 8 SNPs (SNP A) adjusted by rs671.

‡P values of rs671 adjusted by SNP A.

FIG. 15

|  | Univariate | | Multivariate[†] | |
| --- | --- | --- | --- | --- |
|  | P value | OR (95% CI) | P value | OR (95% CI) |
| rs671 of *ALDH2* | $1.8 \times 10^{-18}$ | 0.53 (0.46-0.61) | $1.1 \times 10^{-9}$ | 0.62 (0.53-0.73) |
| Alcohol drinking | $2.7 \times 10^{-14}$ | 2.44 (1.94-3.07) | $2.2 \times 10^{-4}$ | 1.65 (1.26-2.15) |

[*]OR = odds ratio; CI = confidence interval.
[†]We analyzed 1,048 cases and 1,323 controls whose genotype data for rs671 and alcohol drinking behavior were available.

FIGURE 16

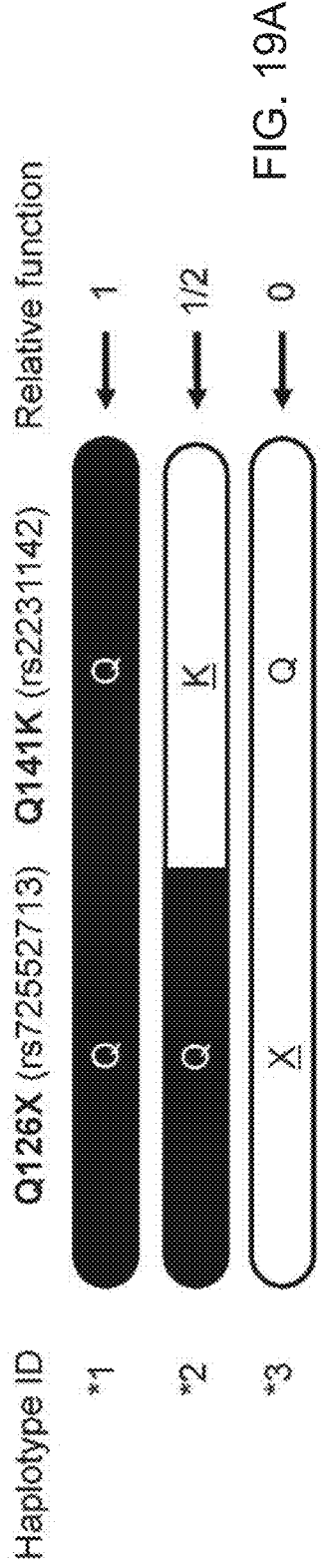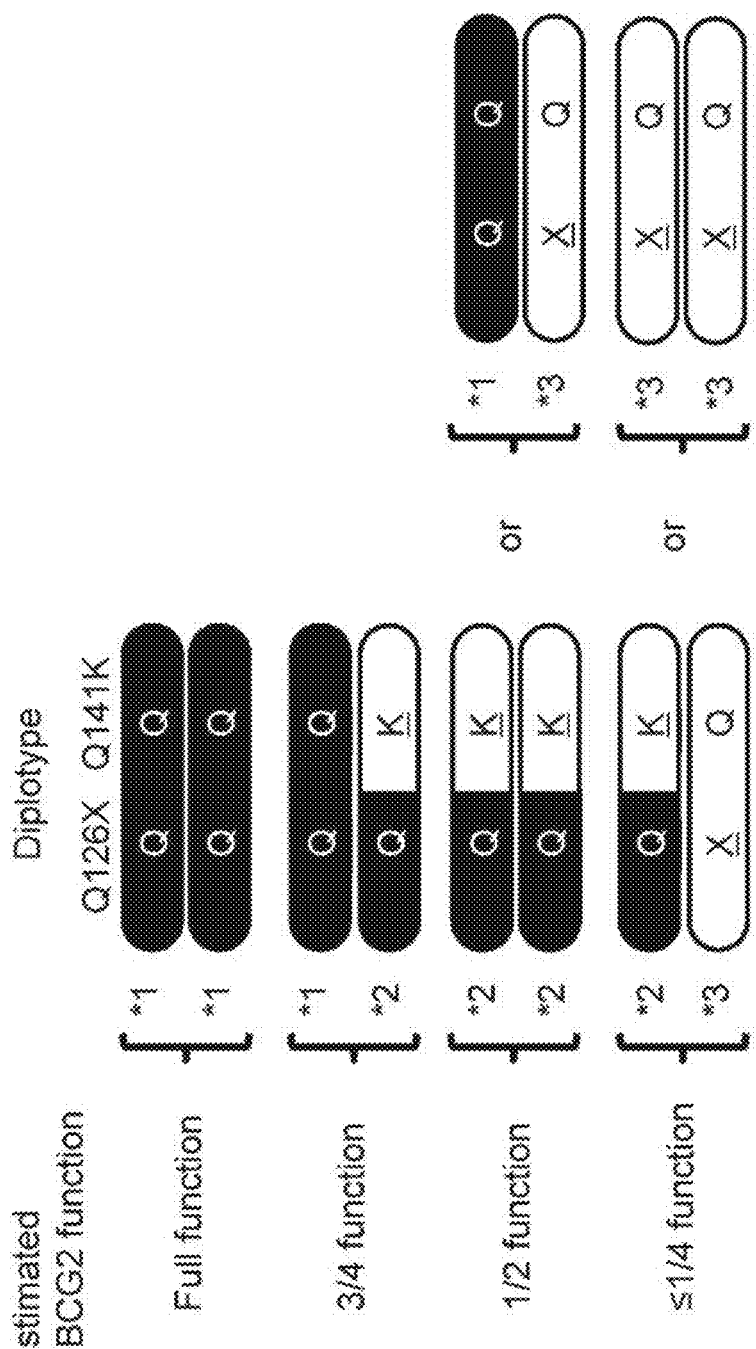
FIG. 19A
FIG. 19B

| Function of ABCG2 | Total | | Male | | Female | |
|---|---|---|---|---|---|---|
| | (N) | (%) | (N) | (%) | (N) | (%) |
| Full function | 2338 | 46.7 | 1592 | 46.8 | 746 | 46.5 |
| 3/4 function (mild dysfunction) | 1971 | 39.4 | 1332 | 39.2 | 639 | 39.8 |
| 1/2 function (moderate dysfunction) | 619 | 12.4 | 424 | 12.5 | 195 | 12.2 |
| ≤1/4 function (severe dysfunction) | 77 | 1.5 | 53 | 1.6 | 24 | 1.5 |
| total | 5005 | 100.0 | 3401 | 100.0 | 1604 | 100.0 |

FIG. 21

| Risk factors | $\beta^c$ (regression coefficient) | 95% CI | $P$ value | $\beta_{ABCG2}/\beta$ (ratio of regression coefficients) |
|---|---|---|---|---|
| ABCG2 function [a] | 0.193 | 0.150 – 0.235 | $5.99 \times 10^{-19}$ | 1.00 |
| Sex [b] | 1.46 | 1.38 – 1.53 | $2.34 \times 10^{-296}$ | 0.13 |
| Age, years | $4.0 \times 10^{-3}$ | $4.5 \times 10^{-4}$ – $7.6 \times 10^{-3}$ | 0.028 | 47.6 |
| BMI, kg/m² | 0.098 | 0.087 – 0.108 | $1.29 \times 10^{-68}$ | 1.97 |
| Alcohol consumption, g/week of pure alcohol | $3.5 \times 10^{-4}$ | $1.7 \times 10^{-4}$ – $5.3 \times 10^{-4}$ | $1.77 \times 10^{-4}$ | 552.1 |

Abbreviation: BMI, body mass index (calculated as weight in kilograms divided by height in meters squared).

[a] Calculation for ABCG2 function was conducted for full function as 1, 3/4 function (mild dysfunction) as 2, 1/2 function (moderate dysfunction) as 3, and ≤1/4 function (severe dysfunction) as 4.

[b] Calculation for sex was conducted for female as 1 and male as 2.

[c] "β" indicates the increase of SUA (mg/dl) per unit of each risk factor. The ratio of regression coefficients ($\beta_{ABCG2}/\beta$) was calculated from the β of ABCG2 function divided by that of each risk factor, showing an effect equivalent to a 25% decrease in ABCG2 function in terms of ability to increase SUA levels.

FIGURE 23

FIG. 27 (SEQ ID NO:1)

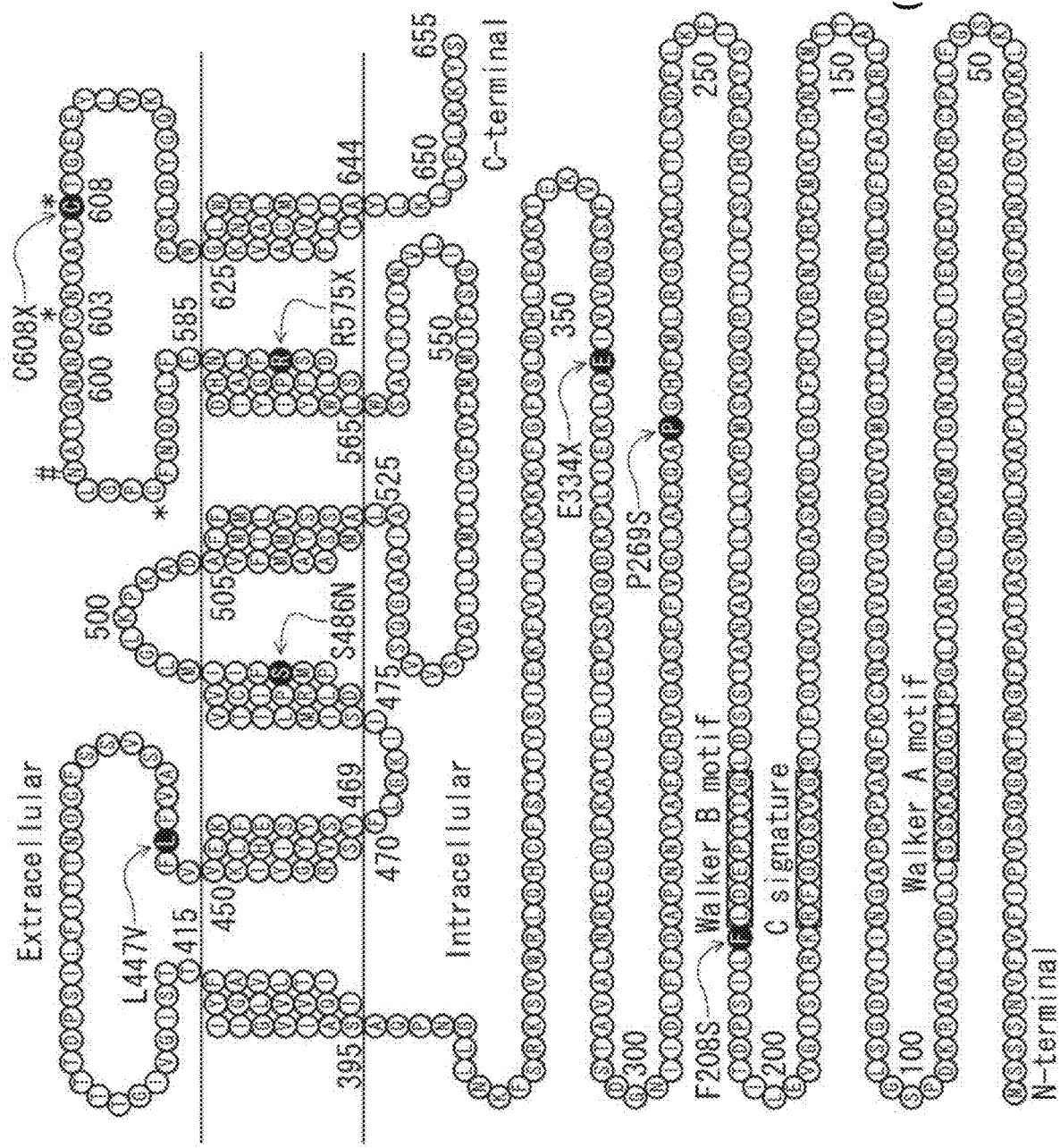
FIG. 30 (SEQ ID NO:1)

| | AMINO ACID VARIATION | INTRACELLULAR LOCALIZATION | WESTERN BLOTTING | TRANSPORT ACTIVITY OF EACH SUBSTRATE (RELATIVE VALUE WHEN WILD-TYPE TRANSPORT ACTIVITY IS DEFINED AS 1) | | | | |
|---|---|---|---|---|---|---|---|---|
| | | | | Urate | MTX | DHFAS[c] | PAH[c] | $E_1S^c$ |
| 1 | V12M | APICAL MEMBRANE[a,b] | NORMAL[a,d] | 7[f] | 1[a,c] | 1 | 1 | 1 |
| 2 | Q126X | | EXPRESSION IS NOT OBSERVED | 0[a] | 0[c] | | | |
| 3 | Q141K | APICAL MEMBRANE[a,b] | ABOUT 50%[a,b,d] | 1/2 | 1/2[a], 1[c] | 1/2 | 1/2 | 1/2 |
| 4 | F208S | EXPRESSION IS NOT OBSERVED | EXPRESSION IS NOT OBSERVED | 0 | 0[c] | | | |
| 5 | G268R | | | 0[a] | | | | |
| 6 | P269S | APICAL MEMBRANE | NORMAL | 1 | 1[a] | 1 | 1 | 1 |
| 7 | E334X | INTRACELLULAR SMALL MOLECULAR WEIGHT | | 0[a] | 0[c] | | | |
| 8 | S441N | INTRACELLULAR[a,b] | SHARP DECREASE[a,b] | 0[a] | 0[c] | | | |
| 9 | L447V | APICAL MEMBRANE | ABOUT 70% | 0 | | | | |
| 10 | S486N | APICAL MEMBRANE | ABOUT 60% | 0 | | | | |
| 11 | F506SfsX4 | | | 0[d] | | | | |
| 12 | R575X | INTRACELLULAR SMALL MOLECULAR WEIGHT | | 0 | | | | |
| 13 | C608X | APICAL MEMBRANE | SHARP DECREASE | 1/5 | | | | |

FIG. 35

|  | Patients | | | Controls | | | p | OR | 95% CI | | |
|---|---|---|---|---|---|---|---|---|---|---|---|
|  | T | C | MAF | T | C | MAF |  |  |  |  |  |
| All gout | 953 | 137 | 0.126 | 1868 | 318 | 0.145 | 0.123 | 0.84 | 0.68 | - | 1.05 |
| Reciprocal |  |  |  |  |  |  |  | 1.18 | 0.96 | - | 1.47 |
| RUE gout, $FE_{UA}$ < 5.5% | 486 | 60 | 0.110 | 1868 | 318 | 0.145 | 0.031 | 0.73 | 0.54 | - | 0.97 |
| Reciprocal |  |  |  |  |  |  |  | 1.38 | 1.03 | - | 1.85 |
| Non-RUE gout, $FE_{UA}$ ≥ 5.5% | 323 | 57 | 0.150 | 1868 | 318 | 0.145 | 0.577 | 1.04 | 0.76 | - | 1.41 |
| Reciprocal |  |  |  |  |  |  |  | 0.96 | 0.71 | - | 1.31 |

\* C is the minor allele. MAF = minor allele frequency; OR = odds ratio;
CI = confidence interval; RUE = renal underexcretion; $FE_{UA}$ = urate clearance:creatinine ratio.

FIGURE 36

RESIDUES 486-490
OF (SEQ ID NO:1),
SUBSTITUTION AT
RESIDUE 489

RESIDUES 618-623
OF (SEQ ID NO:1),
SUBSTITUTION AT
RESIDUE 620

|  | Case | Control | P-value[a] | OR (95% CI) | Reciprocal OR (95% CI) |
|---|---|---|---|---|---|
| Wild type | 2208 | 1301 | Ref | | |
| Mutation[b] | 1 | 87 | $6.3 \times 10^{-32}$ | 0.0068 (0.00094–0.049) | 147.7 (20.5–1061.3) |

OR, odds ratio; CI, confidence interval; Ref, reference.
[a]Chi-square test.
[b]The mutation means R90H or W258X in URAT1.

FIGURE 41A

|  | P-value[a] | OR (95% CI) | Reciprocal OR (95% CI) |
|---|---|---|---|
| URAT1 variant[b] | $6.9 \times 10^{-7}$ | 0.0065 (0.00090–0.047) | 153.6 (21.3–1109.2) |
| Q126X in ABCG2 | $2.9 \times 10^{-11}$ | 2.73 (2.03–3.67) | |
| Q141K in ABCG2 | $7.8 \times 10^{-52}$ | 2.34 (2.10–2.61) | |

OR, odds ratio; CI, confidence interval.
[a]We analyzed 2,209 cases and 1,388 controls whose all of the genotype data for URAT1 and ABCG2 were available.
[b]URAT1 variant means R90H or W258X.

FIGURE 41B

| SNP | Chromosome | Gene | P-value |
|---|---|---|---|
| rs2285340 | 11 | NRXN2-SLC22A12/URAT1 | $1.73 \times 10^{-11}$ |
| rs1165176 | 6 | SLC17A1/NPT1 | $1.78 \times 10^{-9}$ |
| rs11758351 | 6 | HIST1H2BF/HIST1H4E | $2.09 \times 10^{-9}$ |
| rs4496782 | 6 | HIST1H2BE/HIST1H4D | $4.32 \times 10^{-9}$ |

FIG. 42

| ABCG2_function | Urinary coproporphyrin | | |
|---|---|---|---|
| | average | SE | P-value |
| 50% or less | 40.1 | 6.6 | |
| 75% | 59.1 | 3.7 | |
| 100% | 55.2 | 3.3 | 0.040 |

FIG. 43

| estimated ABCG2 function | stroke | | control | | p-value | OR |
|---|---|---|---|---|---|---|
| | N | % | N | % | | |
| 100% | 27 | 36.5 | 439 | 50.8 | -- | reference |
| ≤75% | 47 | 63.5 | 426 | 49.3 | 0.018 | 1.79 |
| total | 74 | 100 | 865 | 100 | | |

FIG. 44

| estimated ABCG2 function | Male | | Female | |
| --- | --- | --- | --- | --- |
| | N | SUA | N | SUA |
| 100% | 18 | 5.24 ± 0.34 | 11 | 3.28 ± 0.27 |
| ≤75% | 9 | 5.54 ± 0.21 | 18 | 3.85 ± 0.18 |
| total | 27 | 5.34 ± 0.24 | 29 | 3.63 ± 0.16 |

SUA=SERUM URIC ACID LEVEL(mg/dl)

FIG. 45

|  | SUA BEFORE TREATMENT | | |
|---|---|---|---|
|  | N | AVERAGE±SE | p value |
| ALL CASES (30 MALES, 28 FEMALES) | 58 | 8.96±0.48 | 0.016 |
| ONLY MILD DEHYDRATION (22 MALES, 23 FEMALES) | 45 | 8.06±0.45 | 0.029 |

FIG. 46

| ABCG2 FUNCTION | NUMBER OF CASES | FREQUENCY (%) | INTRODUCTION AGE (YEAR) | p-value |
|---|---|---|---|---|
| 100% | 56 | 40.3% | 59.4±1.99 | |
| 75% | 63 | 45.3% | 57.7±1.79 | |
| 50% OR LESS | 20 | 14.4% | 50.8±3.44 | |
| total | 139 | 100.0% | 57.4±1.26 | 0.044 |

FIG. 47A

| ABCG2 FUNCTION | NUMBER OF CASES | FREQUENCY (%) | SERUM URIC ACID LEVEL | p-value |
|---|---|---|---|---|
| 100% | 51 | 48.1% | 7.1±0.14 | |
| 75% | 46 | 43.4% | 7.9±0.15 | |
| 50% OR LESS | 9 | 8.5% | 8.5±0.89 | |
| total | 106 | 100.0% | 7.6±0.12 | $8.9 \times 10^{-6}$ |

FIG. 47B

SEQUENCE LISTING

```
<160> NUMBER OF SEQ ID NOS: 1

<210> SEQ ID NO 1
<211> LENGTH: 655
<212> TYPE: PRT
<213> ORGANISM: Homo sapiens
```

<400> SEQUENCE: 1

```
Met Ser Ser Ser Asn Val Glu Val Phe Ile Pro Val Ser Gln Gly Asn
  1               5                  10                  15

Thr Asn Gly Phe Pro Ala Thr Ala Ser Asn Asp Leu Lys Ala Phe Thr
             20                  25                  30

Glu Gly Ala Val Leu Ser Phe His Asn Ile Cys Tyr Arg Val Lys Leu
         35                  40                  45

Lys Ser Gly Phe Leu Pro Cys Arg Lys Pro Val Lys Glu Ile Leu
 50                  55                  60

Ser Asn Ile Asn Gly Ile Met Lys Pro Gly Leu Asn Ala Ile Leu Gly
 65                  70                  75                  80

Pro Thr Gly Gly Gly Lys Ser Ser Leu Leu Asp Val Leu Ala Ala Arg
                 85                  90                  95

Lys Asp Pro Ser Gly Leu Ser Gly Asp Val Leu Ile Asn Gly Ala Pro
             100                 105                 110

Arg Pro Ala Asn Phe Lys Cys Asn Ser Gly Tyr Val Val Gln Asp Asp
             115                 120                 125

Val Val Met Gly Thr Leu Thr Val Arg Glu Asn Leu Gln Phe Ser Ala
 130                 135                 140

Ala Leu Arg Leu Ala Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                 165                 170                 175

Lys Val Gly Thr Gln Phe Ile Arg Gly Val Ser Gly Gly Glu Arg Lys
             180                 185                 190

Arg Thr Ser Ile Gly Met Glu Leu Ile Thr Asp Pro Ser Ile Leu Phe
             195                 200                 205

Leu Asp Glu Pro Thr Thr Gly Leu Asp Ser Ser Thr Ala Asn Ala Val
 210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                 245                 250                 255

Thr Leu Leu Ala Ser Gly Arg Leu Met Phe His Gly Pro Ala Gln Glu
             260                 265                 270

Ala Leu Gly Tyr Phe Glu Ser Ala Gly Tyr His Cys Glu Ala Tyr Asn
             275                 280                 285

Asn Pro Ala Asp Phe Phe Leu Asp Ile Ile Asn Gly Asp Ser Thr Ala
 290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                 325                 330                 335

Val Asn Ser Ser Phe Tyr Lys Glu Thr Lys Ala Glu Leu His Gln Leu
             340                 345                 350

Ser Gly Gly Glu Lys Lys Lys Ile Thr Val Phe Lys Glu Ile Ser
             355                 360                 365

Tyr Thr Thr Ser Phe Cys His Gln Leu Arg Trp Val Ser Lys Arg Ser
             370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
```

-continued

```
                405                 410                 415
Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
            435                 440                 445

Val Val Glu Lys Lys Leu Phe Ile His Glu Tyr Ile Ser Gly Tyr Tyr
    450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
            485                 490                 495

Leu Gly Leu Lys Pro Lys Ala Asp Ala Phe Phe Val Met Met Phe Thr
            500                 505                 510

Leu Met Met Val Ala Tyr Ser Ala Ser Ser Met Ala Leu Ala Ile Ala
            515                 520                 525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
            565                 570                 575

Gly Phe Thr Ala Leu Gln His Asn Glu Phe Leu Gly Gln Asn Phe Cys
            580                 585                 590

Pro Gly Leu Asn Ala Thr Gly Asn Asn Pro Cys Asn Tyr Ala Thr Cys
            595                 600                 605

Thr Gly Glu Glu Tyr Leu Val Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
            645                 650                 655
```

INHIBITING THE ONSET OF GOUT

CROSS-REFERENCE TO RELATED APPLICATIONS

This application is a continuation of U.S. application Ser. No. 15/112,067, filed Jul. 15, 2016, which is a national stage entry from International Application No. PCT/JP2015/051232, filed Jan. 19, 2015, and claims the benefit of prior application Nos. JP2014-006806, Jan. 17, 2014, and JP2014-181642, filed Sep. 5, 2014, each application of which is hereby incorporated herein by reference in its entirety.

SEQUENCE LISTING

This application incorporates by reference in its entirety the last-filed sequence listing submitted in ASCII format via EFS-Web in U.S. application Ser. No. 15/112,067, filed Jul. 15, 2016. Said ASCII copy, was created May 7, 2019, as modified Sep. 15, 2016, and is named TSUBP003US01_SL_9-15-2016.txt and is 6,153 bytes in size.

TECHNICAL FIELD

The present invention relates to a molecule associated with the onset of gout, as well as a method for evaluating a uric acid-related disease diathesis and an inflammation-related disease diathesis, and an evaluation kit for carrying out the method, and also an inspection object and a drug relating to the method and kit.

BACKGROUND

Recently, gout patients have increased and the onset age has become younger. Gout is a disease caused by deposition of monosodium urate crystals in tissue, and often has the onset as a result of inflammation of the joint. Furthermore, gout is frequently found in hyperuricemia patients, and has long been known to have heritable components.

Gout is often complicated with hypertension, obesity, diabetes, coronary artery diseases, cerebrovascular diseases, kidney diseases, and the like. Furthermore, inflammation-related diseases include rheumatoid arthritis, infertility, and the like. Thus, early treatment and prevention of these diseases are needed.

The present inventors have demonstrated, using function-based genetic analysis, that loss-of-function type mutations in two types of urate transporter genes, i.e., urate transporter gene 1 (URAT1/SLC22A12) and glucose transporter 9 (GLUT9/SLC2A9), cause renal hypouricemia (MIM220150 and MIM612076, respectively) (Non-Patent Literatures 1 and 2). These findings, together with their renal expression patterns, also show that URAT1 and GLUT9 mediate renal urate reabsorption in human.

However, other urate transporters have not been identified by such analyses, and urate transporters including patho-genenic variants that increase the serum uric acid (SUA) level remain unidentified.

The prior art relating to a urate transporter includes Patent Literature 1, and the prior arts relating to ABCG2 as a transporter include Patent Literatures 2 to 4. However, the prior arts disclose the ABCG2 as a transporter of a drug, but not disclose its involvement in urate transport.

Furthermore, it is generally known that the hyperuricemia may be a risk of gout but does not necessarily cause gout, for example, it is reported that the onset rate of gout in 5 years is just about 20% even in patients having severe hyperuricemia having a serum uric acid level of 9 mg/dL or more. However, it has not been clarified what types of hyperuricemia patients develop gout, and what types of hyperuricemia patients do not develop gout.

Therefore, in conventional medical treatment, patients having not less than the predetermined level of hyperuricemia have been prescribed with a urate lowering drug, although most of them have low gout risk. On the other hand, some cases develop gout although the serum uric acid level is not so high, and physical and economic burden of the gout patients have been large.

In Patent Literature 5, the present inventors have disclosed that ABCG2 (ATP-binding cassette G2) responsible for exporting various drugs and endogenous compounds has had transported uric acid at high affinity. Furthermore, the present inventors have demonstrated for the first time that Q141K variation in the ABCG2 gene, which is frequently found in hyperuricemia or gout case, decrease the transport activity to about half level; the transport activity is lost in some variations including Q126X; in inspection of an influence on uric acid levels of a Q141K polymorphism in healthy subjects, the serum uric acid level is increased according to the holding number of Q141K variations; and ABCG2 controls urate excretion in the kidney, liver, and small intestine in human. That is to say, the present inventors have found that the ABCG2 gene is a major causative gene of gout.

This finding is a result supporting an established theory that gout is a disease including unknown familial and genetic factors, and is the first discovery in the world as an example showing that common variants are pathogenic variants and cause a common disease (gout).

Thus, providing medical care such as preventive medicine with respect to cases of hyperuricemia and gout according to individual differences is becoming possible. However, since about 20% of cases does not have variations in Q126X and Q141K of ABCG2, development of more detailed genetic analysis technology has been required. Furthermore, when variations are found, it is desirable that specific measures, for example, a target values for diet be set, but they have not been able to be made by conventional technology.

CITATION LIST

Patent Literature

Patent Literature 1: JP-A-2003-93067, "Renal and placental urate transporters and their genes".
Patent Literature 2: JP-A-2007-60967, "Detection method of gene polymorphisms and screening method of drugs".
Patent Literature 3: JP-A-2004-16042, "Mutated polynucleotides and nucleic acid molecules which can be used for genetic diagnosis of abnormality in drug absorption involving ABCG2 protein".
Patent Literature 4: JP-A-2005-529618, "Prediction method of drug transport capability by ABCG2 polymorphism".
Non-Patent Literatures
Patent Literature 5: Japanese Patent Application No. 2009-148106 "Urate Transporter, as well as Method and Kit for Evaluating Urate Transport-Related Disease Factor and Inflammation-Related Disease Factor, and Sample and Drug"

Non-Patent Literature

Non-Patent Literature 1: Enomoto A, Kimura H, Chairoungdua A, et al. Molecular identification of a renal urate anion exchanger that regulates blood urate levels. Nature 2002; 417: 447-52.

Non-Patent Literature 2: Matsuo H, Chiba T, Nagamori S, et al. Mutations in glucose transporter 9 gene SLC2A9 cause renal hypouricemia. Am J Hum Genet 2008; 83: 744-51.

Non-Patent Literature 3: Kondo C, Suzuki H, Itoda M, et al. Functional analysis of SNPs variants of BCRP/ABCG2. Pharm Res 2004; 21: 1895-903.

Non-Patent Literature 4: Tin, A. et al. Genome-wide association study for serum urate concentrations and gout among African Americans identifies genomic risk loci and a novel URAT1 loss-of-function allele. Human Molecular Genetics 20, 4056-68 (2011).

Non-Patent Literature 5: Sulem, P. et al. Identification of low-frequency variants associated with gout and serum uric acid levels. Nature Genetics 43, 1127-30 (2011).

Non-Patent Literature 6: Kottgen, A. et al. Genome-wide association analyses identify 18 new loci associated with serum urate concentrations. Nature Genetics 45, 145-54 (2013).

Non-Patent Literature 7: Ichida, K. et al. Decreased extrarenal urate excretion is a common cause of hyperuricemia. Nature communications 3, 764 (2012).

Non-Patent Literature 8: Matsuo, H. et al. Common defects of ABCG2, a high-capacity urate exporter, cause gout: a function-based genetic analysis in a Japanese population. Sci Transl Med 1, 5ra11 (2009).

Non-Patent Literature 9: Matsuo, H. et al. Common dysfunctional variants in ABCG2 are a major cause of early-onset gout. Scientific Reports 3, 2014 (2013).

Non-Patent Literature 10: Hirotaka Matsuo, Kimiyoshi Ichida, Tappei Takada, Akiyoshi Nakayama, Nariyoshi Shinomiya, Urate transporter as predominant factor of uric acid regulation. Saibou Kougaku, 31 (5), 553-557, 2012.

Non-Patent Literature 11: K. Maedaand Y. Sugiyama. Impact of genetic polymorphisms of transporters on the pharmacokinetic, pharmacodynamic and toxicological properties of anionic drugs. Drug Metab Pharmacokinet. 23: 223-235 (2008).

Non-Patent Literature 12: C. Kondo, H. Suzuki, M. Itoda, S. Ozawa, J. Sawada, D. Kobayashi, I. Ieiri, K. Mine, K. Ohtsubo, and Y. Sugiyama. Functional analysis of SNPs variants of BCRP/ABCG2. Pharm Res. 21: 1895-1903 (2004).

Non-Patent Literature 13: S. Koshiba, R. An, H. Saito, K. Wakabayashi, A. Tamura, and T. Ishikawa. Human ABC transporters ABCG2 (BCRP) and ABCG4. Xenobiotica. 38: 863-888 (2008).

Non-Patent Literature 14: A. Tamura, K. Wakabayashi, Y. Onishi, M. Takeda, Y. Ikegami, S. Sawada, M. Tsuji, Y. Matsuda, and T. Ishikawa. Re-evaluation and functional classification of non-synonymous single nucleotide polymorphisms of the human ATP-binding cassette transporter ABCG2. Cancer Sci. 98: 231-239 (2007).

Non-Patent Literature 15: Rohan S. Wijesurendra, Barbara Casadei. Atrial Fibrillation: Effects Beyond the Atrium? Cardiovascular Research Advance Access published Jan. 12, 2015.

Non-Patent Literature 16: Muhammad A. Balouch, Matthew J. Kolek, Dawood Darbar. Improved understanding of the pathophysiology of atrial fibrillations through the lens of discretes pathological pathways. Balouch et al. Global Cardiology Science and Practice 2014: 5.

SUMMARY OF THE INVENTION

Problems to be Solved by the Invention

Accordingly, the object of the present invention is to provide a method for evaluating a uric acid-related disease diathesis and an inflammation-related disease diathesis and to provide an evaluation kit for carrying out the method, and an inspection object and a drug relating to the method and the kit so that a high-capacity urate transporter is identified so as to contribute to early treatment and prevention of uric acid-related diseases and inflammation-related diseases on the basis of the identified transporter.

Solution to Problem

A molecule associated with the onset of gout of the present invention is a molecule which is associated with the onset of gout, and is characterized by including any one protein or cDNA of CNIH2-PACS1, ALDH2, MYL2-CUX2, GCKR, MAP3K11, NPT4, ABCG2, HIST1H2BF/HIST1H4E, HIST1H2BE/HIST1H4D, and FAM35A, or a combination thereof with any one protein or cDNA of GLUT9, NPT1, URAT1, and NXRN2, and being capable of relating to the onset of gout; or including protein or cDNA of an ABCG2 variant, and being capable of selectively and ATP-dependently decreasing excretion of urate.

A method for evaluating a uric acid-related disease diathesis and an inflammation-related disease diathesis of the present invention includes evaluating whether or not a subject has a diathesis capable of inducing urate regulation failure, or a state or a uric acid-related disease attributable to the failure. The evaluating includes a step of detecting a gene polymorphism of a gene encoding at least any one protein or cDNA of CNIH2-PACS1, ALDH2, MYL2-CUX2, GCKR, MAP3K11, NPT4, ABCG2, HIST1H2BF/HIST1H4E, HIST1H2BE/HIST1H4D, and FAM35A, or a combination thereof with gene polymorphisms of GLUT9, NPT1, URAT1, and NXRN2, using a test sample containing human genes of the subject.

Furthermore, the detection of a gene polymorphism of a gene encoding any one protein or cDNA of CNIH2-PACS1, ALDH2, MYL2-CUX2, GCKR, MAP3K11, NPT4, ABCG2, HIST1H2BF/HIST1H4E, HIST1H2BE/HIST1H4D, and FAM35A, or a combination thereof with GLUT9, NPT1, URAT1, and NXRN2 may be the detection of a SNP or a polymorphism having a relationship of linkage disequilibrium with the SNP or a polymorphism with a frequency of 1% or less.

Herein, a combination with detection of SNPs of CNIH2-PACS1, ALDH2, MYL2-CUX2, GCKR, MAP3K11, NPT4, HIST1H2BF/HIST1H4E, HIST1H2BE/HIST1H4D, and FAM35A (rs4073582, rs671, rs2188380, rs1260326, rs10791821, rs56027330, rs11758351, rs4496782, and rs7903456, respectively), or a gene polymorphism having a relationship of linkage disequilibrium with the SNPs, or other gene polymorphisms may be used.

Furthermore, detection of gene polymorphisms of G279R of NPT4, and V178I, N299S, E311K, G462R, V508I, V516M, A634V, F489L, and D620G of ABCG2, or a gene polymorphism having a relationship of linkage disequilibrium with the polymorphisms, and a combination thereof may be used.

A combination of detection of a SNP of GLUT9 (rs3775948), gene polymorphisms (SNPs) of NPT1 (rs1165196 and I269T), a SNP of URAT1 (rs505802), a SNP of NXRN2 (rs2285340 or rs506338), or polymorphisms having a relationship of linkage disequilibrium therewith, or W258X and R90H of URAT1, and SNPs (Q126X, Q141K, and V12M) and polymorphisms (R113X, F208S, G268R, P269S, E334X, S441N, L447V, S486N, F506SfsX4, R575X, and C608X) of ABCG2 may be used.

Furthermore, in evaluation using a test sample containing human genes of the subject, based on Q126X and Q141K of two SNPs of genes encoding ABCG2 protein, when a gene encoding Q of Q126X is C/C and a gene encoding Q of Q141K is C/C, the function of ABCG2 is evaluated to be normal; when a gene encoding Q of Q126X is C/C, and a gene encoding Q of Q141K is A/C, the function of ABCG2 is evaluated to be ¾; when a gene encoding Q of Q126X is T/C and a gene encoding Q of Q141K is C/C, the function of ABCG2 is evaluated to be ½; when a gene encoding Q of Q126X is C/C and a gene encoding Q of Q141K is A/A, the function of ABCG2 is evaluated to be ½; when a gene encoding Q of Q126X is T/C and a gene encoding Q of Q141K is A/C, the function of ABCG2 is evaluated to be ¼; and when a gene encoding Q of Q126X is T/T and a gene encoding Q of Q141K is C/C, ABCG2 is evaluated to have no function. The method may evaluate that a diathesis capable of inducing urate regulation failure, or a state or a disease attributable to the failure is evaluated to be high depending on a degree of loss of the function of ABCG2.

Furthermore, when one polymorphism which produces an amino acid variation of any one of V178I, N299S, E311K, G462R, V508I, V516M, A634V, R113X, F208S, G268R, E334X, S441N, S486N, and F506SfsX4 of ABCG2 is present, it may be evaluated that a subject has a diathesis capable of inducing urate regulation failure or a state or a disease attributable to the failure, substantially similar to the case in which one Q126X is present.

When one polymorphism which produces an amino acid variation of any one of L447V, R575X, and C608X of ABCG2 is present, it may be evaluated that a subject has a diathesis capable of inducing urate regulation failure or a state or a disease attributable to the failure, substantially similar to the case in which one Q126X is present.

Presence of one polymorphism which produces an amino acid variation of any one of V12M, P269S, F489L, and D620G of ABCG2 may be evaluated to be associated with a diathesis capable of inducing urate regulation failure or a state or a disease attributable to the failure.

Furthermore, the method may evaluate estimation of clinical disease types or suitable drugs based on the result obtained by the method for evaluating a uric acid-related disease diathesis and an inflammation-related disease diathesis mentioned above.

When a serum uric acid level is a predetermined value or more, it may be evaluated that a subject has a high diathesis capable of inducing urate regulation failure or a state or a disease attributable to the failure.

A suitable threshold of the serum uric acid level is in a range from 6.0 to 9.0 mg/dl, and more preferably in a range from 7.0 to 8.0 mg/dl.

Examples of the uric acid-related diseases and inflammation-related diseases include hyperuricemia, gout, rheumatoid arthritis, osteoarthritis, infertility, cerebral stroke, neurodegenerative disease, ischemic heart disease, chronic kidney disease, renal dysfunction, urolithiasis, kidney stone, aneurysm, arrhythmia including atrial fibrillation, inflammatory bowel disease, enteritis, functional dyspepsia, viral intestinal disease, and photosensitivity.

The evaluation kit for uric acid-related disease diathesis and inflammation-related disease diathesis according to the present invention is a kit for evaluating whether or not a subject has a diathesis capable of inducing urate regulation failure, or a state or a disease attributable to the failure, wherein the kit includes means for detecting a SNP of at least any one gene selected from CNIH2-PACS1, ALDH2, MYL2-CUX2, GCKR, MAP3K11, NPT4, ABCG2, HIST1H2BF/HIST1H4E, HIST1H2BE/HIST1H4D, and FAM35A genes, or a gene polymorphism having a relationship of linkage disequilibrium with the SNP, or a polymorphism having a frequency of 1% or less, or a combination thereof with a gene polymorphism of GLUT9, NPT1, URAT1, and NXRN2, using a test sample containing human genes of the subject.

Herein, for the SNP of CNIH2-PACS1, ALDH2, MYL2-CUX2, GCKR, MAP3K11, NPT4, GLUT9, NPT1, URAT1, NXRN2, HIST1H2BF/HIST1H4E, HIST1H2BE/HIST1H4D, and FAM35A, rs4073582, rs671, rs2188380, rs1260326, rs10791821, rs56027330, rs3775948, rs1165196, rs505802, rs2285340, or rs506338, rs11758351, rs4496782, and rs7903456 can be used.

Furthermore, detection of ABCG2 genes may include detection of at least any one of or combination of V178I, N299S, E311K, G462R, V508I, V516M, A634V, F489L, D620G, Q126X, Q141K, V12M, R113X, F208S, G268R, P269S, E334X, S441N, L447V, S486N, F506SfsX4, R575X, and C608X.

The inspection object of the present invention is a living body in which urate transport kinetics is to be examined. The inspection object includes: a nonhuman animal having a deficiency of at least any one gene selected from CNIH2-PACS1, ALDH2, MYL2-CUX2, GCKR, MAP3K11, NPT4, ABCG2, GLUT9, NPT1, URAT1, NXRN2, HIST1H2BF/HIST1H4E, HIST1H2BE/HIST1H4D, and FAM35A; or a nonhuman animal overexpressing or decreased-expressing at least any one gene selected from human CNIH2-PACS1, ALDH2, MYL2-CUX2, GCKR, MAP3K11, NPT4, ABCG2, GLUT9, NPT1, URAT1, NXRN2, HIST1H2BF/HIST1H4E, HIST1H2BE/HIST1H4D, and FAM35A, or at least any one gene selected from nonhuman CNIH2-PACS1, ALDH2, MYL2-CUX2, GCKR, MAP3K11, NPT4, ABCG2, GLUT9, NPT1, URAT1, NXRN2, HIST1H2BF/HIST1H4E, HIST1H2BE/HIST1H4D, and FAM35A; a nonhuman animal overexpressing or decreased-expressing a human ABCG2 gene or nonhuman human ABCG2 gene including at least any one polymorphism selected from V178I, N299S, E311K, G462R, V508I, V516M, A634V, F489L, D620G, Q126X, Q141K, V12M, R113X, F208S, G268R, P269S, E334X, S441N, L447V, S486N, F506SfsX4, R575X, and C608X of ABCG2, or a combination thereof; a nonhuman cell line or a human cell line having a deficiency of at least any one gene of CNIH2-PACS1, ALDH2, MYL2-CUX2, GCKR, MAP3K11, NPT4, ABCG2, GLUT9, NPT1, URAT1, NXRN2, HIST1H2BF/HIST1H4E, HIST1H2BE/HIST1H4D, and FAM35; a nonhuman cell line or a human cell line overexpressing or decreased-expressing at least any one gene selected from human CNIH2-PACS1, ALDH2, MYL2-CUX2, GCKR, MAP3K11, NPT4, ABCG2, GLUT9, NPT1, URAT1, NXRN2, HIST1H2BF/HIST1H4E, HIST1H2BE/HIST1H4D, or nonhuman CNIH2-PACS1, ALDH2, MYL2-CUX2, GCKR, MAP3K11, NPT4, ABCG2, GLUT9, NPT1, URAT1, NXRN2, HIST1H2BF/HIST1H4E, HIST1H2BE/HIST1H4D, and FAM35A; a nonhuman cell line or a human cell line overexpressing or decreased-expressing human ABCG2 gene or a nonhuman ABCG2 gene including at least any one polymorphism selected from V178I, N299S, E311K, G462R, V508I, V516M, A634V, F489L, D620G, Q126X, Q141K, V12M, P269S, R113X, F208S, G268R, E334X, S441N, L447V, S486N, F506SfsX4, R575X, and C608X of ABCG2, or combination thereof; or a cell membrane vesicle prepared from the cell lines.

A drug for uric acid-related diseases and inflammation-related diseases of the present invention is a drug for uric acid-related diseases and inflammation-related diseases, for reducing a diathesis capable of inducing urate regulation failure, or a state or a disease attributable to the failure. The drug includes polynucleotide or polypeptide encoding at least any one protein selected from CNIH2-PACS1, ALDH2, MYL2-CUX2, GCKR, MAP3K11, NPT4, ABCG2, HIST1H2BF/HIST1H4E, HIST1H2BE/HIST1H4D, and FAM35A, or combination thereof with GLUT9, NPT1, URAT1, and NXRN2 in a form capable of being introduced into cells.

Advantageous Effects of Inventions

The present invention contributes to early treatment and prevention of diseases related to uric acid regulation.

With the improvement of a nutritional state, hyperuricemia continues to increase. Although only a part of hyperuricemias that advances to gout, many patients with hyperuricemias undergo treatment with a urate lowering drug regardless of the onset of gout. On the contrary, the present invention can previously obtain information—such as loss or decrease in function of gout-related genes, which lead to identification of patients who should preferentially start treatment, reduction of medical care expenditure of the urate lowering drug and the like, and reduction of physical and economic burdens of persons who are likely to develop gout. Furthermore, the present invention contributes to measurement of effects of various types of medication because a gout-related gene transports anti-cancer drugs, therapeutic agents for various types of lifestyle-related diseases, and the like. Furthermore, the present invention enables specific measures for lifestyle, for example, setting of target values for diet to be set, and therefore, contributes to early prevention and early treatment of individual cases.

BRIEF DESCRIPTION OF THE DRAWINGS

FIG. 10 is a table showing five SNPs associated with gout at a genome-wide significant level and one suggestive SNP.

FIG. 12 is a table showing the relationship between seven SNPs and subtypes of gout and urate-transport parameters which the subtypes are based on.

FIG. 15 is a table showing analysis results of the association between gout and tag SNPs of MYL2-CUX2 locus, as well as effects of analysis results of tag SNPs with adjustment by rs671.

FIG. 16 is a table showing analysis results of the association between gout and ALDH2 gene rs671 or alcohol drinking.

FIGS. 19A and 19B are an explanatory diagram showing haplotypes of ABCG2.

FIG. 21 is a table showing frequency of ABCG2 function in Japanese individuals.

FIG. 23 is an explanatory diagram showing a significant increase of the serum uric acid level by ABCG2 dysfunction.

FIG. 30 is an explanatory diagram showing positions of seven types of amino acid variations of ABCG2 (SEQ ID NO:1).

FIG. 35 is a table showing polymorphisms and variations of ABCG2.

FIG. 36 is a table showing the results of analysis of the relationship between gout and a gene polymorphism rs1165196 of NPT1/SLC17A1.

FIGS. 41A and 41B are tables showing the results of an analysis of the relationship between hyperuricemia and URAT1 nonsynonymous variants.

FIG. 42 is a table showing a result of genome-wide association study of gout after replication analysis using a custom chip.

FIG. 43 is a table showing the results of analysis of the change of urinary coproporphyrin based on the function of ABCG2.

FIG. 44 is a table showing the results of analysis of the relationship between the function of ABCG2 and cerebral stroke.

FIG. 45 is a table showing the results of analysis of the serum uric acid levels in ulcerative colitis case based on the function of ABCG2.

FIG. 46 is a table showing the results of analysis of the serum uric acid level before treatment of viral enteritis cases based on the function of ABCG2.

FIGS. 47A and 47B are a table showing the results of analysis of the relationship between function of ABCG2 and ages at which dialysis is introduced and the serum uric acid levels in hemodialysis cases.

DESCRIPTION OF EMBODIMENTS

The present inventors have found a high-capacity transporter of urate as an extension of the findings disclosed in Non-Patent Literatures 1 to 2 and 5, and the like, and thus reached the present invention.

The present invention will be described below by showing demonstration experiments constituting the basis of the present invention. Embodiments of the present invention are not limited to the below-mentioned Examples, and design can be changed by appropriately using conventionally known techniques.

Although Japanese individuals are mainly described as the subject herein, the present invention can be similarly applied to other races. This is also based on the background that it is known that the prevalence of gout is high in the Pacific Rim population including Taiwanese aborigines, and the gene noted in the present invention, ABCG2, is present in a gene region on the long arm of the fourth chromosome found by a linkage study of 21 pedigrees in Taiwan with the onset of gout.

The ATP-binding cassette, subfamily G, member 2 gene ABCG2/BCRP locates in a gout-susceptibility locus (MIM138900) on chromosome 4q, and it has a function of encoding a multispecific transporter that is expressed on the apical membrane in several tissues including intestine, liver, and kidney. Also, ABCG2 is a transporter of nucleotide analogues that are structurally similar to urate (Non-Patent Literature 3).

From GWAS at serum uric acid level, gene loci including those of SLC2A9 and ABCG2 have been identified, and subsequent genetic and functional studies have clarified biological and pathological importance of ABCG2 encoding an urate exporter as a major genetic risk of gout.

GWAS of gout was carried out three times. All the GWAS includes self-stating gout patients (Non-Patent Literatures 4 to 6), and provided poor clinical information. In order to understand genetic basis of gout more sufficiently, the present inventors carried out GWAS of gout using only clinically defined cases for the first time. In addition, the relationship between genetic variation and gout subtype was evaluated based on the urate-transport parameters, they have clarified genetic heterogeneity of the gout subtype.

Participants of this time GWAS include 946 clinically defined Japanese male patients and 1213 male controls. All samples were genotyped by using Illumina, and then strict quality control filtering was carried out. Based on the analysis of main components, one gout patient estimated to be a hybrid of East Asian race and Europe race was excluded.

Figure 1:
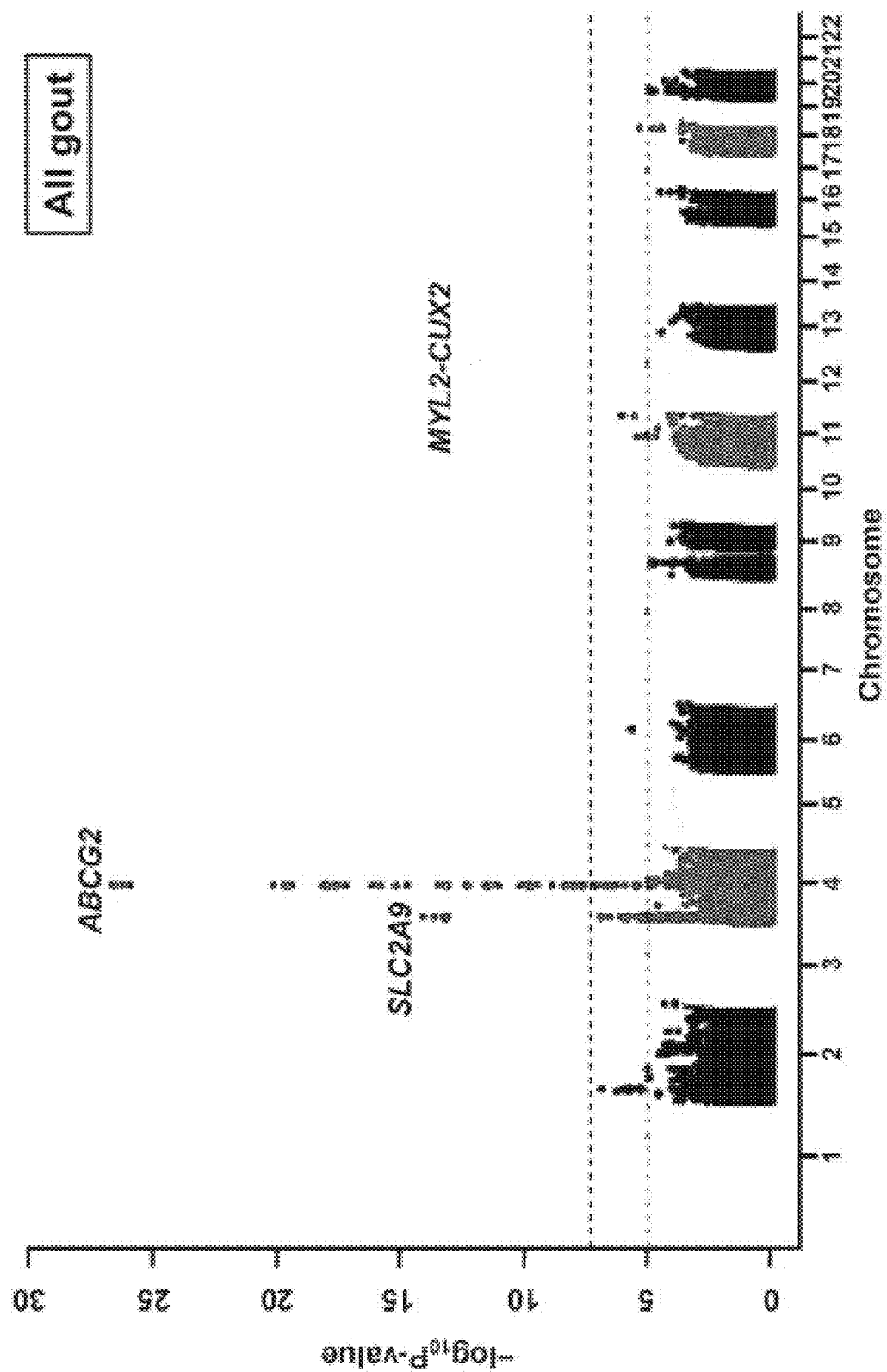
FIG. 1 is a Manhattan plot graph of the genome-wide association study of all gouts.
Figure 2:
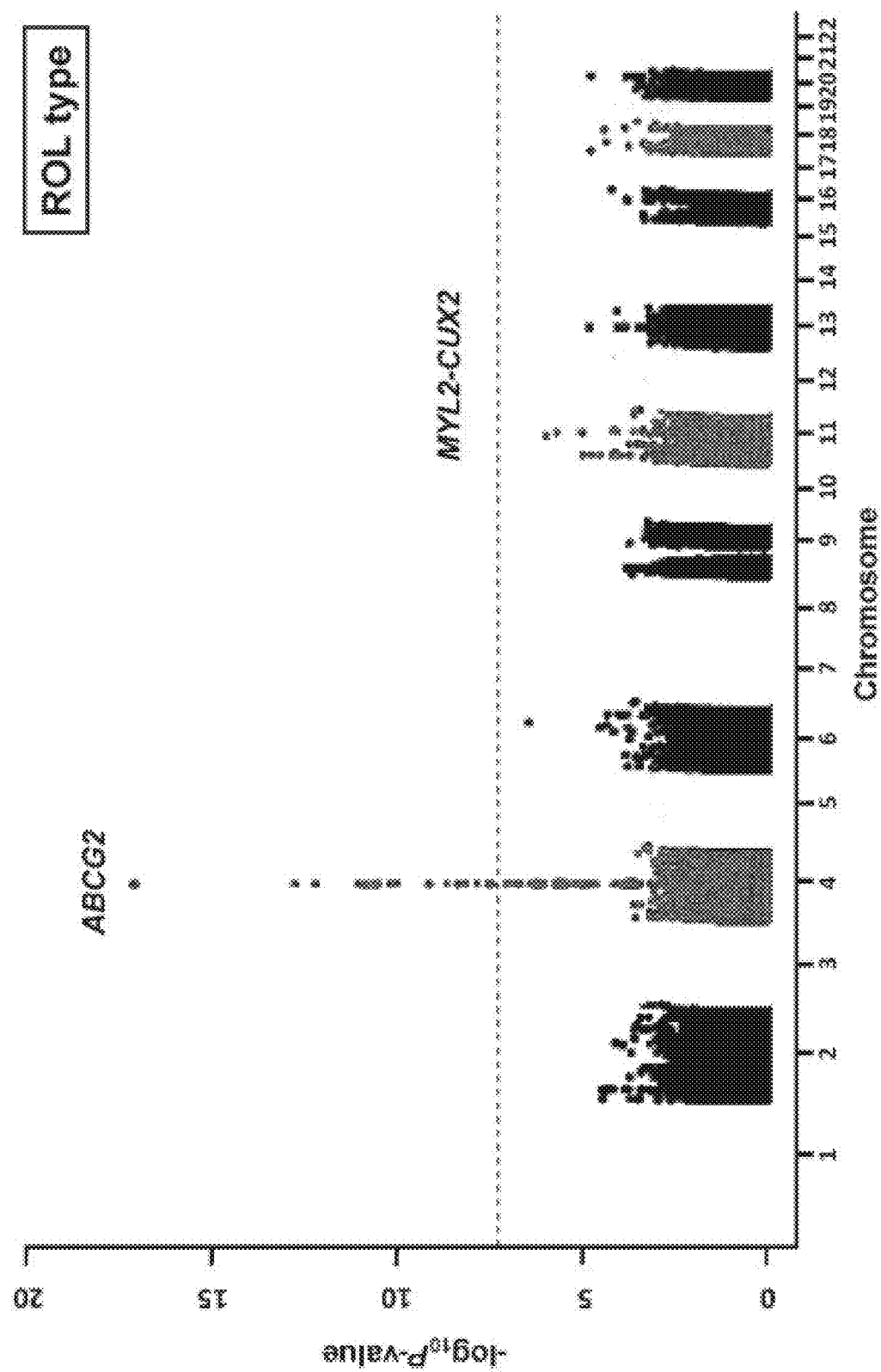
FIG. 2 is a Manhattan plot graph of the genome-wide association study of a ROL type grout.
Figure 3:
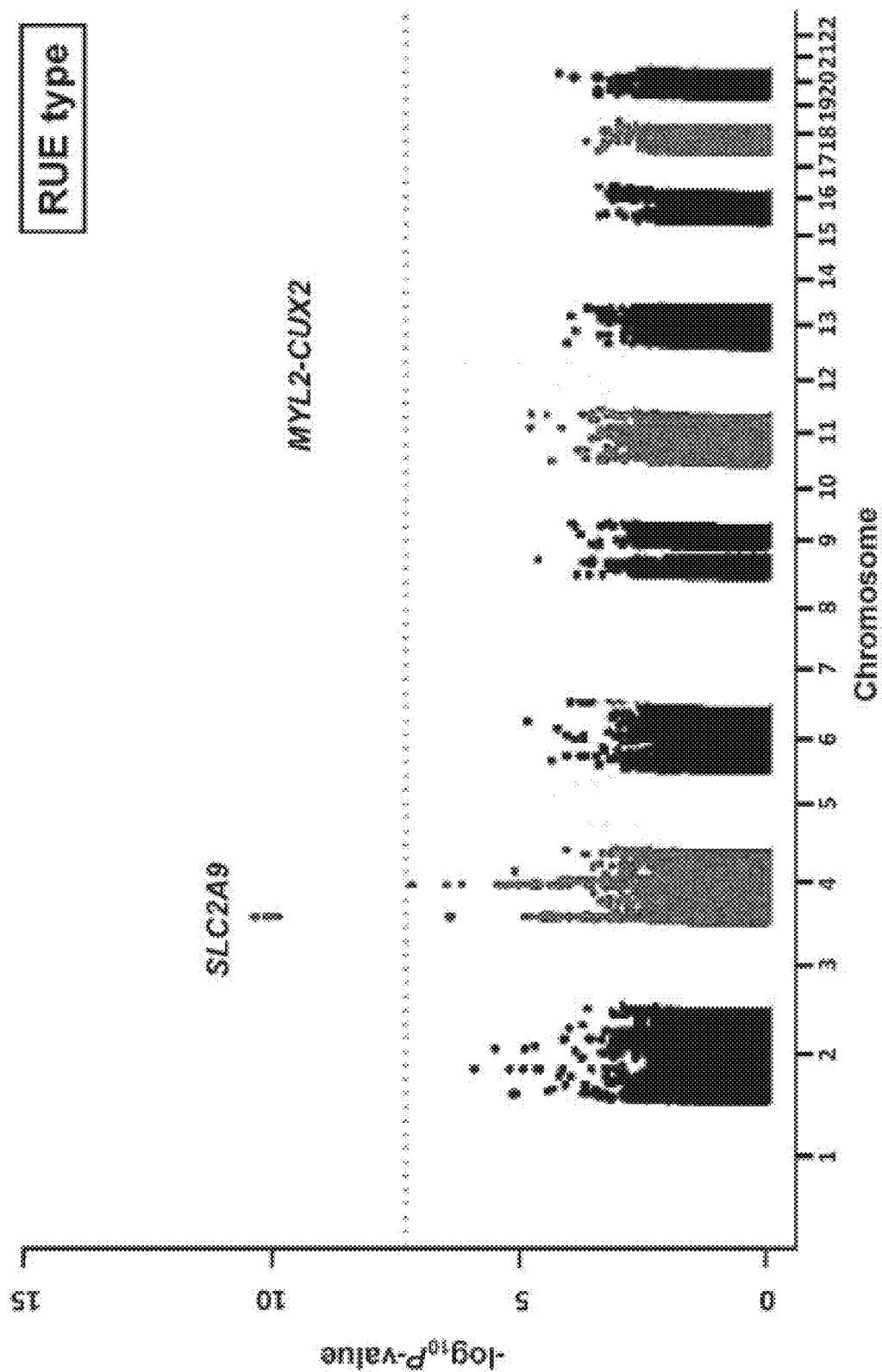
FIG. 3 is a Manhattan plot graph of the genome-wide association study of a RUE type grout.
Figure 4:
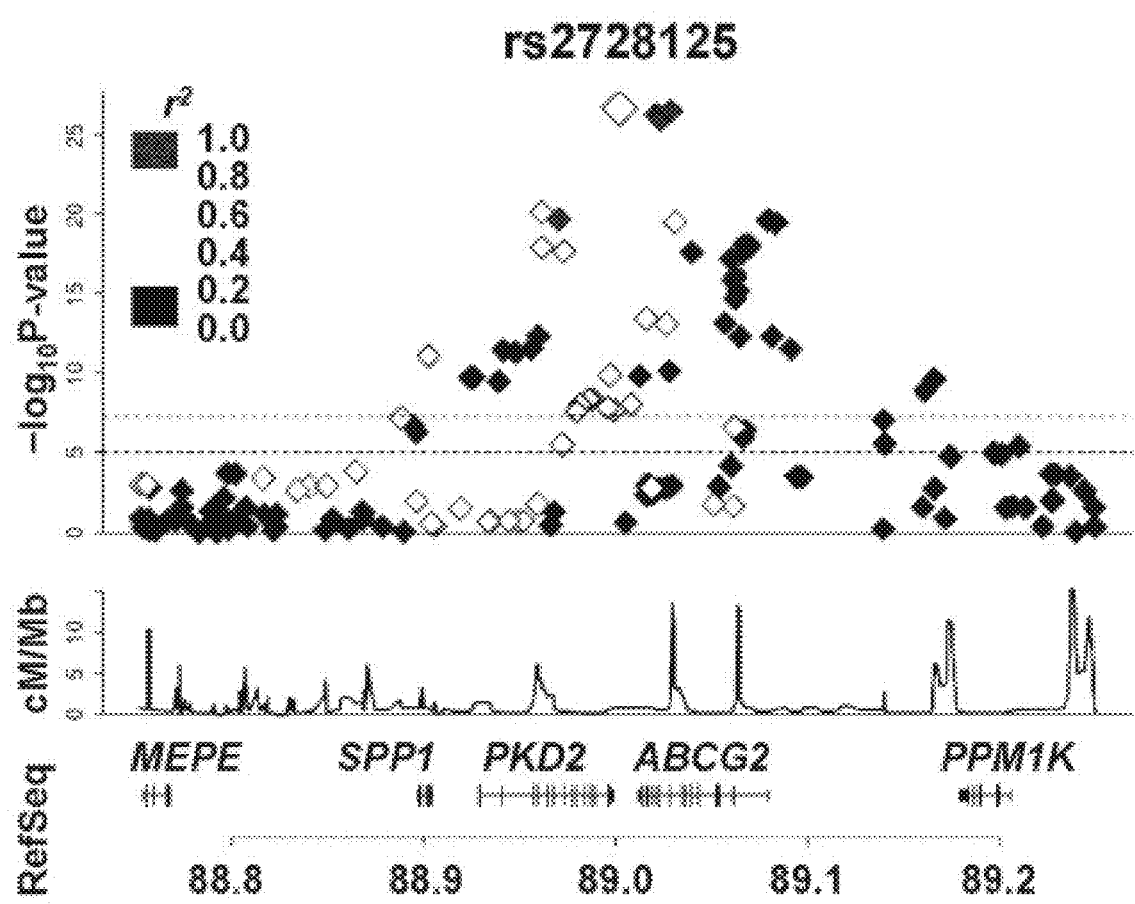
FIG. 4 is a graph showing a genomic region of ABCG2, including genome-wide significant association.
Figure 5:
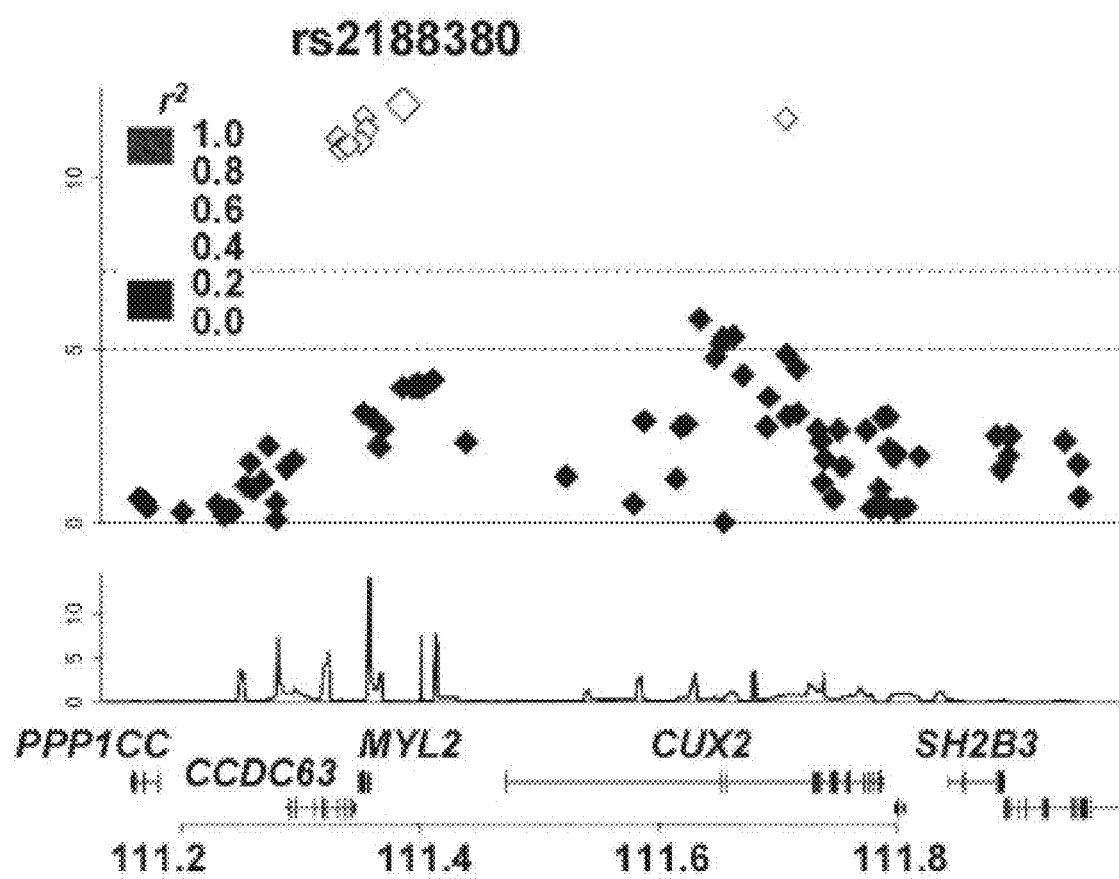
FIG. 5 is a graph showing a genomic region of MYL2-CUX2, including genome-wide significant association.
Figure 6:
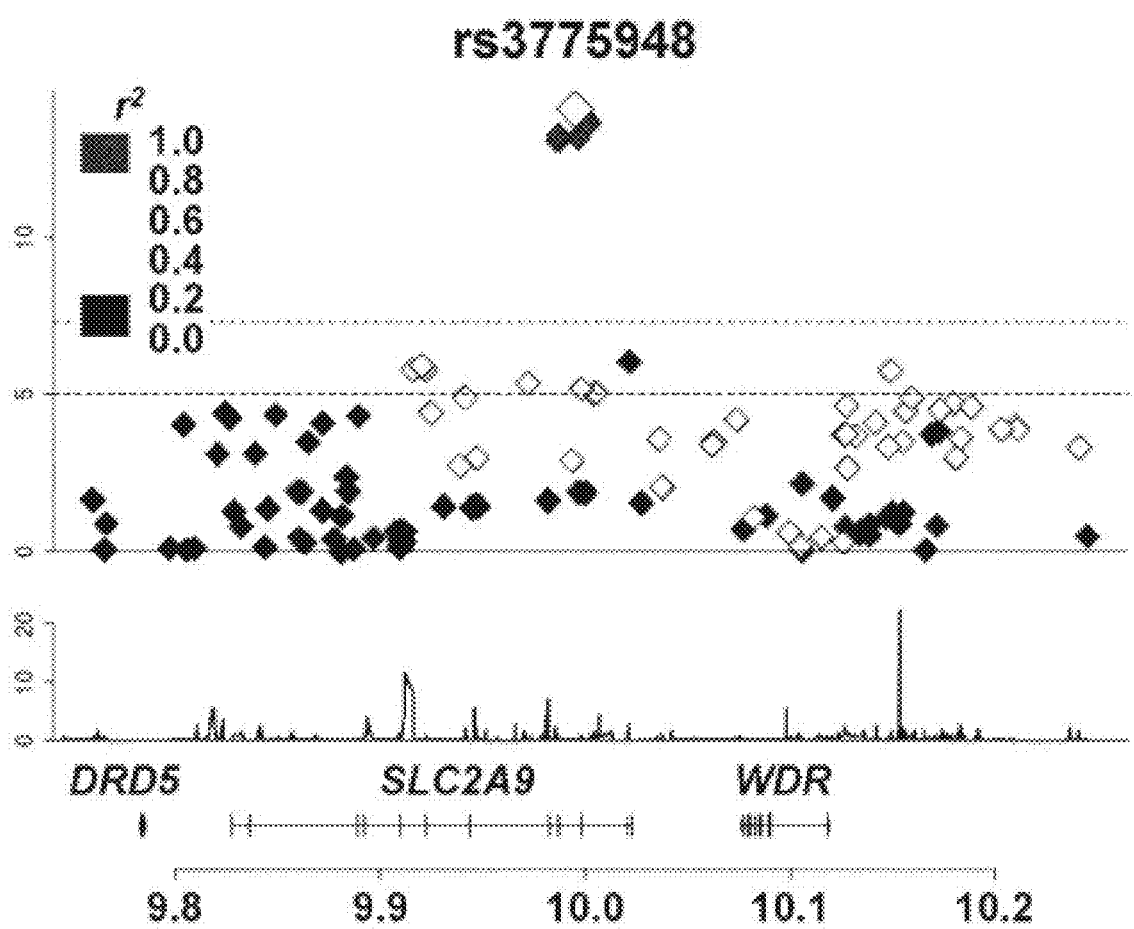
FIG. 6 is a graph showing a genomic region of SLC2A9, including genome-wide significant association.
Figure 7:
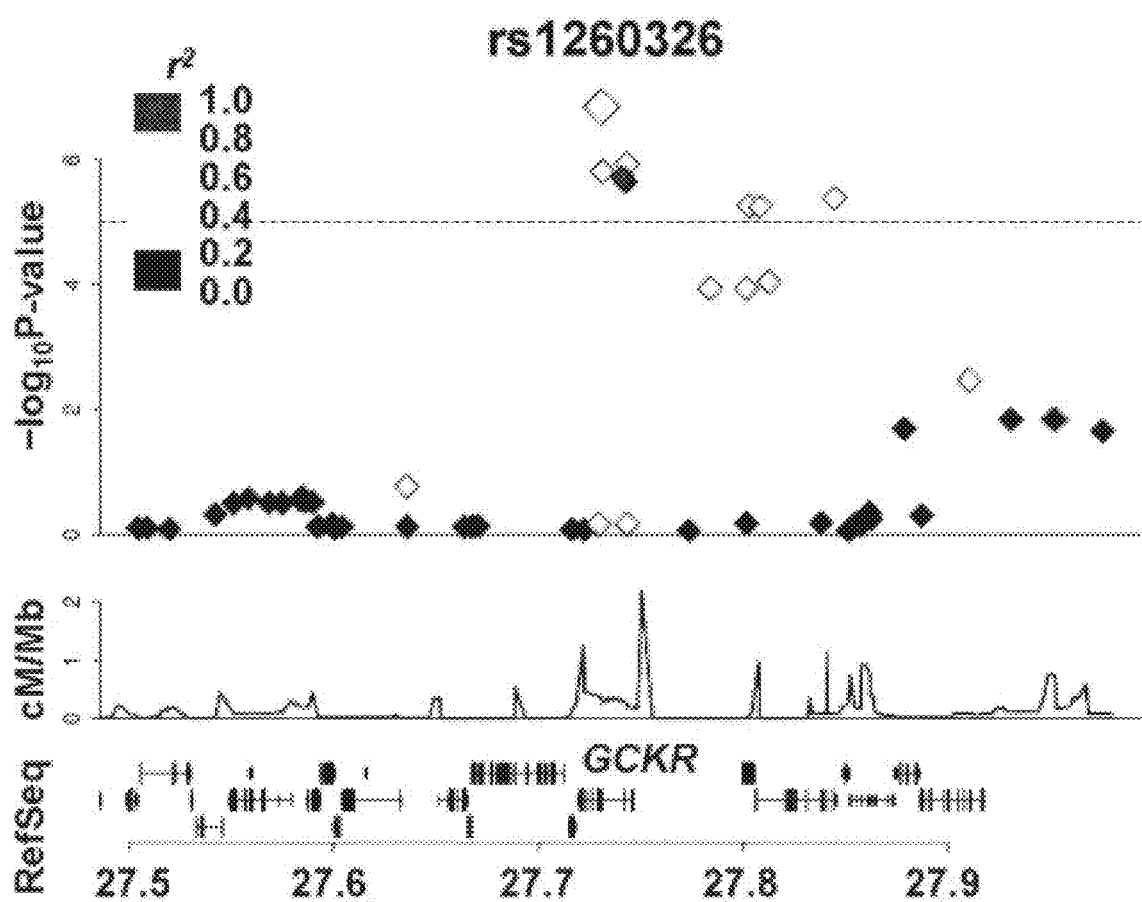
FIG. 7 is a graph showing a genomic region of GCKR, including genome-wide significant association.

FIGS. 1 to 3 are Manhattan plot graphs respectively showing genome-wide association studies with respect to all gout, ROL type, and RUE type. X-axis shows chromosome positions; Y-axis shows $-\log_{10}$ P-values. The horizontal black dotted line indicates the genome-wide significance threshold and a gray dotted line indicates the cut-off level for selecting SNP for replication study ($P=5.0\times10^{-8}$), respectively.

FIGS. 4 to 9 are graphs showing five genomic regions including genome-wide significant association, respectively showing plots of ABCG2, MYL2-CUX2, SLC2A9, GCKR, CNIH2-PACS1, and MAP3K11. They show regions within 250 Kb from an SNP showing the minimum P-value. The upper panel shows a plot of $-\log_{10}$ P-values related to the test of the relationship between the SNP and gout, and shows the SNP having the minimum P-value by pink-colored diamonds. The other SNPs are classified by colors according to the degree of the level linkage disequilibrium with the SNP showing the minimum P-value (evaluated by $r^2$). The center panel shows plotting of recombinant frequency (centimorgan/Mb) estimated from the phase II data of HapMap are plotted. The lower panel is a RefSeq gene, and the genomic locus is based on the Genome Reference Consortium GRCh37.

In the GWAS stage, SNPs were specified at three gene luci showing evidence of genome-wide association at a significant level. As shown in FIGS. 1 and 4 to 6, the SNPs were rs2728125 of ABCG2 ($P=1.5\times10^{-27}$; odds ratio [OR]=2.05), rs3775948 of SLC2A9 ($P=6.7\times10^{-15}$; odds ratio [OR]=1.64), and rs2188380 of MYL2-CUX2 ($P=5.7\times10^{-13}$; odds ratio [OR]=1.78). In order to identify risk gene loci by validating these gene loci, independent samples of 1048 cases and 1334 controls were employed. In the GWAS stage, among 124 SNPs showing the association in the range of $P<5.0\times10^{-8}$, 17 SNPs were selected for a replication analysis with the linkage disequilibrium considered. The genotypes of these 17 SNPs were determined by TaqMan assay.

FIG. 10 is a table showing five SNPs associated with gout at a genome-wide significant level and one suggestive SNP. "Chr." represents chromosome, "Freq." represents frequency of A1, "OR" represents an odds ratio, and "CI" represents confidence interval. In "$^a$dbSNP rs number", a suggestive SNP is marked with "†". "$^b$": Positions of SNPs are based on NCBI human genome reference sequence Buid 37.4; "$^c$": A1 represents risk-associated allele and A2 represents non-risk-associated allele. "$^d$": 945 gout cases and 1,213 controls. "$^e$": 1,048 gout cases and 1,334 controls. "$^f$": Meta-analysis combining GWAS and replication samples (1,993 gout cases and 2,547 controls).

In the GWAS stage, in three SNPs (rs2728125 of ABCG2, rs3775948 of SLC2A9, and rs2188380 of MYL2-CUX2) that are beyond genome-wide significant threshold, appropriate reproducibility was obtained.

Furthermore, two SNPs (rs1260326 of GCKR and rs4073582 of CNIH2-PACS1) showed significant association with gout at $P<2.9\times10^{-3}$ (17 tests were adjusted by the Bonferroni correction).

As shown in FIGS. 5 to 7, and 10, all of these five SNPs reached genome-wide significance in the meta-analysis composed of GWAS and a replication experiment (rs1260326 of GCKR ($P_{meta}=1.9\times10^{-12}$; OR=1.36), rs4073582 of CNIH2-PACS1 ($P_{meta}=6.4\times10^{-9}$; OR=1.66), and intron SNP (rs10791821) of MAP3K11 showed association at a suggestive level ($P_{meta}=1.0\times10^{-7}$; OR=1.57).

The discovered five risk gene loci include a plurality of genes responsible for-metabolic pathways. ABCG2 and SLC2A9 are well-known urate transporter genes associated with the serum uric acid level and gout. The present inventors formerly showed that two nonsynonymous SNPs of ABCG2, that is, rs72552713 (Gln126Ter) and rs2231142 (Gln141Lys), are strongly associated with hyperuricemia and gout (Non-Patent Literatures 7 to 9). The risk alleles of these two SNPs are present on different haplotypes. Also in GWAS, SNP (rs2728125) having the highest significant association was in a strong LD state with rs2231142 ($r^2=0.755$). Multivariate logistic regression analysis including these three SNPs of ABCG2 shows that rs2728125 no longer shows significant association (P=0.19), but two nonsynonymous SNPs, that is, rs72552713 and rs2231142, remain highly significant. This suggests that rs2728125 is just a sarrogate marker for true causal nonsynonymous variant.

The frequency of allele (Glu504Lys) of rs671 of ALDH2 is different among populations, this Glu 504Lys allele is general in East Asian populations including Japanese population, but extremely rare in the other populations such as European or African descent. Therefore, in the GWAS of gout in European and African American, SNP is not likely to be detected because of low frequency. ALDH2 is an important gene in alcohol metabolism, and alcohol metabolism covert acetaldehyde into acetic acid by oxidization in the degradation process of alcohol. The Glu 504Lys allele decreases the enzymatic activity of ALDH2. Recent study shows that rs671 is associated with alcohol drinking behavior, and the alcohol drinking is well-known to be a risk factor of gout.

GCKR suppresses glucokinase (GCK) which is an important enzyme for glucose metabolism during fasting.

The gout risk allele of rs1260326 is associated with the increase in the level of triglyceride and serum uric acid. Further, its association with dyslipidemia is also reported. The present GWAS is the first report to show that a common missense variant of GCKR is associated with gout at a genome-wide significant level.

Figure 8:
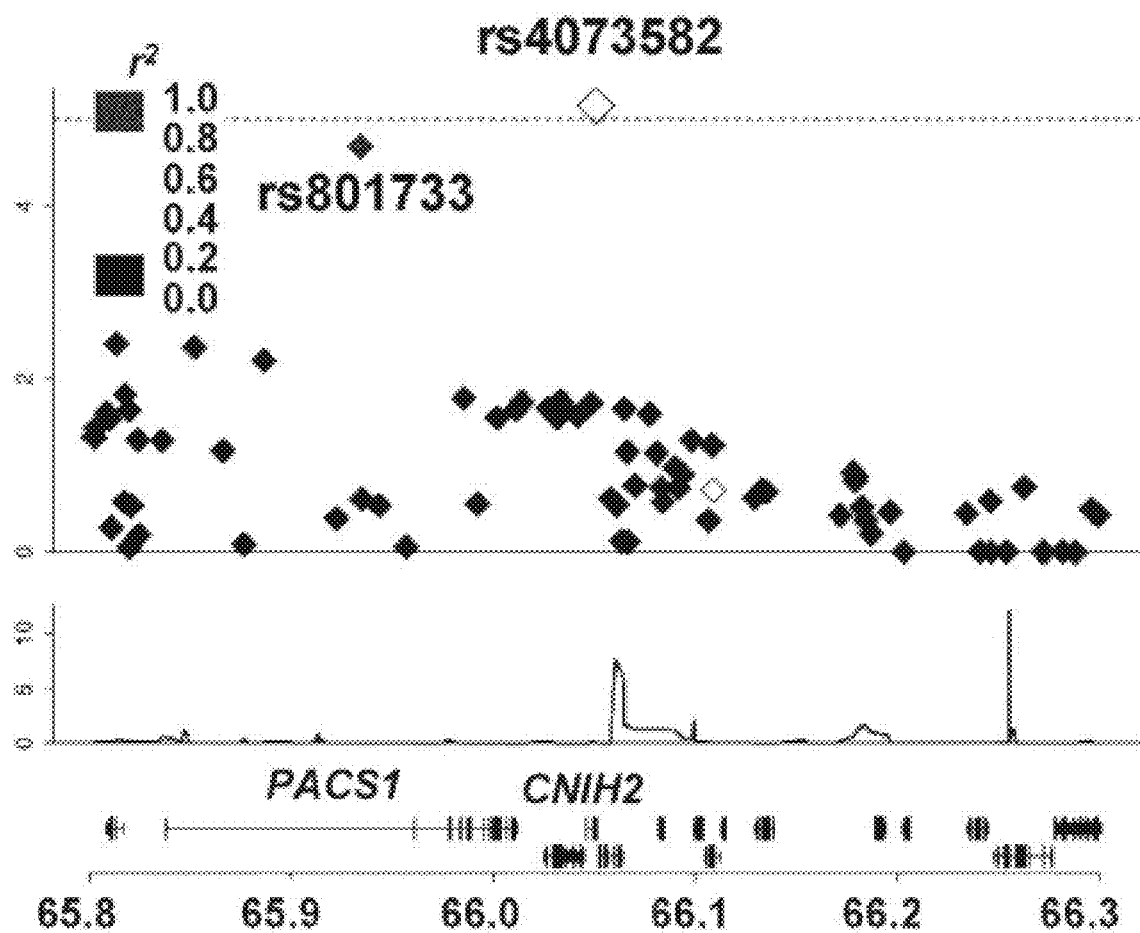
FIG. 8 is a graph showing a genomic region of CNIH2-PACS1, including genome-wide significant association.
Figure 9:
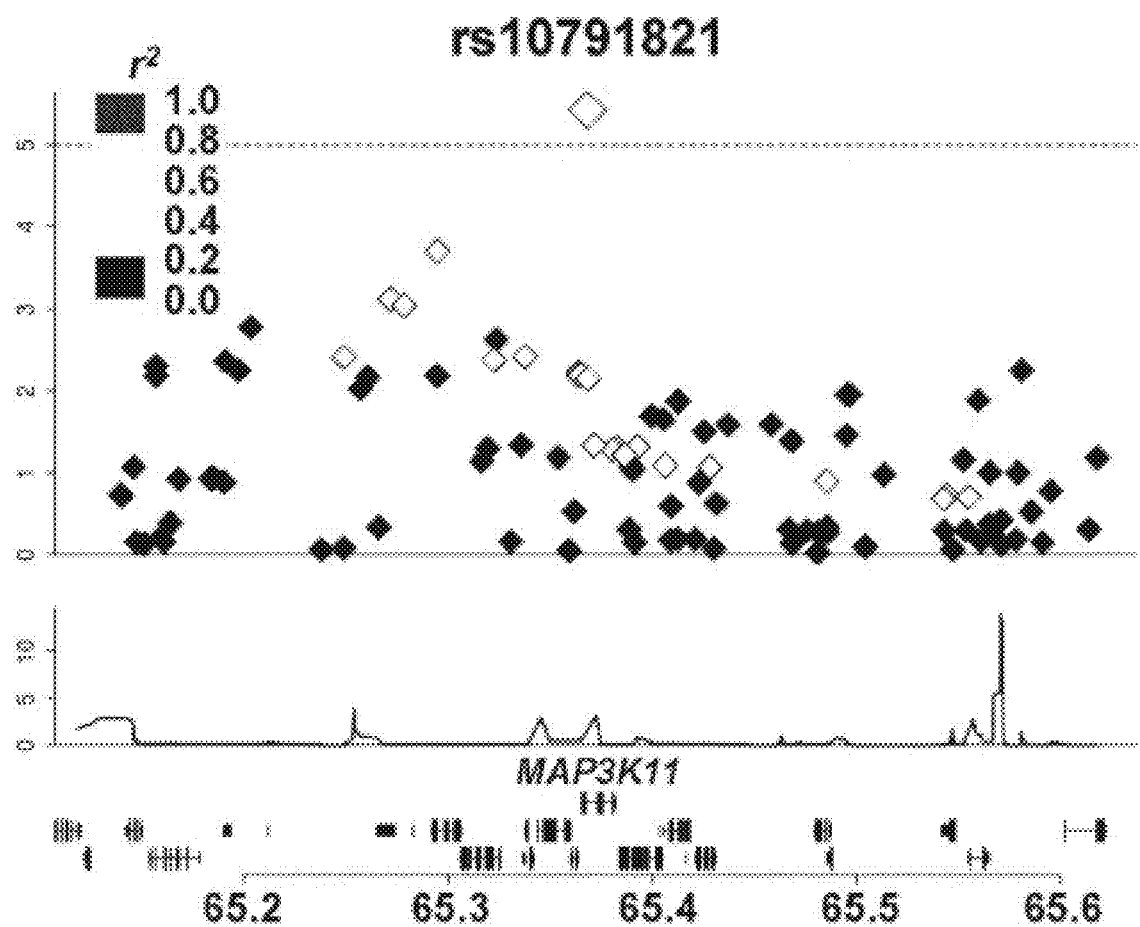
FIG. 9 is a graph showing a genomic region of MAP3K11.

It is known that CNIH2-PACS1 modulates the function of a glutamate receptor of AMPA-subtype (AMPAR). CNIH2-PACS1 amplifies the surface expression of AMPAR, and modulates gating thereof. Furthermore, CNIH2-PACS1 mediates synaptic transmission of AMPAR in hippocampus. At the same time, rs4073582 of CNIH2-PACS1 was in a strong LD state with rs801733 of phosphofurin acidic cluster sorting protein 1 which was associated with severe obesity ($r^2=0.966$) (FIG. 8). Therefore, also PACS1 can be a highly susceptible gene as a good candidate gene.

A suggestive level association was detected between rs10791821 of MAP3K11 and gout. This SNP was associated with the expression level of MAP3K11 in the monocyte ($P=6.95\times10^{-17}$). Further investigation is needed in order to determine association with gout. This finding would be a clue to a new molecule mechanism of gout. MAP3K11 is a member of MAP3K super family, and is known to activate c-Jun N-terminal kinase (JNK) that is a protein kinase activated by stress. Interestingly, this JNK pathway is activated by phagocytosis of MSU crystal by monocyte and macrophage, thus causing gouty arthritis.

Figure 11:
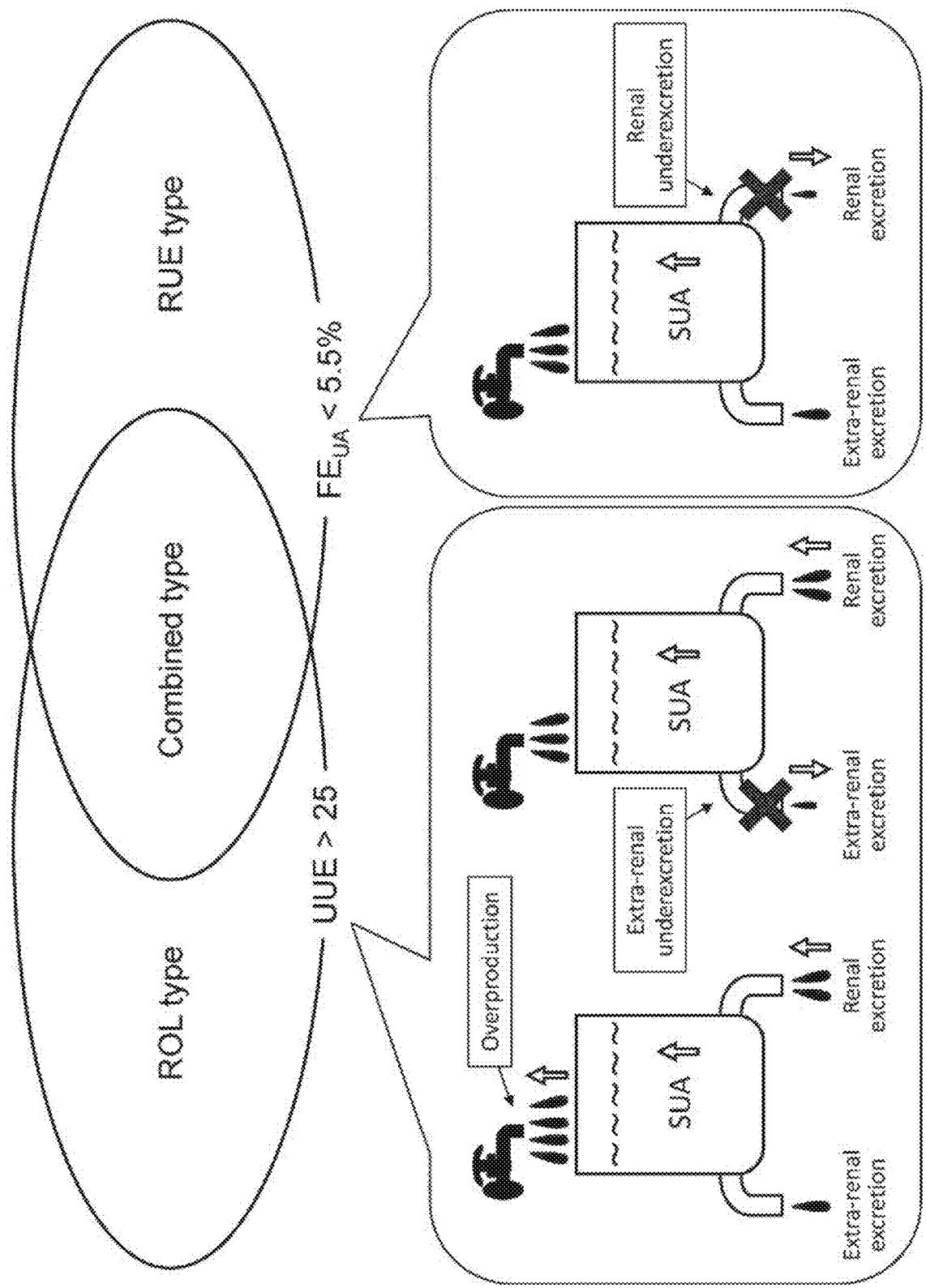
FIG. 11 is an explanatory diagram showing classification of gout.

FIG. 11 is an explanatory diagram showing classification of gout. Genetic heterogeneity of gout subtypes was examined based on ROL type gout and RUE type gout having different features based on the amount of uric acid clearance ($FE_{UA}$) and kidney urate excretion (UUE) (Non-Patent Literature 7). Subtype-specific GWAS showed apparent differences in association signals (FIGS. 2 to 3), ROL and RUE type-specific GWAS showed peak signals on ABCG2 and SLC2A9, respectively. On the other hand, an association signal in MYL2-CUX2 did not show difference between these subtypes. Whether or not the degree of association is different depending on subtypes between the identified SNPs and gout was examined by an analysis of subtype-specific OR and a case-subtype heterogeneity test. According to this subgroup analysis, the association of two nonsynonymous SNPs (rs72552713 and rs2231142) of ABCG2 is stronger in the ROL type (OR=4.35 and 3.37) than in the RUE type (OR=1.28 and 1.88, respectively). The difference in OR between these subtypes were extremely significant ($P=2.4\times10^{-5}$ and $1.0\times10^{-7}$). On the other hand, association of rs3775948 of SLC2A9 was stronger in the RUE type (OR=1.94) than in the ROL type (OR=1.38). The case-subtype heterogeneity test showed significant difference in OR ($P=2.7\times10^{-4}$). The other SNPs did not show significant differences in OR between subtypes.

FIG. 12 is a table showing the relationship between seven SNPs and subtypes of gout and urate-transport parameters which the subtypes are based on, respectively. "$FE_{UA}$" represents an excretion rate of urate clearance (unit: %), "UUE" represents urinary urate excretion (unit: mg/hour/1.73 m$^2$), "ROL" represents renal overload, "RUE" represents renal underexcretion, "Coef." represents regression coefficient, "OR" represents an odds ratio, and "CI" represents a confidence interval. "$^a$": dbSNP rs number. "$^b$": the present inventors performed multivariate logistic regression analyses, in which all the seven SNPs, alcohol drinking and BMI were included in the model; 1,613 gout patients and 1,334 controls with genotypes for rs72552713 and rs2231142 of ABCG2, which were not on illumina Omni-Express platform, were used, and 375 and 509 gout patients were grouped into sub-phenotypes, that is, the ROL type and the RUE type, respectively. "c": P-values of less than 0.05 were shown in bold letters.

Figure 13B:
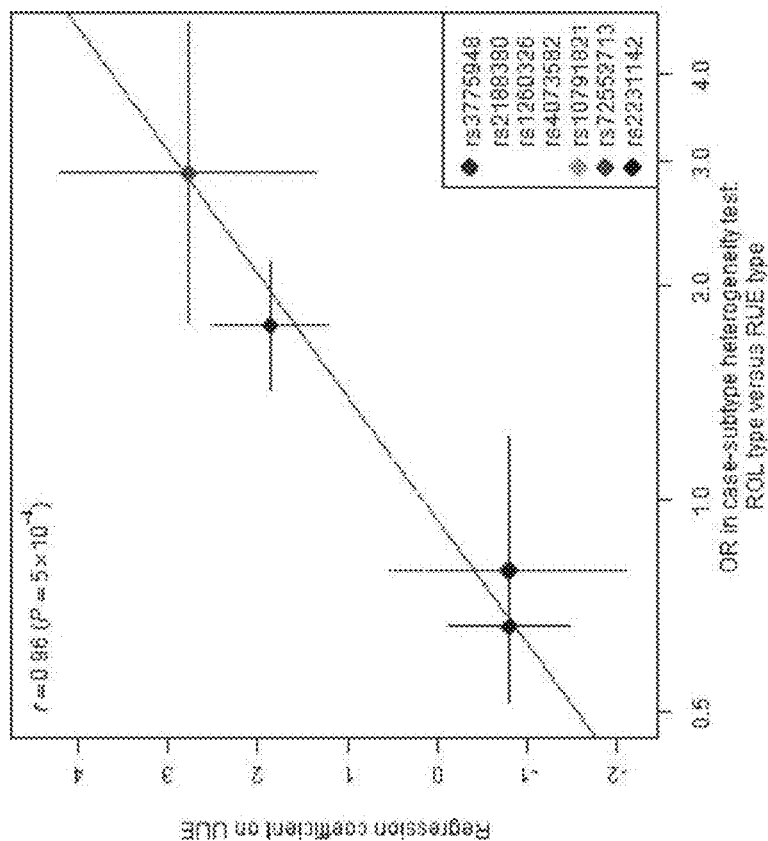
FIGS. 13A and 13B show graphs each showing an influence of risk alleles of the identified SNPs on urate transport-related clinical parameters.
Figure 13A:
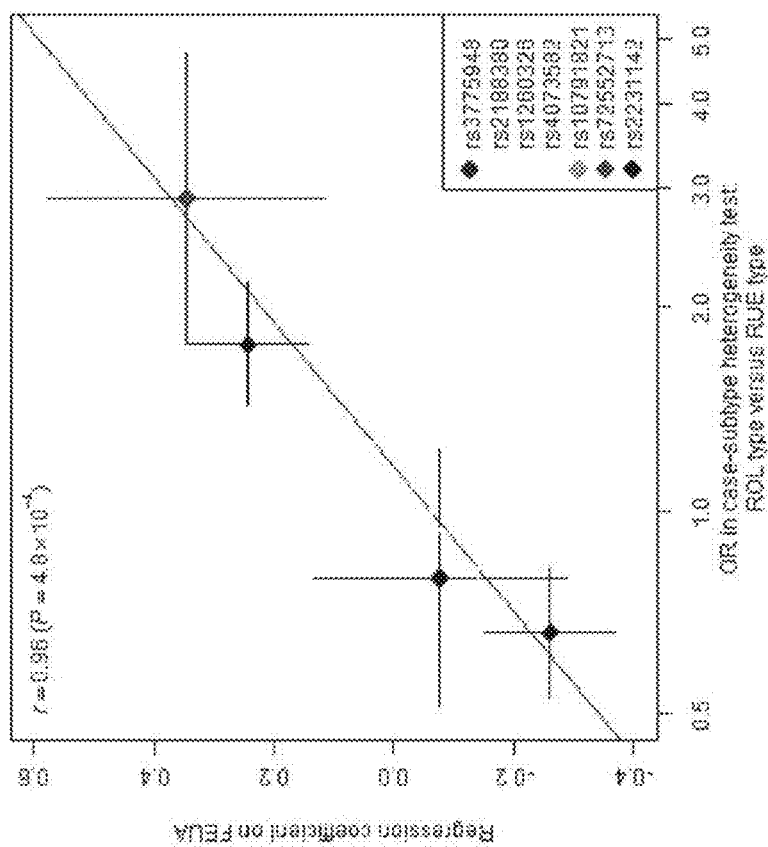

FIGS. 13A and 13B show graphs showing a function of natural logarithm of OR in a case-subtype heterogeneity test, showing the effects of the risk allele of identified SNPs on the clinical parameters of urate transport. (A) shows FEUA, and (B) shows UUE. OR in the case-subtype heterogeneity test represents an estimated value of the ratio of case-subtype OR in the ROL type and the RUE type. OR is a value of more than 1 when SNP has a stronger effect in the ROL type than in the RUE type. Diamonds and straight lines represent point estimated values and 95% CI thereof. Pearson correlation coefficient (r) and significant variance of the coefficient from zero were examined.

Association between SNPs and the urate-transport parameter ($FE_{UA}$ and UUE) was evaluated. Only SNP showing a significant difference in OR between subtypes was significantly associated with these two clinical parameters, risk alleles of the two SNPs of ABCG2 and rs3775948 of SLC2A9 were associated with increase and decrease in $FE_{UA}$ and UUE levels, respectively. When the effect of the risk allele of each SNP with respect to urate-transport parameter was plotted, OR in the case-subtype heterogeneity test (estimation value of the case-control OR with respect to the subtypes) as a function of the natural logarithm, clear straight line relation was shown (r=0.96 [P=$5.0 \times 10^{-4}$] for $FE_{UA}$, and r=0.96 [P=$4.8 \times 10^{-4}$] for UUE).

This result shows that alleles strongly associated with the risk of gout exhibits a differential effect on the urate-transport parameters, and leads to the onset of particular subtype of gout. Furthermore, this result takes extraordinary effects on the urate excretion pathways into consideration. Decrease of $FE_{UA}$ and UUE by the risk allele of SLC2A9 reflects dysfunction of the renal urate excretion pathway. The increase of $FE_{UA}$ and UUE by the risk allele of the two SNPs of ABCG2 observed herein can be explained by the overload effect on renal excretion as compensation of the dysfunction of intestinal excretion pathway due to failure in ABCG2 function. The result is consistent with the findings obtained from ABCG2 knockout mice (Non-Patent Literature 7). Analysis of the gout subtype and the clinical parameters of the urate transport showed the genetic heterogeneity of the gout subtype and continuous distribution in the effective amount. The significant heterogeneity in OR between the subtypes of SNPs of ABCG2 and SLC2A9 having the strongest effect on the gout subtypes and the clinical parameters was detected. Subtype-specific GWAS and a subsequent replication analysis can be useful for identification of genetic factors that are associated with only the particular gout subtype.

When the association of rs671 with gout was analyzed in which adjustment with alcohol drinking was carried out, it is shown that the association of rs671 remains highly significant even after adjustment with alcohol drinking (OR=1.62; P=$6.5 \times 10^{-9}$). This shows the importance of rs671 in evaluation of the risk of the gout.

Figure 14B:
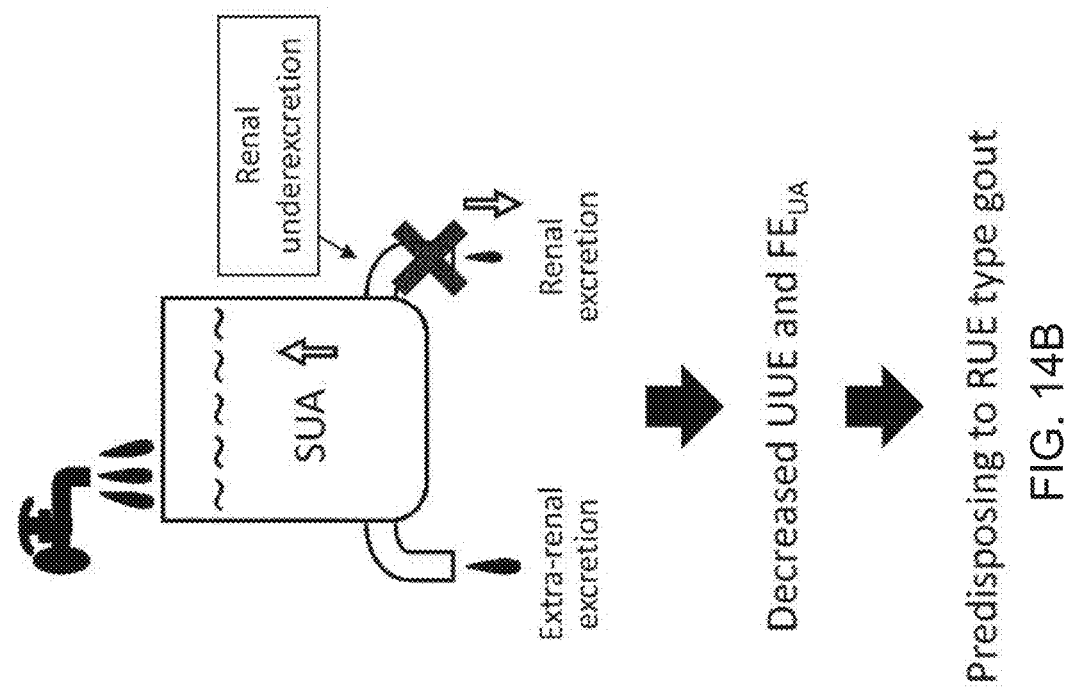
FIGS. 14A and 14B are an explanatory diagram showing an influence of difference in SNPs on the disease types of gout and hyperuricemia.
Figure 14A:
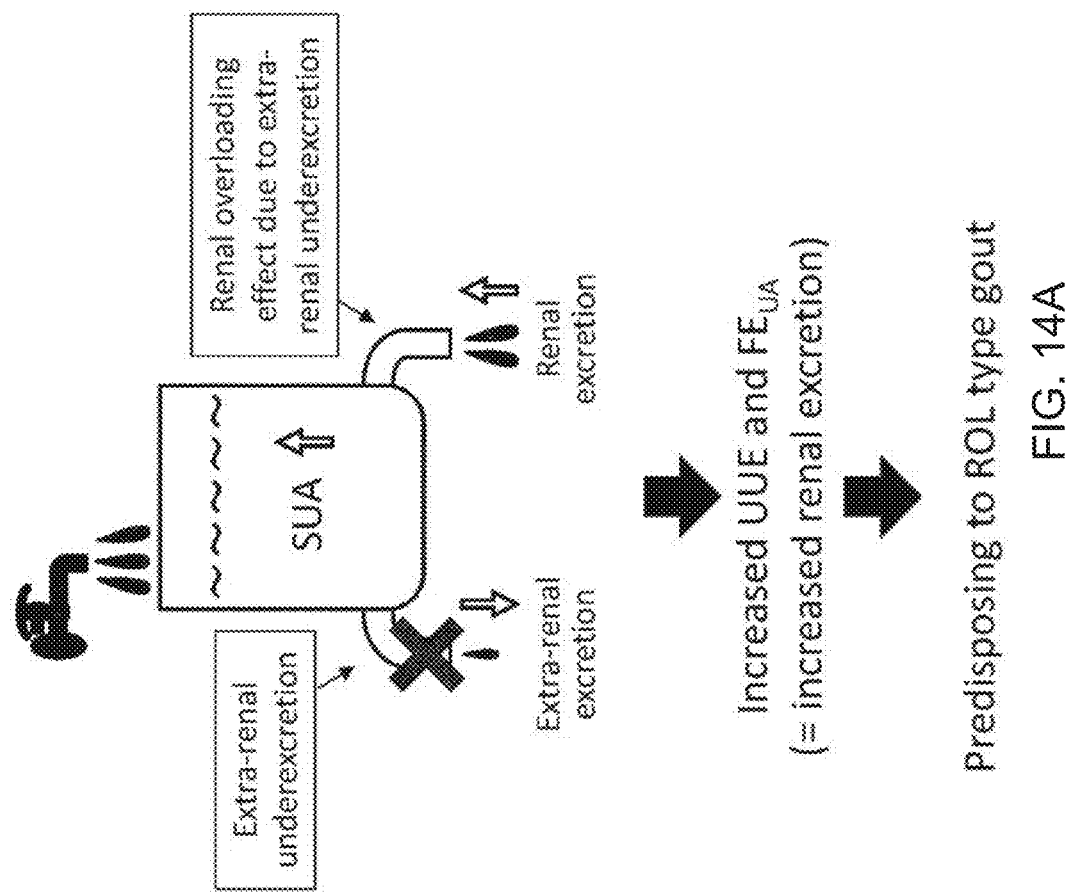
Figure 17:
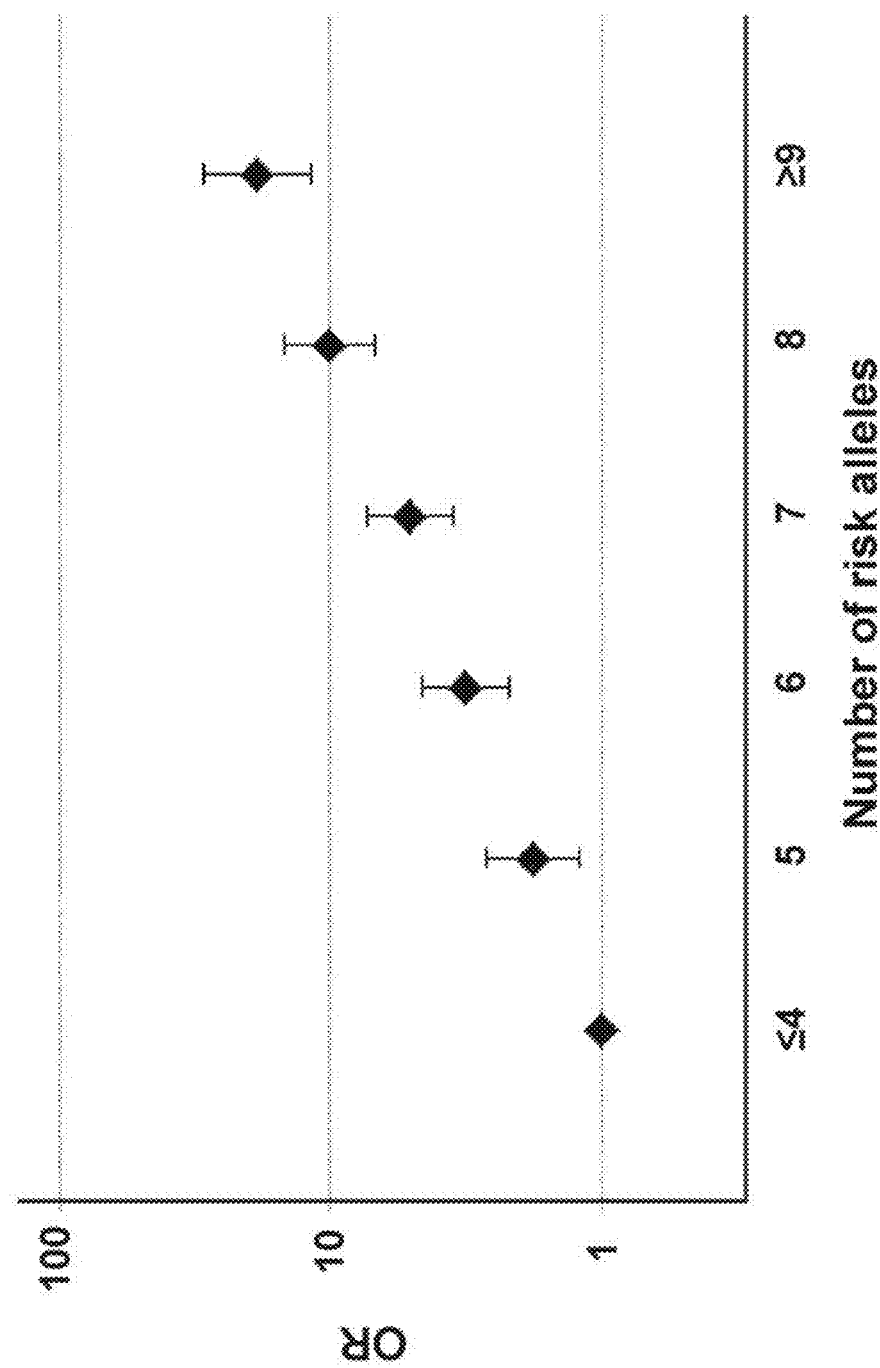
FIG. 17 is a graph showing additive effects of six gout-related SNPs causing the onset of gout.

FIGS. 14A and 14B are an explanatory diagram showing effects of differences in SNPs on the disease types of gout and hyperuricemia; FIGS. 15 and 16 are tables showing the results of analysis of association between gout and tag SNPs of MYL2-CUX2 locus, performed with respect to 1048 male gout patients and 1334 controls, as well as the results of analysis of the effects of tag SNPs by adjustment with rs671; and a table showing analysis results of the association between gout and ALDH2 gene rs671 or alcohol drinking, showing results of analysis performed with respect to 1048 male gout patients and 1323 controls (subjects having information of alcohol drinking), respectively. FIG. 17 is a graph showing additive effects of six gout-related SNPs causing the onset of gout, showing results of analysis performed with respect to 1993 male gout patients and 1334 controls (subjects having information of six SNPs).

The analyses shown in FIGS. 15 and 16 showed significant relationship between gene polymorphism rs671 of ALDH2 gene (alcohol metabolism-related gene) and gout. In particular, FIG. 16 shows that association between rs671 of ALDH2 gene and gout is significant even after adjustment with alcohol drinking.

The analysis shown in FIG. 17 showed that, by counting the number of risk alleles in each sample, and cumulative effects of SNPs (rs72552713, rs2231142, rs671, rs3775948, rs1260326, and rs4073582) at the identified gene loci were evaluated. When reference category was set to 4 or less risk alleles, ORs for gout; to achieve 5, 6, 7, 8, and 9 or more risk alleles were 2.18, 3.83, 6.51, 12.8, and 24.9, respectively.

Figure 18:
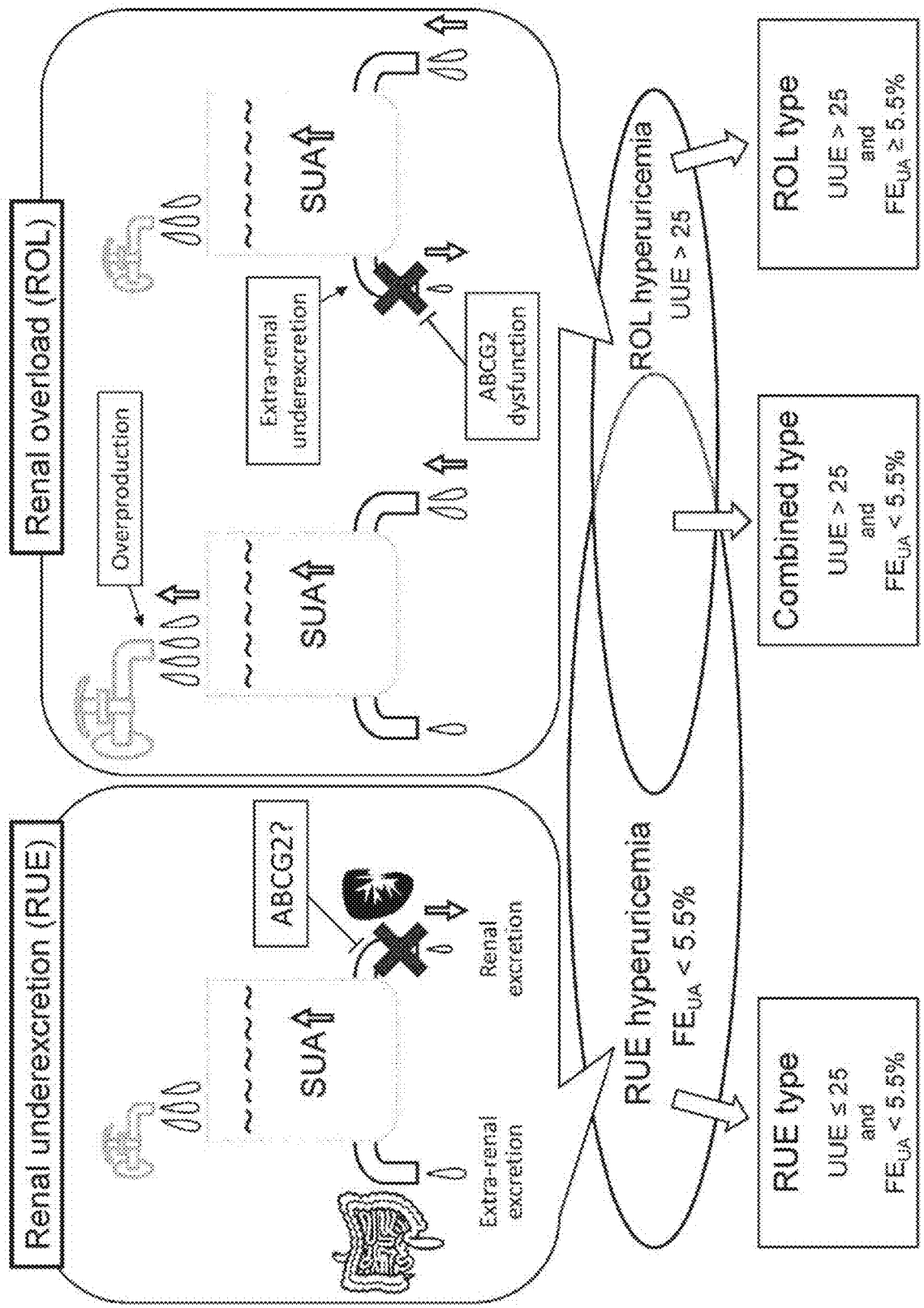
FIG. 18 is an explanatory diagram showing clinical classification of hyperuricemia and gout.
Figure 20:
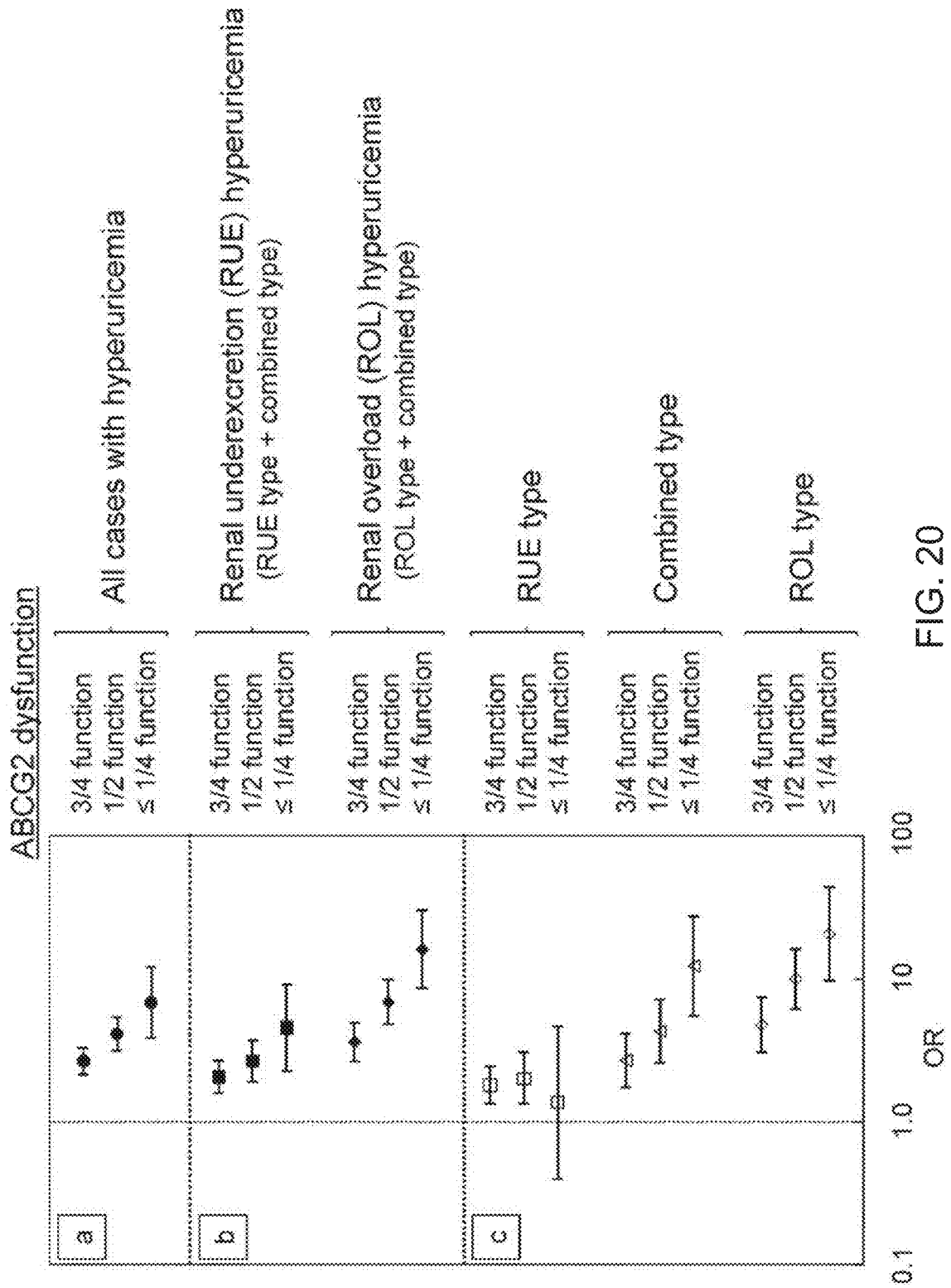
FIG. 20 is an explanatory diagram showing an onset risk by ABCG2 dysfunction in each type of gout.

FIG. 18 is an explanatory diagram showing clinical disease types of hyperuricemia and gout; FIG. 19 is FIGS. 19A and 19B are an explanatory diagram showing haplotype of ABCG2; and FIG. 20 is an explanatory diagram showing an onset risk by ABCG2 dysfunction in each type of gout.

A haplotype of ABCG2 having a Q126X variant was named as "*3". This is a haplotype whose function of ABCG2 becomes zero. A haplotype of ABCG2 having a Q141K variant was named as "*2". This is a haplotype whose function of ABCG2 becomes ½. A haplotype having neither Q126X nor Q141K variant was named as "*1". This is a haplotype whose function of ABCG2 is normal.

Figure 22:
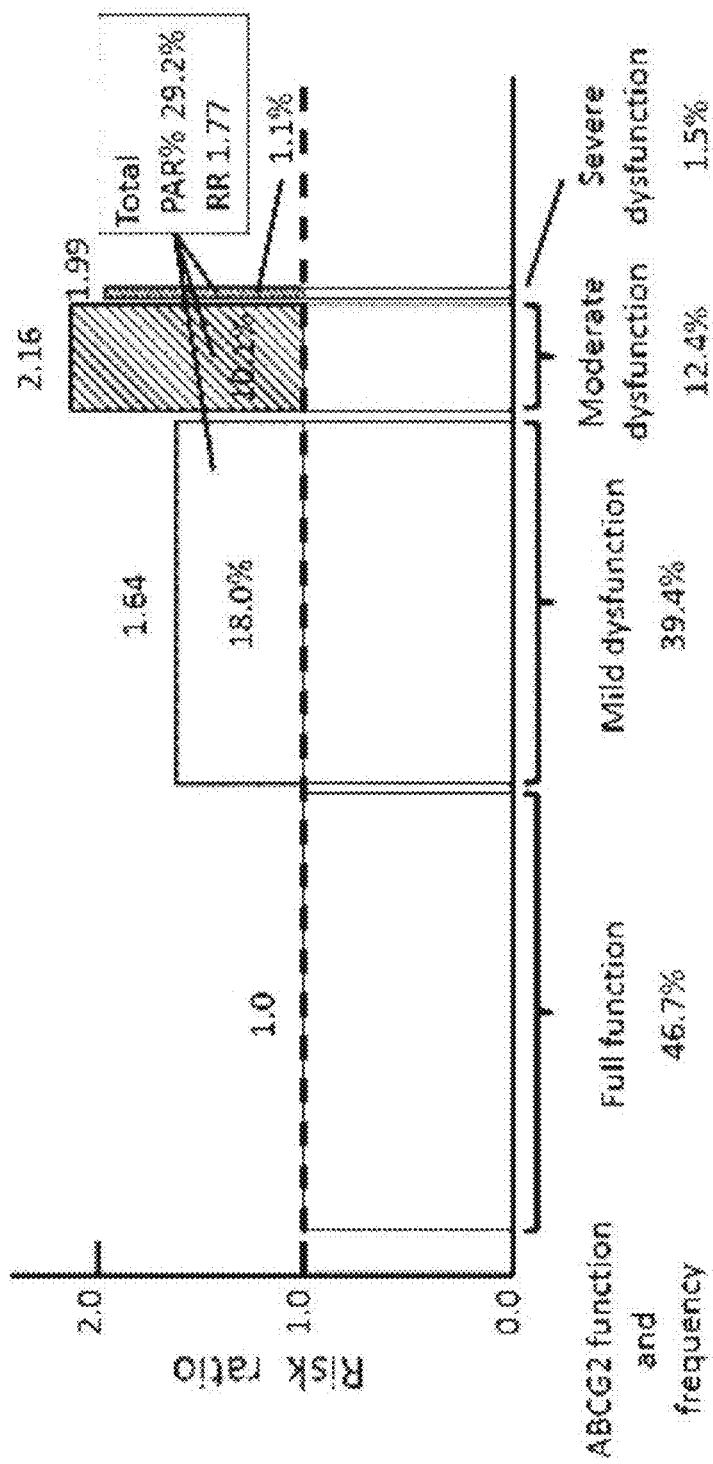
FIG. 22 is an explanatory diagram showing PAR % (Population attributable risk percent) of hyperuricemia by ABCG2 dysfunction.
Figure 24:
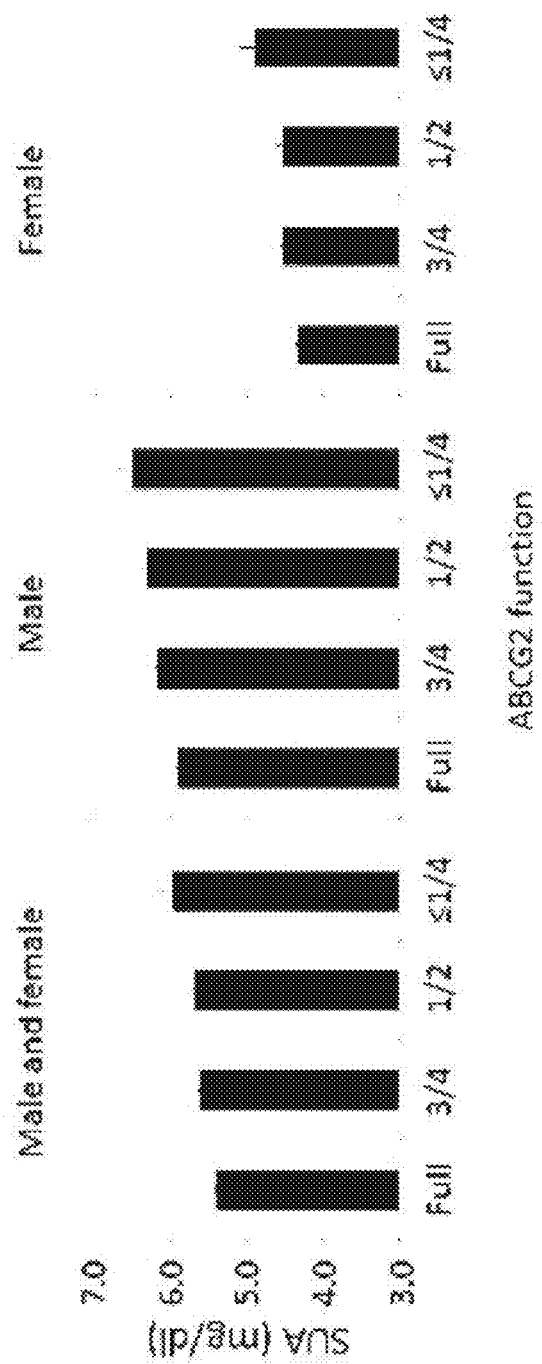
FIG. 24 is a table showing effects of ABCG2 dysfunction, BMI, alcohol intake, and the like, on the serum uric acid level.

FIG. 21 is a table showing frequency of ABCG2 function in 5005 Japanese individuals; FIG. 22 is an explanatory diagram showing PAR % (Population attributable risk proportion percent) of ABCG2 dysfunction for hyperuricemia; FIG. 23 is an explanatory diagram showing the significant increase of serum uric acid level by ABCG2 dysfunction; and FIG. 24 is a table showing effects of ABCG2 dysfunction, BMI, alcohol consumption, and the like, on the serum uric acid levels.

Furthermore, the present inventors disclosed an ABCG2 protein function as a urate transporter in Patent Literature 5, and they additionally have studied a urate excretion mechanism.

Figure 25:
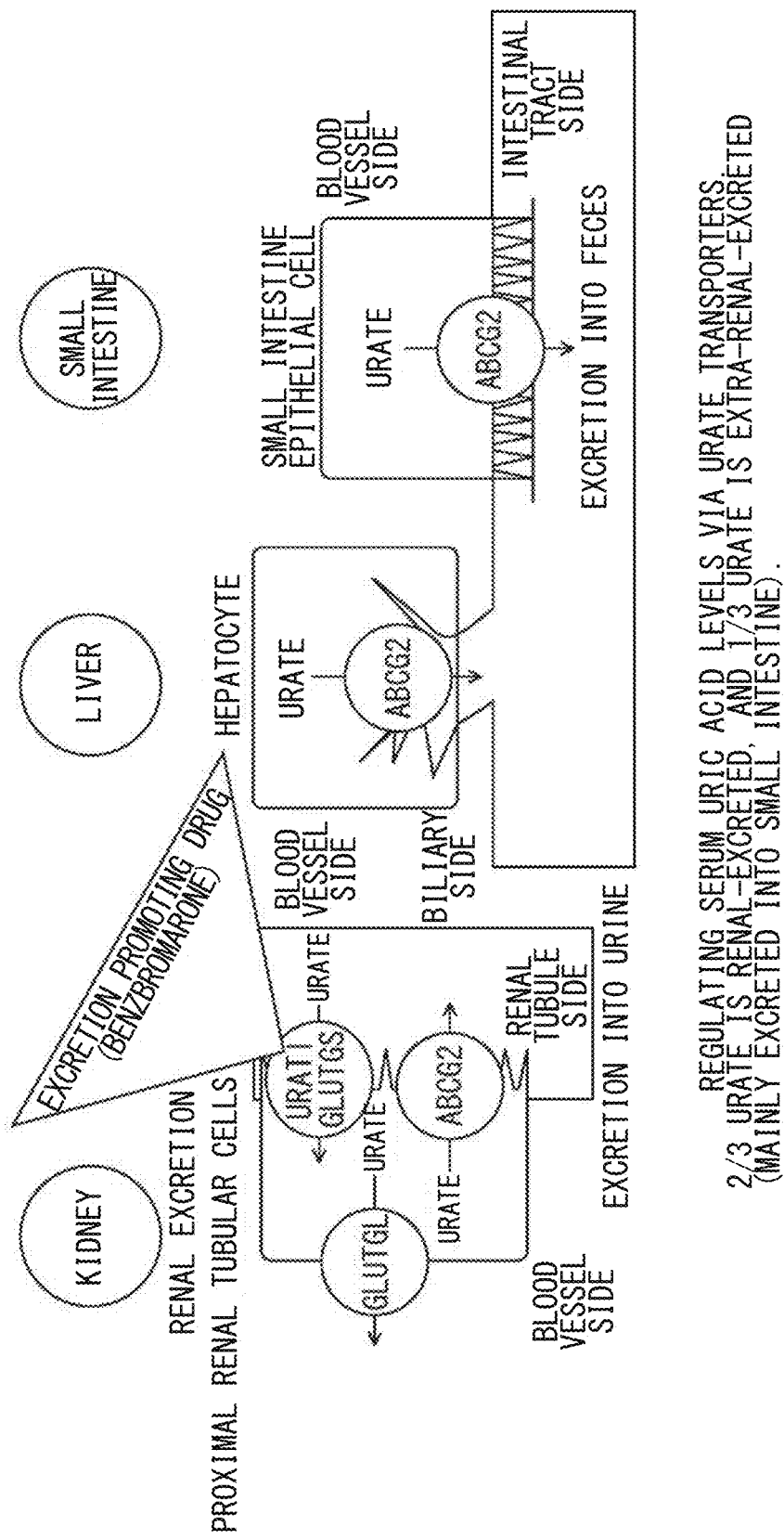
FIG. 25 is an explanatory diagram showing a transport system of urate.
Figure 26:
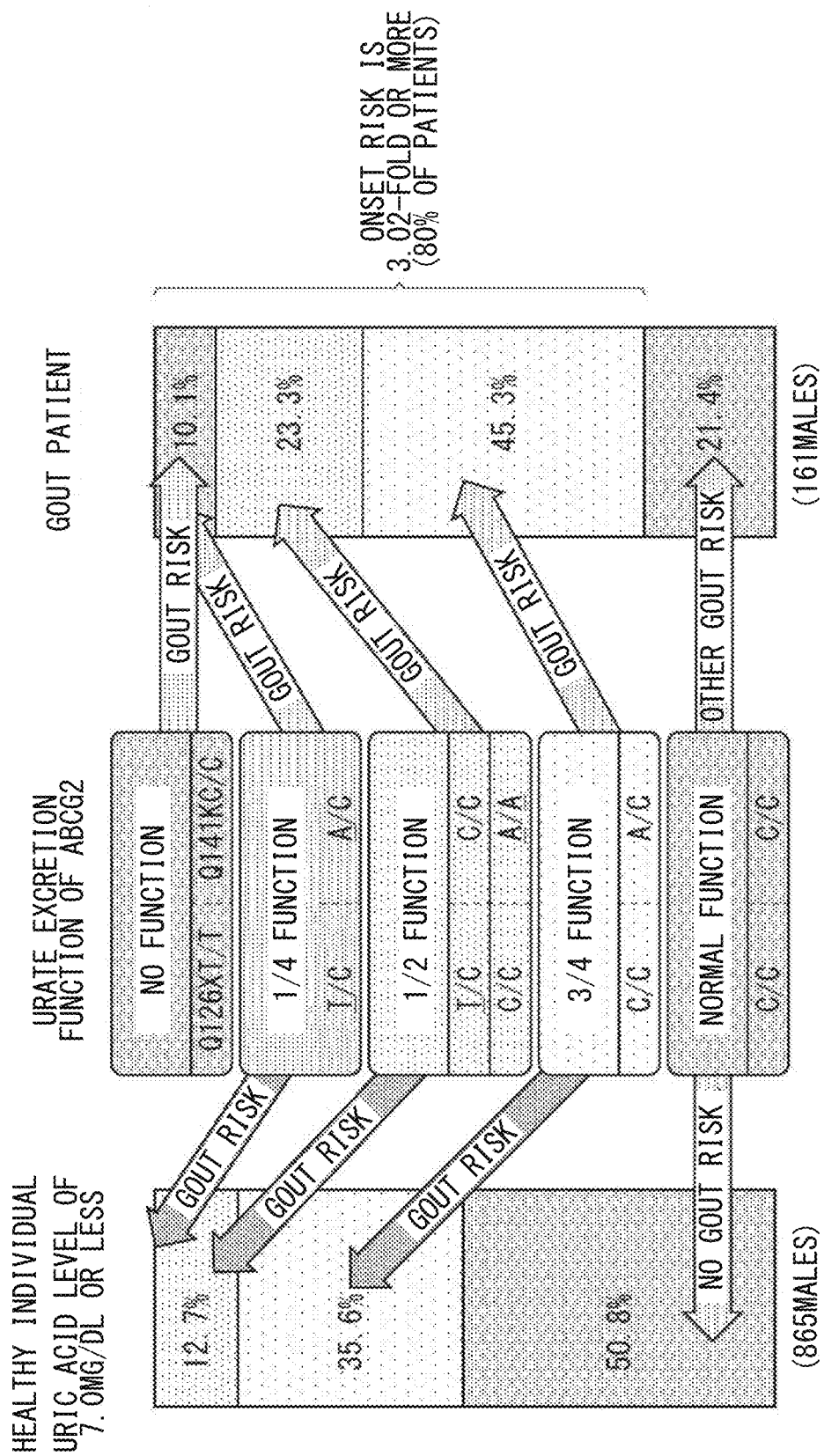
FIG. 26 is an explanatory diagram showing the relationship between ABCG2 dysfunction and the onset risk of gout.
Figure 27:
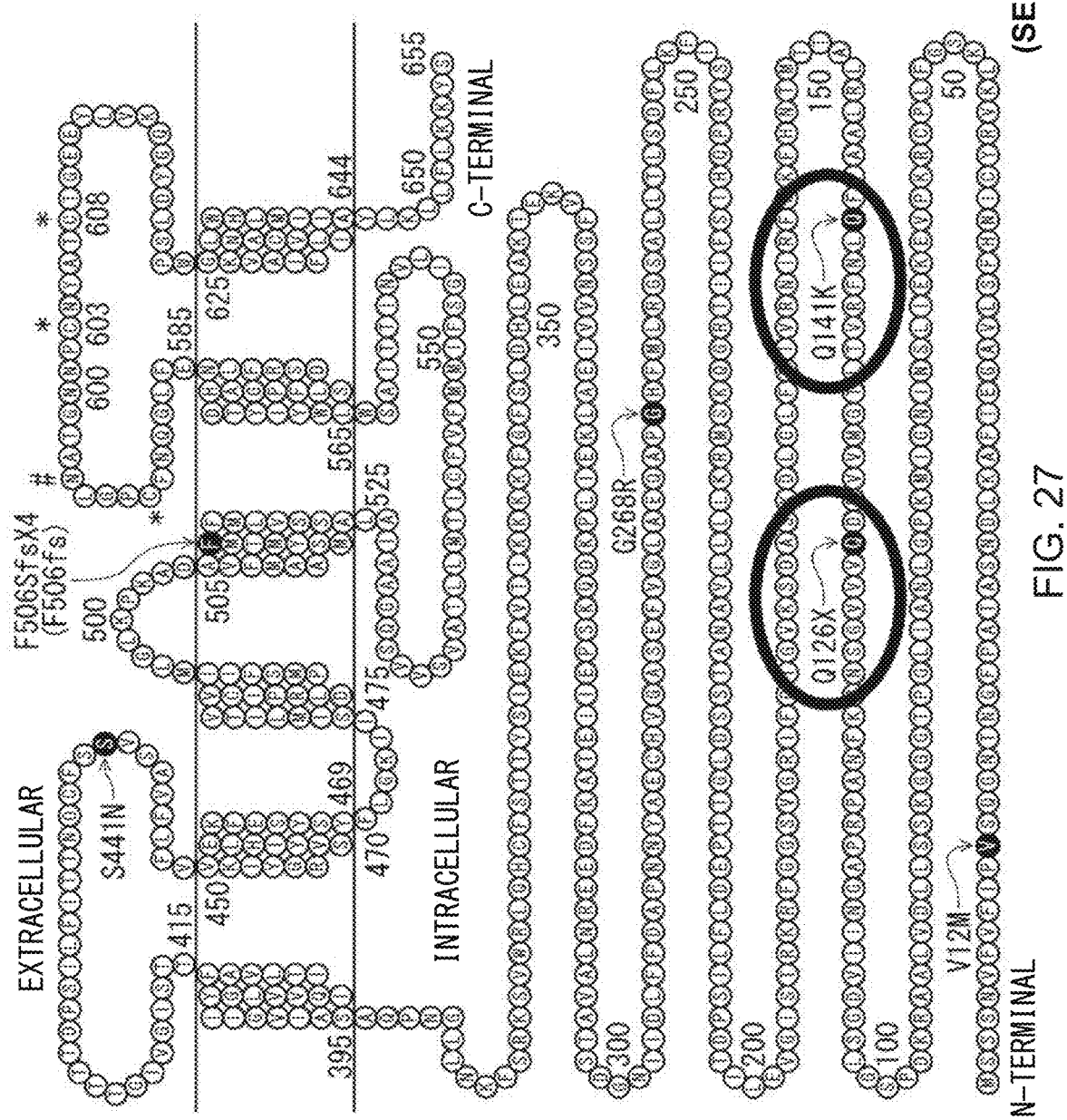
FIG. 27 is an explanatory diagram showing a structure and variations of ABCG2 (SEQ ID NO:1).

FIG. 25 is an explanatory diagram showing a transport mechanism of urate; FIG. 26 is an explanatory diagram showing the relationship between ABCG2 dysfunction and gout risk; and FIG. 27 is an explanatory diagram showing a structure and variations of ABCG2 (Non-Patent Literatures 1 to 2, 8 and 10).

ABCG2 gene variants are observed in 80% of gout patients, but in 50% of healthy individuals. All coding regions of ABCG2 gene of 90 subjects having hyperuricemia were subjected to sequencing, and only six variants with amino acid substitution were found. Three of them show high frequency, and one of them did not cause dysfunction of urate excretion (Non-Patent Literature 8). The most important gene variations are Q126X and Q141K (Patent Literature 5). The Q126X variation was observed in 5.5% of Japanese, and this results in no function. The Q141K variation was observed in as high as 53.6% of Japanese, and this decreases the function to half. When the Q141K variation is present, the amount of proteins to be produced is the same as in the wild type, but transporter expressed on the cell membrane becomes half, thus decreasing the function to half. These two variations do not occur in one chromosome concurrently. Accordingly, by checking whether one variation is present or both variation are present, population risk can be determined in a simple manner. However, if both are normal, there are possibilities that other variants are present.

Figure 28:
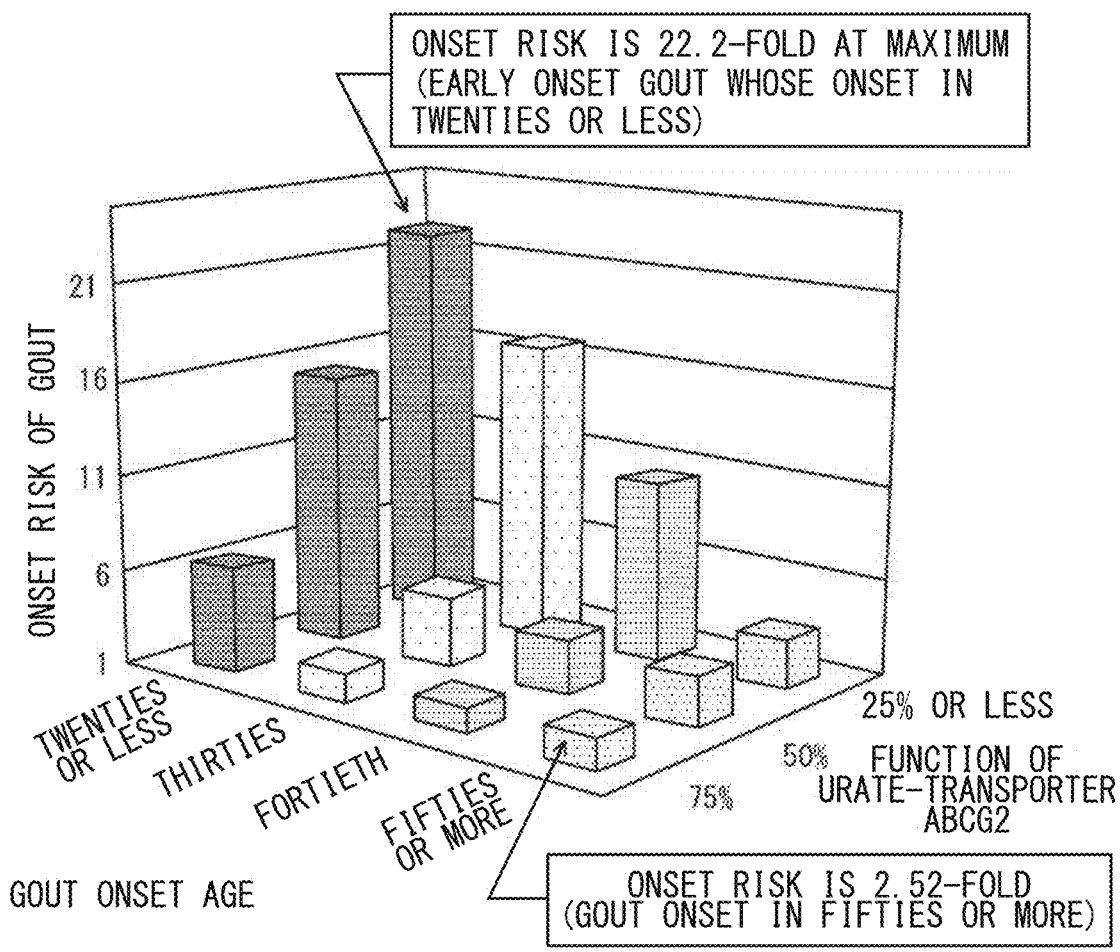
FIG. 28 is an explanatory diagram showing the relationship between function of ABCG2 and the onset risk of gout for each age.

FIG. 28 is an explanatory diagram showing a relationship between ABCG2 function and the onset risk of gout for each age group (Non-Patent Literature 9).

As a result of examination of 705 gout patients, the onset risk of gout is lowest in the fortieth and the onset risk is 2.3-fold in the group in which the ABCG2 function is 75% (i.e., ¾). The onset risk in the fiftieth is 2.5-fold in the group in which ABCG2 function is 75%. In particular, the onset risk in the twenties and younger is exceptionally high. The onset risk of gout becomes as high as 22-fold in the twenties and younger in the group in which the ABCG2 function is 25% (i.e., ¼). In the group in which the function is 25%, the onset risk is extremely high also in the thirties and the fortieth.

In Meiji era, it is said that there was few gout patients in Japan. In that era, when a gene variations are present, the serum uric acid levels are properly increased. Since uric acid also has an antioxidative effect, uric acid that is present at a proper blood level has a good effect on the body. Today, however, hypertrophication and lack of physical activity, together with the risk of gout gene, which is originally present in the background of Japanese, are a major factor of gout. Thus, the number of gout patients is increasing.

Figure 29:
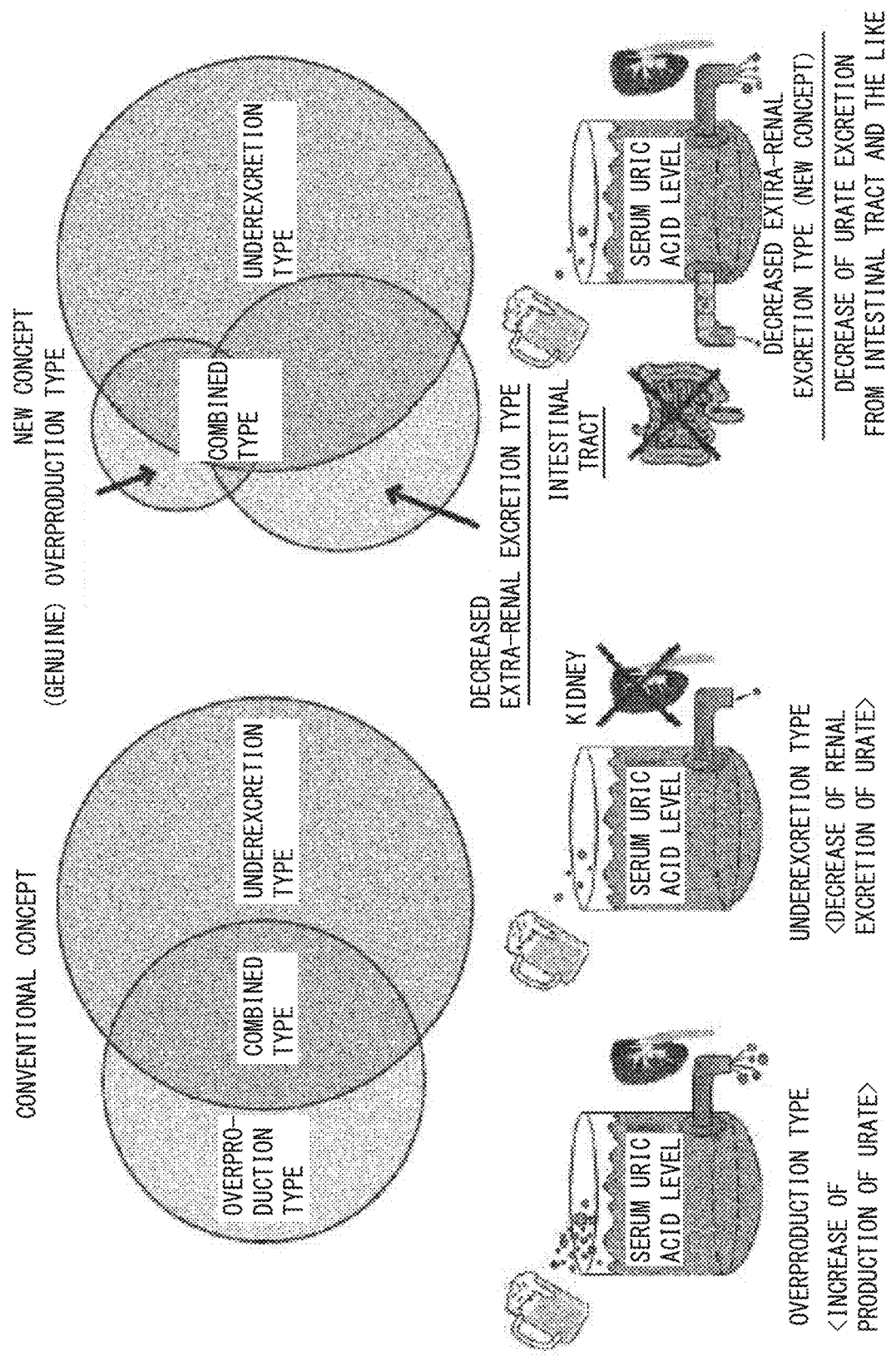
FIG. 29 is an explanatory diagram showing disease type classification of hyperuricemia.

FIG. 29 is an explanatory diagram showing disease type classification of hyperuricemia (Non-Patent Literatures 6 and 10).

It was found that the ABCG2 transporter is expressed also in the kidney and the intestinal tract. Conventionally, the hyperuricemia is classified into two disease types, that is, an "overproduction type" in which production of urate is increased, an "underexcretion type" in which urate excretion from kidney is decreased", and a "combined type" of the above-mentioned two types. Decrease of excretion function due to the ABCG2 gene variations is predicted to result in the "underexcretion type". However, it is shown that an ABCG2 gene variations increase the amount of urate excretion from the kidney (amount of urinary urate excretion) in hyperuricemia cases. A high amount of the urinary urate excretion is diagnosed to be the "overproduction type" or the "combined type" in the conventional disease type classification. However, in an example in which ABCG2 excretion functions decrease to ¼ or less, the "overproduction type" or the "combined type" reaches 90% of hyperuricemia patients. On the other hand, it was shown that ⅔ of urate was excreted from the kidney, and ⅓ of urate was excreted from the intestinal tract.

However, it has been demonstrated, using ABCG2 knockout mice, that when the urate excretion function of ABCG2 was decreased, the serum uric acid levels and the urate excretion amount from the kidney were increased, and on the contrary, the urate excretion amount from the intestinal tract is significantly decreased. Urate excretion to bile was not changed (Non-Patent Literature 6).

From these results, the concept of "extra-renal underexcretion type" hyperuricemia can be advocated as a new disease type of hyperuricemia. Furthermore, the name of "overproduction type" hyperuricemia in the conventional classification including "extra-renal underexcretion type" hyperuricemia and "genuine overproduction type" hyperuricemia can be changed to the name "renal overload type" hyperuricemia.

In selection of drugs, for the "renal overload type" that is the "conventional overproduction type", urate synthesis inhibitory drugs are basically used, and for the "underexcretion type", uricosuric agents are basically used. When the uricosuric agents are used, or when urinary pH is acidic, it is considered that a urine alkalizer may be used in combination from the viewpoint of promoting urate excretion.

Obtaining information of the degree of the gout risk by an ABCG2 genetic test enables early prevention and early intervention of medical care, and start of medication to be considered by the result of the test. According to the present guidelines, medicament therapy is to be started when the serum uric acid level is 8.0 mg/dL, 9.0 mg/dL or more, but before the serum uric acid level becomes such a high value, onset of gout occurs in some individuals. In an ABCG2 gene high-risk group, it is necessary to carry out early intervention to improvement of lifestyle habit and early medication, if necessary.

Hyperuricemia may be involved in not only urate deposition diseases (gout and renal disorders) but also cardiovascular diseases. Thus, the present invention contributes to self-prevention by individuals having high genetic risk, for example, reducing body weight or taking care of diet or exercise, for example, in a case where the individual is obese.

Furthermore, test of the combination of gene polymorphisms enables estimation of clinical disease type and evaluation of recommended treatment policy including drugs to be used to be evaluated.

Furthermore, in Patent Literature 5, the present inventors disclose the case where the variation of genes encoding ABCG2 protein include SNP of at least any one of Q126X, Q141K, G268R, S441N, and F506SfsX. Herein, the present inventors have further studied the ABCG2.

Wild-type human ABCG2 cDNA, which had been inserted into pcDNA3.1(+) vector with a myc tag attached at the N-terminal, was used (Non-Patent Literature 8). Variants of ABCG2 (F208S, P269S, E334X, L447V, S486N, R575X, and C608X) were introduced by the site-directed mutagenesis technique using the myc-ABCG2 wild type/pcDNA3.1 (+) vector as a template.

HEK293 cells were seeded into 12-well plate at $1.5 \times 10^5$ cells/dish. After about 24 hours, the cells were transfected with 0.5 g/dish of the wild type or each variant myc-ABCG2/pcDNA3.1(+) vector. After the cells were cultured for 48 hours, they were collected using a RNA-solve reagent to obtain a reverse transcription product. To perform a quantitative analysis of mRNA, the real-time PCR reaction using the obtained reverse transcription product and SYBR GreenER qPCR SuperMix Universal (Invitrogen) was detected and analyzed with CHROMO4. The mRNA amount of the ABCG2 wild type or each variant was normalized by the mRNA amount of 13 actin.

Expression analysis by the western blotting was carried out, and the cells were immunostained to be visualized and observed by using a confocal microscope. Furthermore, cell membrane vesicles were prepared from HEK293 cells, and subjected to a transport experiment.

FIG. 30 is an explanatory diagram showing positions of seven kinds of amino acid variations of ABCG2. Among the ATP binding sites, Walker A sequence, Walker B sequence, and signature C sequence are shown by a rectangle, respectively. To red circles showing positions of variation, indicators showing the name of variants are added. "#" represents an N-type glycosylation binding site (N596), and "*" represents cysteine residues for disulfide bonds (C592, C603 and C608).

Figure 31A:
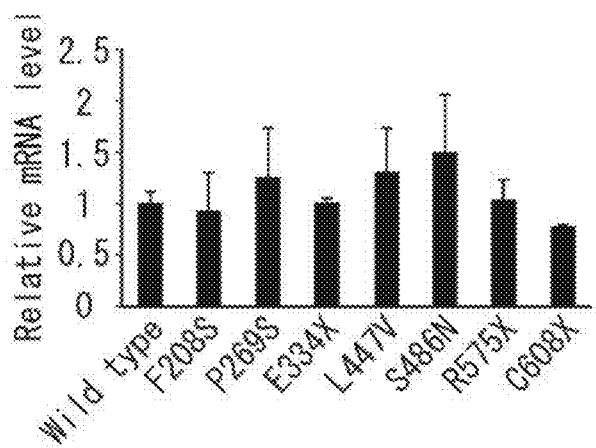
FIGS. 31A through 31C are a graph and western blotting photographs showing quantitation of mRNA and protein of the wild type and variant ABCG2 in HEK293 cells.
Figure 31B:
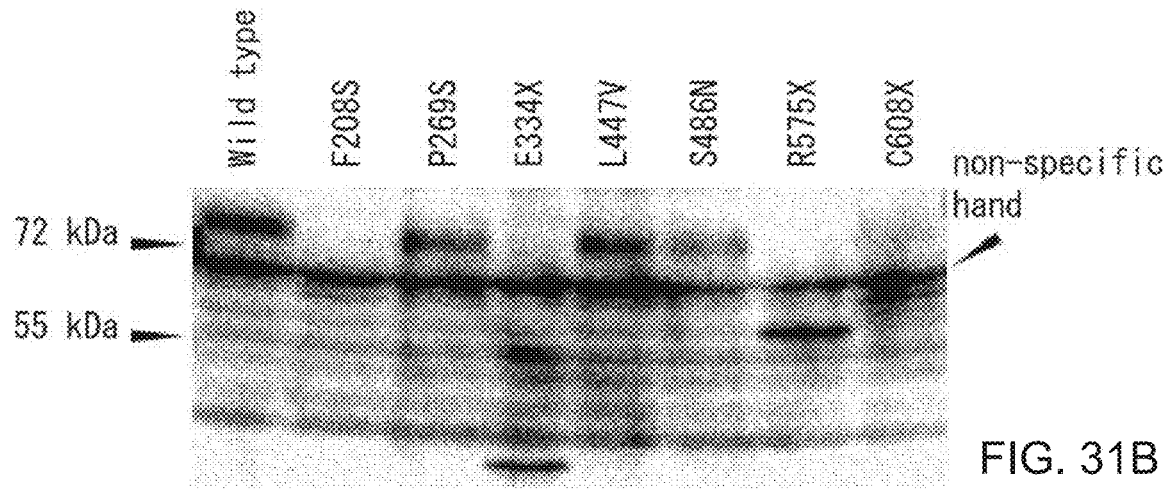
Figure 31C:
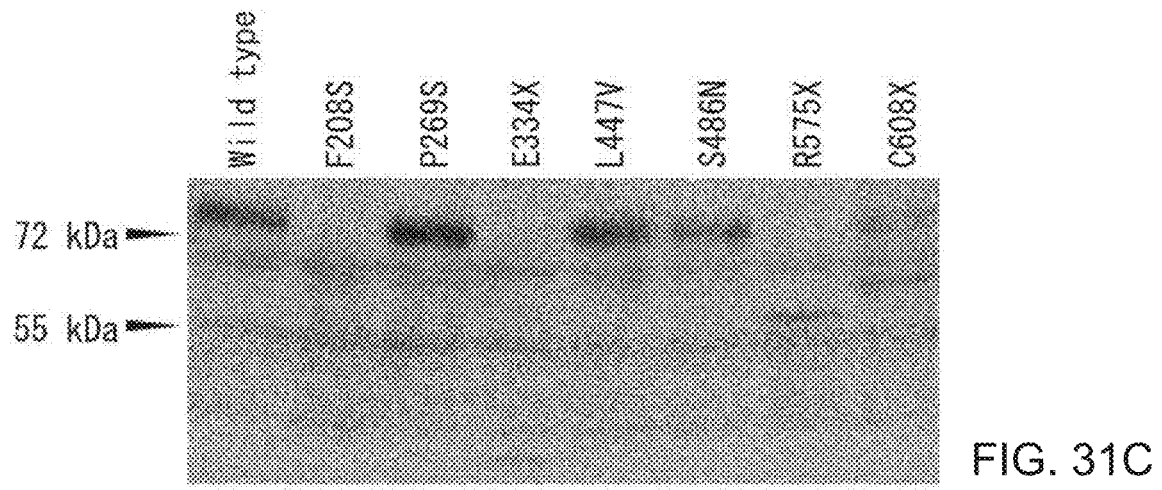

FIGS. 31A through 31C show quantitation of mRNA and protein of the wild type and variant ABCG2 in HEK293 cells. FIG. 31(A) is a graph showing comparison of the mRNA amount when wild type and variant of ABCG2 are transiently introduced into HEK293 cells, FIG. 31(B) is a western blotting photograph showing whole cell lysate, and FIG. 31 (C) is a western blotting photograph showing crude membrane separated from a polyacrylamide gel, transferred to a PVDF membrane, then indicated with an anti-myc antibody, and detected by chemiluminescence.

In order to analyze an effect of each variant of ABCG2 on the expression amount, HEK293 into which myc-ABCG2 expression vectors of wild type and each variant had been transiently introduced, and in which quantitation PCR of mRNA was carried out. As a result, no significant difference in mRNA expression amount was observed between the wild type and each variant.

When western blotting was carried out using a whole cell lysate and a crude product membrane, in wild-type ABCG2, a band was observed in the position of about 80 kDa in the molecular weight. In P269S, L447V, and S486N, a band was detected in the same molecular weight as in the wide type, but the expression amount was decreased to about 60% of that of the wild type in L447V and S486N. On the other hand, in F208S, E334X, and R575X, although there is no significant change in the RNA expression amount, normal expression of protein was not observed. Furthermore, C608X produces a band having a slightly higher molecular weight than that of the wild type, the expression amount of protein was decreased to 20% or less.

Figure 32:
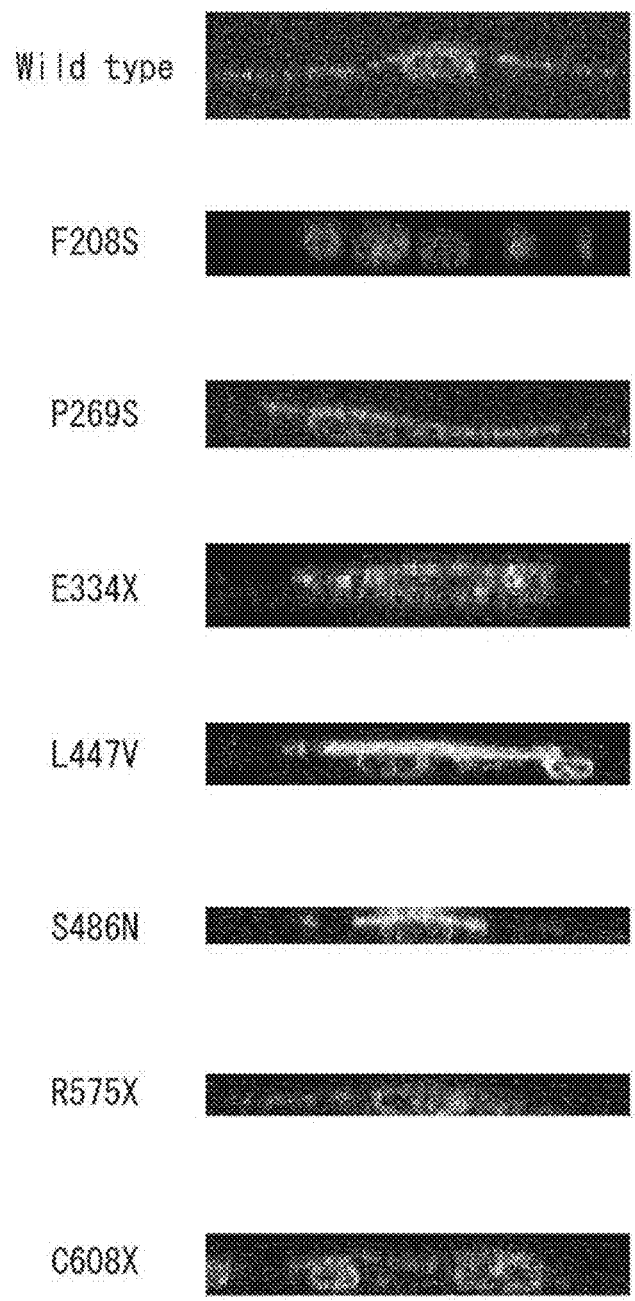
FIG. 32 shows confocal microphotographs showing intracellular localization in the wild type and variant ABCG2 in LLC-PK1 cells.

FIG. 32 shows confocal microphotographs showing intracellular localization in the wild type and variant ABCG2 in LLC-PK1 cells. The wild type and variant myc-ABCG2 were transiently introduced into LLC-PK1 cells. The cells were stained using an anti-myc antibody and TO-PRO3. Green shows ABCG2 and gray shows nucleus.

In order to analyze an influence of each variation of ABCG2 on intracellular localization, the myc-ABCG2 expression vectors of the wild type and each variant were transiently introduced into LLC-PK1 cells, and localization patterns were compared. When the cells were immunostained using an anti-myc antibody and observed by a confocal microscope, it was shown that the wild-type ABCG2 was localized on the apical membrane surface of the LLC-PK1 cells. The results were consistent with the localization in a living body.

As a result of examination of the intracellular localization of ABCG2 of each variant, in P269S, L447V, S486N, and C608X, ABCG2 was observed to be expressed on the apical membrane surface similar to the wild type. On the other hand, in E334X and R575X, ABCG2 was not observed to be expressed on the apical membrane, but observed to be accumulated in the cell. In F208S, as in the western blotting, a signal was not detected.

Figure 33:
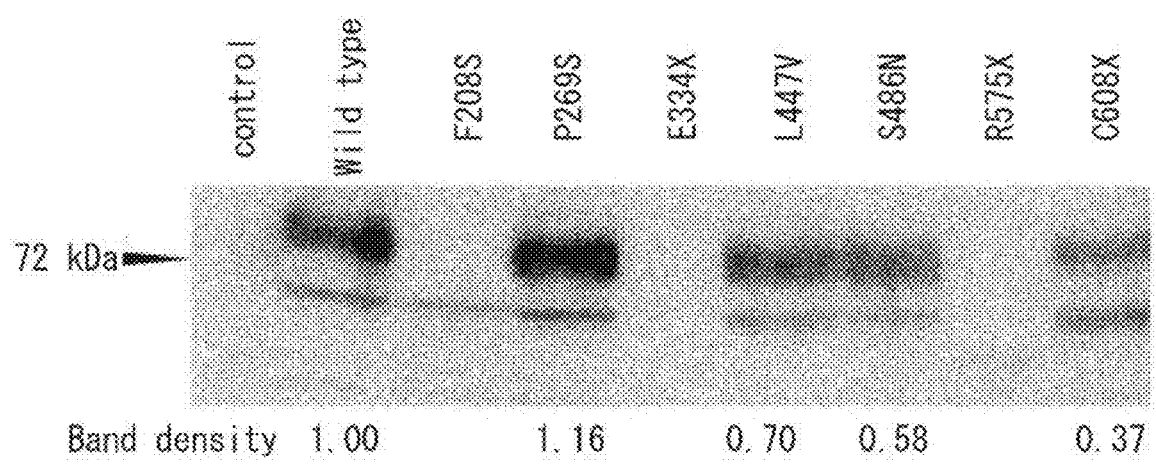
FIG. 33 is a western blotting photograph of protein quantitation using a cell membrane vesicle expressing the wild type and variant ABCG2.

FIG. 33 is a western blotting photograph of protein quantitation using a cell membrane vesicle expressing a wild type and variant ABCG2. Cells membrane vesicle prepared by HEK293 cells expressing a wild type and variant ABCG2 were isolated by polyacrylamide gel, transferred to the PVDF membrane, labeled with an anti-myc antibody, and detected by chemiluminescence. Band density of the myc-ABCG2 in which normal expression was observed was shown.

In order to analyze an influence of each variant of ABCG2 on the urate transport activity, comparison of the transport activity using a cell membrane vesicle was carried out. HEK293 cells into which wild-type and variant myc-ABCG2 expression vectors had been transiently introduced were harvested, and subjected to western blotting using a cell membrane vesicle, the same results as in the crude product membrane were observed. The ABCG2 expression amount per protein in the variant expression vesicle was decreased to 1.16-fold as compared with that of wild type in P269S, 0.70-fold in L447V, 0.58-fold in S486N, and 0.37-fold in C608X, and expression of normal protein was not observed in F208S, E334X, and R575X.

Figure 34A:
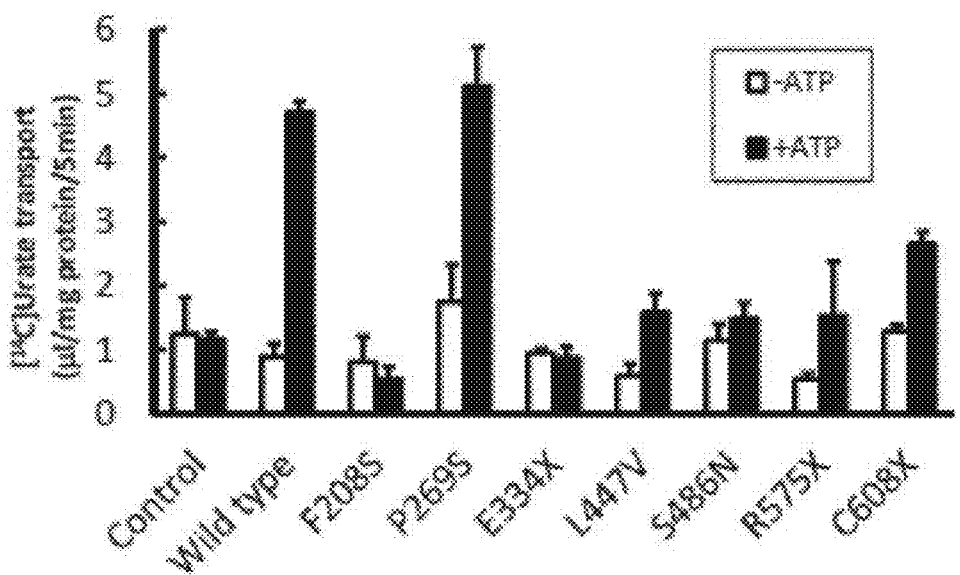
FIGS. 34A and 34B are showing urate transport by an ABCG2 variant.
Figure 34B:
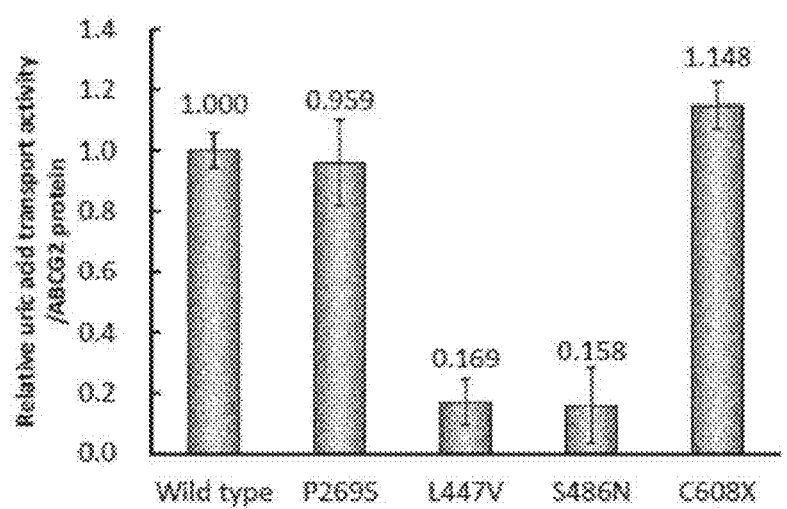

FIGS. 34A and 34B are showing urate transport by an ABCG2 variant. FIG. 34 (A) is a graph showing [14C] urate transport by an ABCG2 variant, and FIG. 34(B) is a graph showing transport activity normalized by ABCG2 protein.

A urate transport experiment was carried out using a cell membrane vesicle prepared by HEK293 cells expressed by wild type and variant ABCG2. As a result, while P269S maintains the same level of urate transport activity as that of the wild type, no urate transport was observed in F208S, E334X, and R575X. In 608X, decrease of the transport ability with the decrease of the expression amount was observed, but the urate transport activity per expression amount of ABCG2 protein was the same level as that of the wild type. Furthermore, in L447V and S486N, although the intracellular localization is normal, the urate transport activity is drastically decreased.

When one gene is a causative gene of a disease, it may be considered that all variations of the gene are counted as a disease risk factor, but in the case of ABCG2, for example, V12M and P269S variations do not have an effect on the urate transport. Therefore, it is not considered that these variations have an effect on the onset risk of gout. In analysis of genes for the purpose of risk prediction of the onset risk of hyperuricemia and gout, such variations may not be considered as a factor that brings the risk increase. On the other hand, since variations other than the two variations have an effect on the urate transport function, similar to Q126X and Q141K, it is considered that such variations increase the onset risk of hyperuricemia and gout.

F208S expressed mRNA, but expression of protein was not observed, and the urate transport function was not observed. Since E334X and R575X are nonsense variations and do not express normal protein, it is natural that they do not have a transport function. However, although C608X is a nonsense variation, it maintained a part of the transport function. This is thought to be partially because C608X has termination codons after six transmembrane sites. Furthermore, the western blotting band of C608X is shifted to slightly higher molecular weight side as compared with the wild type. This is suggested that a three-dimensional structure that is different from the wild type is formed because C608 that is suggested to be important for formation of the disulfide bond is deleted.

According to the result of immunostaining in vitro, in L447V and S486N, intracellular localization was observed at the brush border membrane side similarly to the wild type, and the protein expression amount was not so decreased as compared with that of the wild type, but urate transport is hardly detected.

FIG. 35 is a table showing polymorphism and variation of ABCG2, which were analyzed in the above-mentioned analysis and analysis in Non-Patent Literature 6.

An effect of 13 types of variations and polymorphisms of ABCG2, in which amino acid is substituted, on the urate transport function was evaluated. R575X is already known (Non-Patent Literature 11). However, it is the first time to analyze its function by the present invention. F208S, P269S, and E334X were analyzed in terms of function of the substrate such as methotrexate (Non-Patent Literatures 11 to 14), resulting in that the change in the urate transport activity seems to be the same as in the change in the transport activity with respect to the other substrate. L447V, S486N, and C608X are novel variations. These variations were found as a result of analysis of specific population, that is, population of human having hyperuricemia, gout, or the like, and therefore, variations of ABCG2 gene are likely to be accumulated in such population. The results reflect the strength of the relationship between the ABCG2 gene and hyperuricemia, gout, or the like.

The present inventors have further investigated NPT1.

FIG. 36 is a table showing the results of analysis of the relationship between gout and a gene polymorphism rs1165196 of NPT1/SLC17A1.

Gene polymorphism (SNP) (rs1165196, 1269T) of NPT1/SLC17A1 was analyzed in 545 male gout patients and 1115 male subjects having normal uric acid levels. As a result, in gout with renal urate underexcretion (RUE gout) ($FE_{UA}$ of less than 5.5%), it was found that the variation (rs1165196, 1269T) of NPT1/SLC17A1 significantly decreases the risk of gout. Odds ratio was 0.73-fold (95% confidence interval: 0.54 to 0.97, P-value: 0.031).

Furthermore, the immunohistochemical analysis shows that NPT1 is expressed at the apical side of the proximal tubules of human kidney. Furthermore, in also function analysis using living cells in which NPT1 was expressed in Xenopus laevis oocytes, it was found that I269T enhanced the urate excretion function as compared with the wild type. Thus, it was shown that I269T was a gain-of-function type variation, promotes the urate excretion by NPT1, and supports to decreases the-risk of gout.

From this analysis, in all the gout (All gout) and gout in which renal urate underexcretion is not observed (Non-RUE gout) ($FE_{UA}$: 5.5% or more), significant differences were not observed in the onset risk of gout. However, it was found that in the other analysis with number of samples increased, a gene polymorphism (SNP) (rs1165196, I269T) of NPT1/SLC17A1 also significantly decreases the risk of all the gout (All gout).

Figure 37:
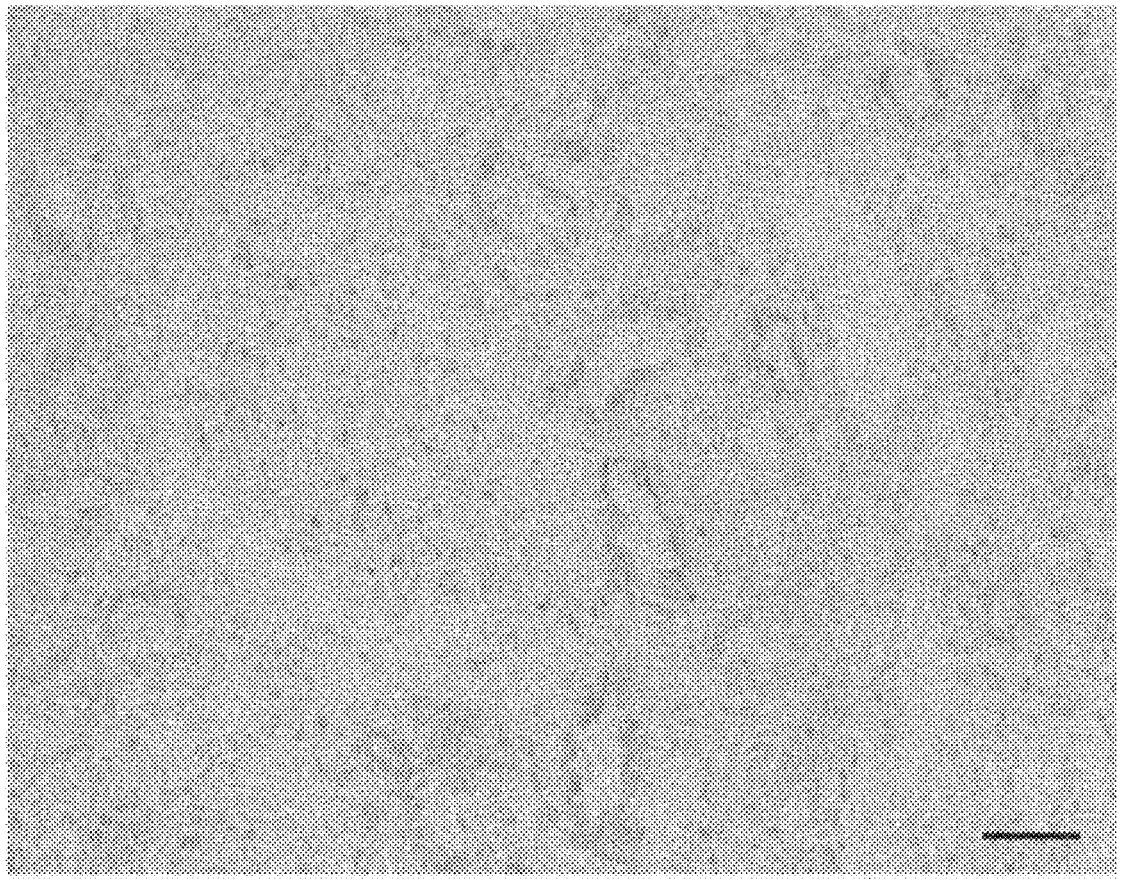
FIG. 37 is a photograph showing localization of NPT1 in human kidney by immunohistochemical staining.

FIG. 37 is a photograph showing localization of NPT1 in human kidney by immunohistochemistry.

With an anti-human NPT1 antibody (SANTA CRUZ, Santa Cruz, Calif., USA) (diluted at 1:500) produced from rabbit, tissue sections of human kidney were incubated overnight at 4° C. and treated with an anti-rabbit peroxidase-labelled polymer (Envision+: Dako, Tokyo, Japan) for 30 min, and immunoreactions were detected by staining with diaminobenzidine (0.8 mM). A bar in the photograph is 50 μm.

As a result, it was clarified that NPT1 was localized at the apical side in the proximal tubules in the human kidney.

Figure 38:
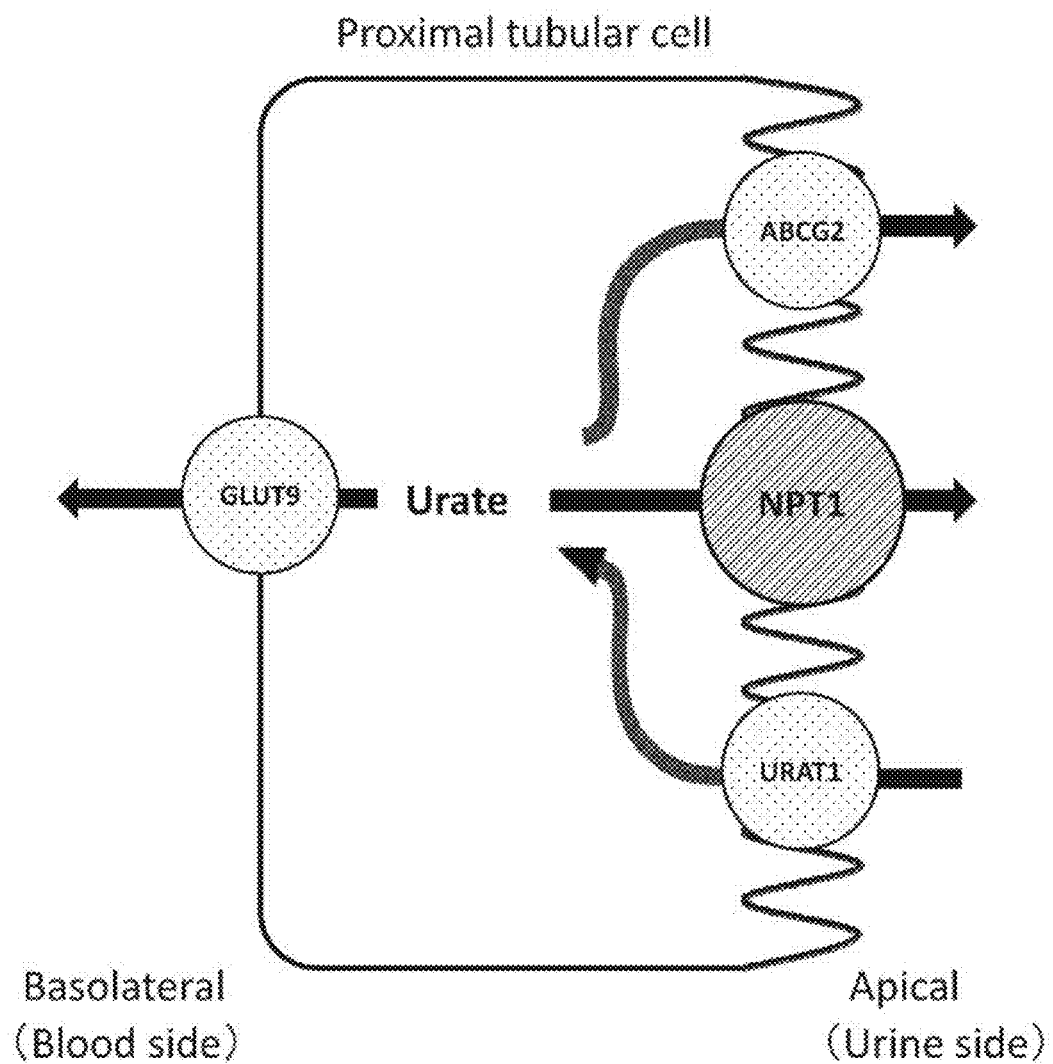
FIG. 38 is a diagram showing a physiological function of NPT1.

FIG. 38 is a diagram showing a physiological function of NPT1.

NPT1 mediates the excretion of urate into urine at the apical side of the proximal tubules in human kidney, and acts to decrease the serum uric acid level so as to play an important physiological role in regulation of serum uric acid levels.

Furthermore, I269T that is a gain-of-function type (gain-of-function type) variation of NPT1 acts so as to promote urate excretion into urine (resulting in increasing $FE_{UA}$), and decreases the serum uric acid levels. Therefore, it was pathologically clarified that the variation significantly decreases the risk of gout.

Furthermore, QTL analysis of serum uric acid levels for rs56027330 (G279R) of NPT4/SLC17A3 in 5017 male and female Japanese individuals was carried out. As a result of correction based on sex, BMI, ABCG2 function, and NPT1/SLC17A1 (rs1165196; I269T), G279R of NPT4 showed significant (P=0.03) relationship with respect to the serum uric acid levels. Thus, the relationship between the rare gene polymorphism of NPT4 and the serum uric acid levels was demonstrated for the first time, and it was suggested that NPT4 was likely to be associated with uric acid-related diseases including gout and hyperuricemia or inflammatory diseases related thereto.

Figure 39:
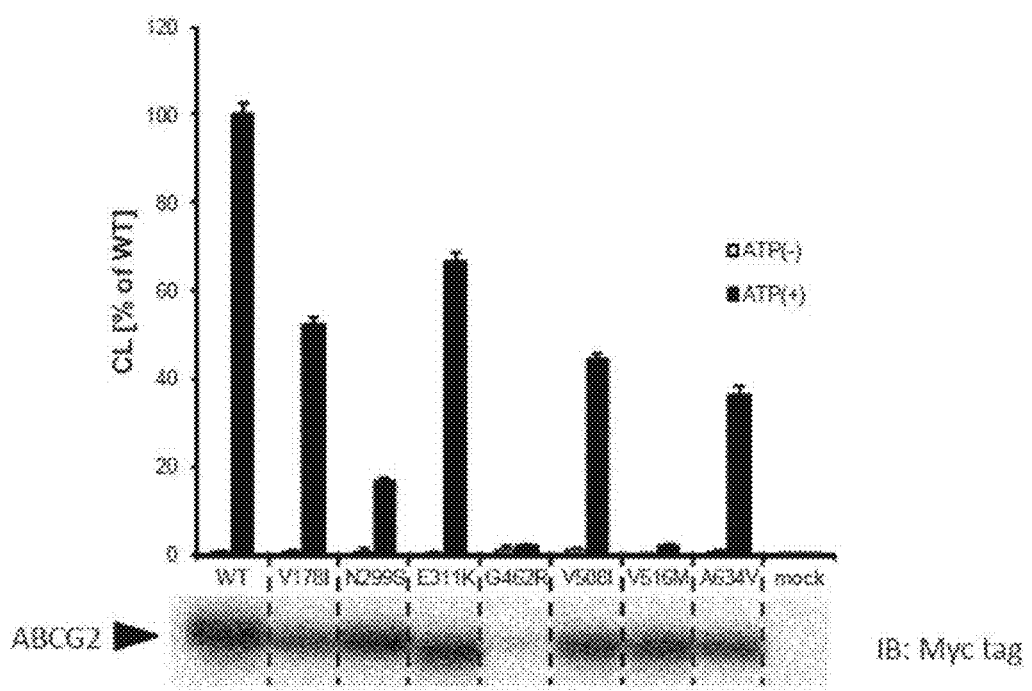
FIG. 39 shows a graph and a western blotting photograph showing the results of urate transport analysis of mutated ABCG2.

FIG. 39 shows a graph and a western blotting photograph showing results of urate transport analysis of mutated ABCG2.

In order to clarify an effect of the urate transport activity on the ABCG2 function, using membrane vesicles expressing the wild type and variant ABCG2 protein, urate transport activities of seven types of variants were examined. ATP-dependent urate transport was remarkably decreased in V178I, N299S, E311K, V508I, and A634V, and was nearly eliminated in G462R and V516M. Western blot analysis showed that the expression amount of ABCG2 protein on the membrane vesicles was not so different among V178I, N299S, E311K, V508I, V516M, and A634V, but was remarkably decreased in G462R.

Figure 40A:
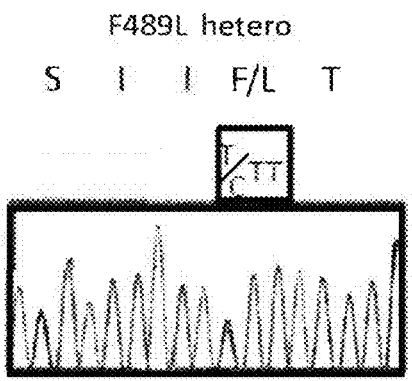
FIGS. 40A and 40B are graphs showing nonsynonymous variants of the ABCG2 gene found in the sequence analysis of gout cases, namely residues 486-490 of SEQ ID NO:1 having a substitution at residue 489, and residues 618-263 of SEQ ID NO:1 having a substitution at residue 620, respectively.
Figure 40B:
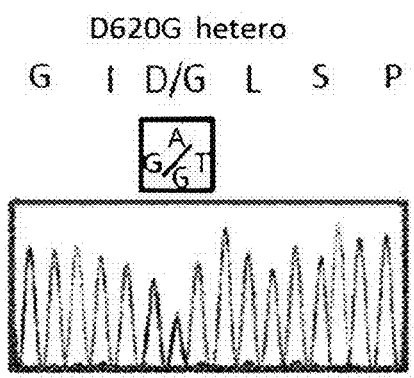

FIGS. 40A and 40B are graphs showing nonsynonymous variants of the ABCG2 gene found in the sequence analysis of gout cases. FIG. 40 (A) is a graph showing the result of F489L (exon 12), one of nonsynonymous variants of ABCG2 gene, found in the sequence analysis of gout cases, and FIG. 40 (B) is a graph showing the result of D620G (exon 16), one of nonsynonymous variants of ABCG2 gene, found in the sequence analysis of gout cases.

In order to examine the nonsynonymous variants of ABCG2 gene, in 500 gout cases, the exon of ABCG2 gene was sequenced. As a result, as the other nonsynonymous mutation, F489L (exon 12) and D620G (exon 16) were identified.

FIGS. 41A and 41B are a table showing the results of analysis of the relationship between hyperuricemia and URAT1 nonsynonymous variants. FIG. 41 (A) is a table showing the results of analysis of the association between hyperuricemia and URAT1 nonsynonymous variants; and FIG. 41 (B) is a table showing the results of analysis (with adjustment by Q126X and Q141K variations) of the relationship between hyperuricemia and URAT1 nonsynonymous variants.

The subjects include 2209 male patients with hyperuricemia and 1388 controls. A significant relationship between rare polymorphisms W258X and R90H of URAT1 gene (urate reabsorption transporter gene) and gout was observed.

FIG. 42 is a table showing the results of genome-wide association study of gout followed by replication analysis using a custom chip.

When a meta-analysis was carried out based on the analysis results of the primary analysis (GWAS, 945 clinically diagnosed gout cases, and 1213 controls) and the secondary analysis (replication study using a custom chip, 1048 clinically diagnosed gout and 1334 controls), a significant relationship was observed in a gene polymorphism (SNP) (rs2285340) of NRXN2-SLC22A12/URAT1, a gene polymorphism (SNP) (rs 1165196) of SLC17A1/NPT1, a gene polymorphism (SNP) (rs11758351) of HIST1H2BF/HIST1H4E, and a gene polymorphism (SNP) (rs4496782) of HIST1H2BE/HIST1H4D. Furthermore, other than the above, FAM35A (rs7903456, Chromosome 10) showed a significant relationship with renal underexcretion gout (RUE gout) by the replication analysis.

FIG. 43 is a table showing the results of analysis of the change of urinary coproporphyrin based on the function of ABCG2.

The subjects include 509 examinees of health examination. Urinary coproporphyrin as one type of a porphyrin body was analyzed by a value corrected using urine creatinine (μg/gCrea). ABCG2 is known to transport not only urate but also porphyrin, and ABCG2 was found to be associated with porphyrin. Furthermore, when cases of Q126X homozygote of ABCG2 (ABCG2 function: 0%) was analyzed, urinary coproporphyrin was 16 µg/gCrea. The result was consistent with the results shown in FIG. 43. Furthermore, protoporphyrin in whole blood was 92.5 µg/dl (normal value: 40 µg/dl or less), and apparently increased from the normal value. These findings show that ABCG2 dysfunction increases porphyrin in human cells, and suggest that it is associated with pathologic conditions such as photosensitivity.

FIG. 44 is a table showing the results of analysis of the relationship between the function of ABCG2 and cerebral stroke.

A significant association was observed between the gene polymorphisms of ABCG2 and cerebral stroke as an inflammatory disease.

Furthermore, ABCG2 may be involved in inflammatory diseases via the effect on high-capacity urate transport of urate or the like. Also in atrial fibrillation, a kind of arrhythmia, it is reported that inflammation is involved in its pathologic conditions (Non-Patent Literatures 15 to 16). According to the analysis by the present inventors, 20 subjects having previous atrial fibrillation were extracted from 4999 subjects of health examination, the distribution of the ABCG2 functions in the 20 subjects showed significant difference (P=0.01) from that of the subjects not with atrial fibrillation. The analysis suggests that ABCG2 dysfunction is related to pathologic conditions of atrial fibrillation.

FIG. 45 is a table showing the results of analysis of the serum uric acid levels in ulcerative colitis cases based on the function of ABCG2.

In ulcerative colitis cases, ABCG2 dysfunction tends to increase serum uric acid levels (SUA).

FIG. 46 is a table showing the results of analysis of the serum uric acid levels before treatment in viral enteritis cases based on the function of ABCG2.

A significant association was observed between the ABCG2 function in patients with viral enteritis disease as viral intestinal disease and the increase in the uric acid levels before treatment. Furthermore, the uric acid levels before treatment significantly increased as the ABCG2 function decreased. An average value of the convalescent serum uric acid levels was 4.85±0.26 mg/dl, and remarkably increased before treatment. Subjects include 58 subjects with pediatric viral enteritis (30 male subjects and 28 female subjects).

FIGS. 47A and 47B are a table showing the results of analysis of the relationship between function of ABCG2 and ages at which dialysis is introduced and the serum uric acid levels in hemodialysis cases. FIG. 47 (A) is a table showing the results of analysis based on the ABCG2 function and the age at which hemodialysis is introduced in hemodialysis cases. FIG. 47 (B) is a table showing the results of analysis of the ABCG2 function and the serum uric acid levels in hemodialysis cases.

When the relationship between the ages at which hemodialysis is introduced and the ABCG2 function with respect to subjects including 139 hemodialysis cases (101 male subjects and 38 female subjects), it was found that a variations of ABCG2 made the ages at which hemodialysis is introduced earlier. Furthermore, when the relationship between the serum uric acid levels and the ABCG2 function was examined in 106 cases (73 male subjects and 33 female subjects) without oral administration of therapeutic agents for gout and hyperuricemia, it was found that the ABCG2 variations increased the serum uric acid levels extremely significantly.

Figure 48A:
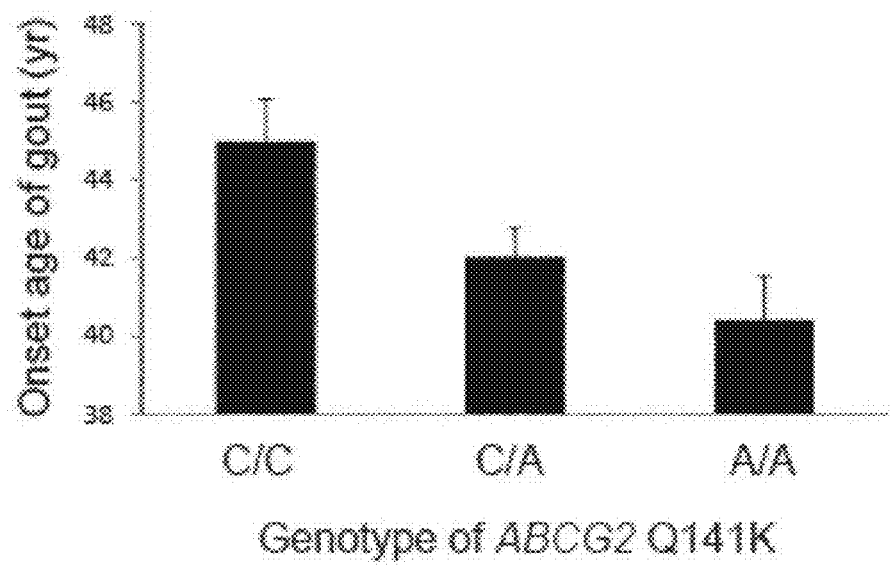
FIGS. 48A and 48B show the results of analysis of the relationship between the function of ABCG2 and the onset age of gout and Parkinson's disease.
Figure 48B:
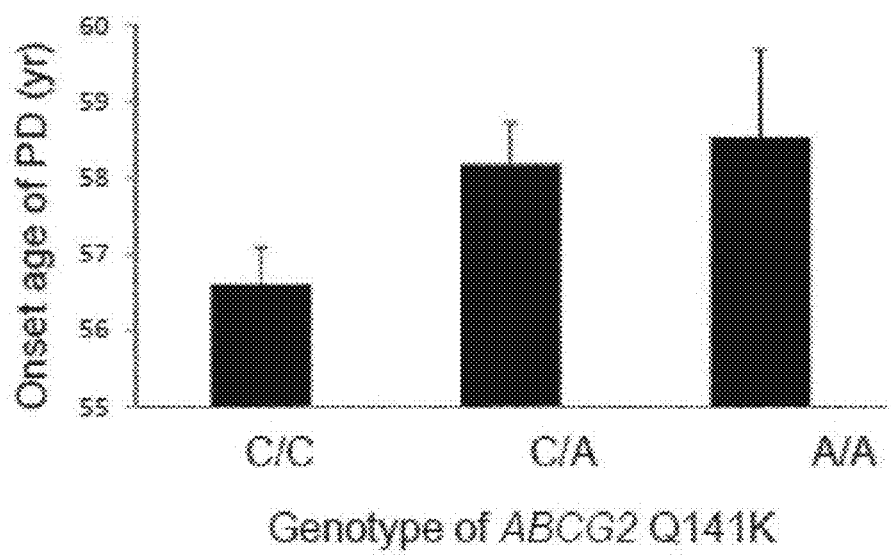
Figure 49:
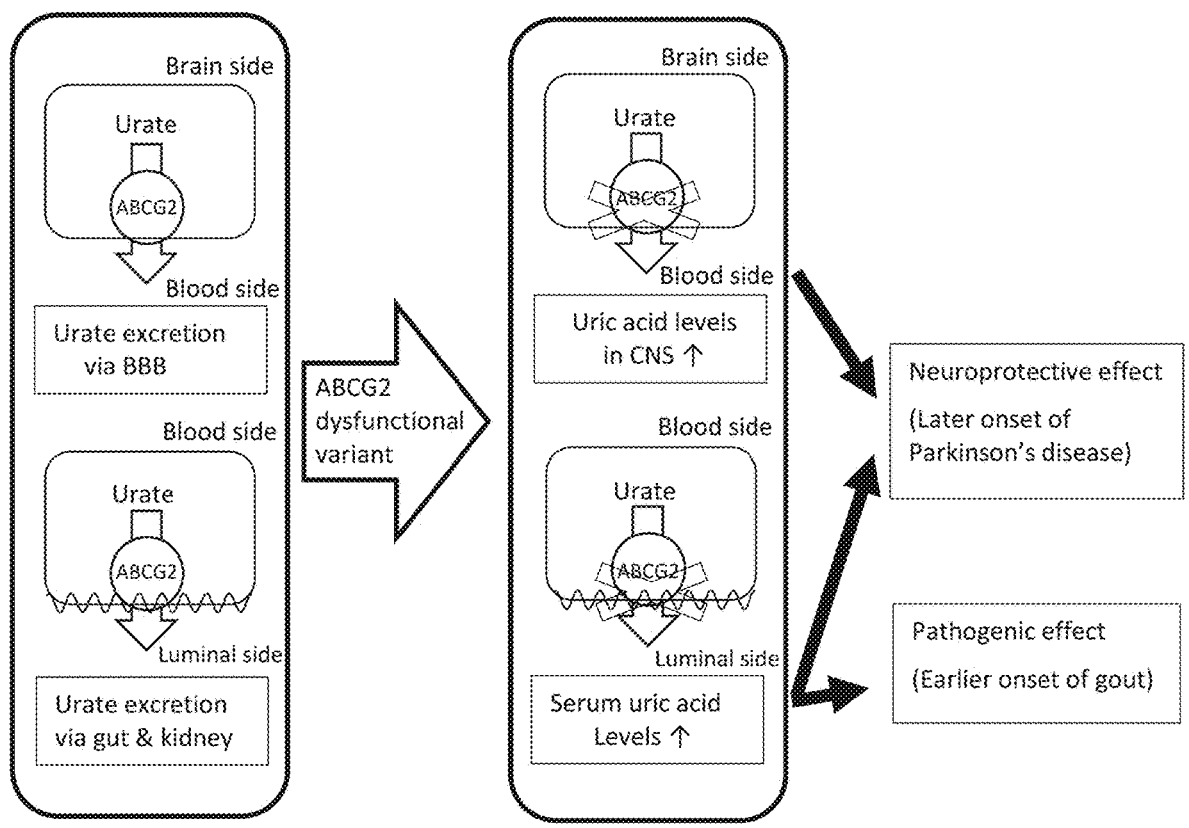
FIG. 49 is an explanatory diagram showing differential effects of ABCG2 dysfunction on gout and Parkinson's disease.

FIGS. 48A and 48B show the results of analysis of the relationship between the function of ABCG2 and the onset age of gout and Parkinson's disease. FIG. 48 (A) is a table showing the results of analysis of the relationship between the onset age of gout and the ABCG2 function. FIG. 48 (B) is a table showing the results of analysis of the relationship between the onset age of Parkinson's disease and the ABCG2 function in patients with Parkinson's disease. FIG. 49 is an explanatory diagram showing different influences of ABCG2 dysfunctions in gout and Parkinson's disease.

When Q141K variation of the ABCG2 gene was examined in 507 male gout cases, a significant association was observed between the onset age of gout and the ABCG2 function. Furthermore, when Q141K variation of the ABCG2 gene was examined in 1015 Parkinson's disease cases as neurodegenerative diseases, a significant-association was observed between the onset age of Parkinson's disease and the ABCG2 function. Parkinson's disease and ABCG2 polymorphism show inverse association, but the uric acid levels needs to be controlled appropriately for prevention of neurodegenerative diseases including Parkinson's disease.

Based on the above-mentioned examples and findings, a molecule associated with the onset of gout of the present invention includes any one protein or cDNA of CNIH2-PACS1, ALDH2, MYL2-CUX2, GCKR, MAP3K11, NPT4, ABCG2, HIST1H2BF/HIST1H4E, HIST1H2BE/HIST1H4D and FAM35A, or a combination thereof with any one protein or cDNA of GLUT9, NPT1, URAT1 and NXRN2, and is capable of relating to the onset of gout; or includes protein or cDNA of an ABCG2 variant, and is capable of selectively and ATP-dependently decreasing excretion of urate.

The present inventors similarly disclose a urate transporter formed of protein having ABCG2 and is capable of selectively and ATP-dependently exporting uric acid as a urate transporter as a molecule associated with the onset of gout, in Patent Literature 5; and also disclose a urate transporter formed of protein including SLC2A9/GLUT9, and is capable of selectively and ATP-dependently exporting uric acid, in Non-Patent Literature 2.

Based on them, any one of CNIH2-PACS1, ALDH2, MYL2-CUX2, GCKR, MAP3K11, NPT4, HIST1H2BF/HIST1H4E, HIST1H2BE/HIST1H4D, and FAM35A may be combined with ABCG2, SLC2A9/GLUT9, GLUT9, NPT1, URAT1, and NXRN2.

A method for evaluating a uric acid-related disease diathesis and an inflammation-related disease diathesis of the present invention includes evaluating whether or not a subject has a diathesis capable of inducing urate regulation failure, or a state or a disease attributable to the failure. The evaluating includes a step of detecting a variation of a gene encoding at least any one protein selected from CNIH2-PACS1, ALDH2, MYL2-CUX2, GCKR, MAP3K11, NPT4, HIST1H2BF/HIST1H4E, HIST1H2BE/HIST1H4D and FAM35A, using a test sample containing human genes of the subject.

For detection of a variation of a gene encoding any one protein of CNIH2-PACS1, ALDH2, MYL2-CUX2, GCKR, MAP3K11, NPT4, HIST1H2BF/HIST1H4E, HIST1H2BE/HIST1H4D, and FAM35A, detection of an SNP or a gene polymorphism having a relationship of linkage disequilibrium with the SNP may be used.

Similar to the above, CNIH2-PACS1, ALDH2, MYL2-CUX2, GCKR, MAP3K11, NPT4, HIST1H2BF/HIST1H4E, HIST1H2BE/HIST1H4D, and FAM35A may be combined with ABCG2, SLC2A9/GLUT9, GLUT9, NPT1, URAT1, and NXRN2.

Note here that CNIH2-PACS1, ALDH2, MYL2-CUX2, GCKR, MAP3K11, NPT4, HIST1H2BF/HIST1H4E, HIST1H2BE/HIST1H4D, and FAM35A, as well as ABCG2, SLC2A9/GLUT9, NPT1, URAT1, and NXRN2 genes include cDNAs derived from human, homogeneous genes derived from human which hybridize with a DNA consisting of a complementary base sequence under a stringent condition and which encode a polypeptide having a urate transport capability, and homologues thereof in mammals.

Examples of the uric acid-related disease and the inflammation-related disease include hyperuricemia, gout, rheumatoid arthritis, osteoarthritis, infertility, cerebral stroke, neurodegenerative disease, ischemic heart disease, chronic kidney disease, renal dysfunction, urolithiasis, kidney stone, aneurysm, arrhythmia including atrial fibrillation, inflammatory bowel disease, enteritis, functional dyspepsia, viral intestinal disease, and photosensitivity.

Furthermore, a higher serum uric acid level is apt to develop uric acid-related diseases and inflammation-related diseases. Accordingly, when the level is equal to or more than a predetermined level such as, for example, 8.0 mg/dl, it may be evaluated that a subject has a high diathesis capable of inducing urate regulation failure or a state or a disease attributable to the failure. The threshold value can be appropriately changed, for example, to 7 or 9.

A method for evaluating a uric acid-related disease diathesis and an inflammation-related disease diathesis of the present invention is a method for evaluating whether or not a subject has a diathesis capable of inducing urate regulation failure, or a state or a disease attributable to the failure. The evaluating includes a step of detecting a variation of a gene encoding ABCG2 protein using a test sample including human genes of the subject. Detection of the variation of the gene is detection of an SNP or a gene polymorphism having a relationship of linkage disequilibrium with the SNP. When a subject has a SNP that generates an amino acid variation of at least any one of R113X, F208S, L447V, S486N, R575X, C608X, P269S, E334X, F489L, and D620G, the method may evaluate that the subject has a diathesis capable of inducing urate regulation failure, or a state or a disease attributable to the failure.

The present inventors disclose, in Patent Literature 5, Q126X, Q141K, G268R, S441N, and F506SfsX as the similar ABCG2 gene variations. In particular, the present inventors disclose the similar method, when Q126X alone or combination of Q126X and Q141K have SNP.

Based on the disclosures, any one of R113X, F208S, L447V, S486N, R575X, C608X, P269S, E334X, F489L, and D620G may be combined with Q126X, Q141K, G268R, S441N, and F506SfsX.

Evaluation can be carried out as follows based on Q126X and Q141K as shown in, for example, FIG. 26.

When a gene encoding Q of Q126X is C/C and a gene encoding Q of Q141K is C/C, the function of ABCG2 is evaluated to be normal; when a gene encoding Q of Q126X is C/C, and a gene encoding Q of Q141K is A/C, the function of ABCG2 is evaluated to be ¾; when a gene encoding Q of Q126X is T/C and a gene encoding Q of Q141K is C/C, the function of ABCG2 is evaluated to be ½; when a gene encoding Q of Q126X is C/C and a gene encoding Q of Q141K is A/A, the function of ABCG2 is evaluated to be ½; when a gene encoding Q of Q126X is T/C and a gene encoding Q of Q141K is A/C, the function of ABCG2 is evaluated to be ¼; and when a gene encoding Q of Q126X is T/T and a gene encoding Q of Q141K is C/C, ABCG2 is evaluated to have no function. The method evaluates that a diathesis capable of inducing urate regulation failure, or a state or a disease attributable to the failure is evaluated to be high depending on a degree of loss of the function of ABCG2. Note here that C/C and the like means "derived from mother side/derived from father side".

The ABCG2 dysfunction includes determining the equivalent degree of BMI reduction, an amount of absolute alcohol intake, age, and sex, which correspond to the effect on the serum uric acid levels, ¼ decrease of the ABCG2 function corresponds to the BMI increase of about 1.97 or about 552 ml per week of absolute alcohol intake. Use of this indicator contributes to not only prevention of onset of diseases such as gout, but also health case by the consciousness about lifestyle habit.

That is to say, it can be evaluated that an effect of ¼ decrease of the ABCG2 function on the serum uric acid levels corresponds to the increase of about 0.193 mg/dl (95% confidence interval: 0.150-0.235 mg/dl), the increase of BMI of 1 kg/m$^2$ corresponds to the increase of the serum uric acid level of about 0.098 mg/dl (95% confidence interval 0.087-0.108 mg/dl), and about 1 g per week of absolute alcohol intake corresponds to the increase of the serum uric acid level of about 0.00035 mg/dl (95% confidence interval 0.00017-0.00053 mg/dl).

Determination of gene polymorphisms can be carried out using human blood or tissues as a material, by a direct sequencing method, a BAC array CGH method, a FISH method, an RFLP method, a PCR-SSCP method, an allele-specific oligonucleotide hybridization method, a TaqMan PCR method, an invader method, an HRM method, a MALDI-TOF/MS method, a molecular beacon method, an RCA method, a UCAN method, a nucleic acid hybridization method using a DNA chip or a DNA microarray, and the like.

SNPs can be detected directly from a genomic DNA by a direct sequencing method and the like.

Also, a particular genomic DNA region may be amplified using a clone, or a PCR method, an LCR method, an SDA method, an RCK method, a LAMP method, an NASBA method and the like, and then, determination of a base sequence of a portion of an allele containing at least a polymorphic site, detection by a probe specifically hybridizing with a polymorphic site, and measurement of a molecular weight of a gene fragment containing a polymorphic site may be performed.

SNPs of an amplified product can be determined by determination of the base sequence, measurement of the molecular weight by a MALDI-TOF mass analysis, and the like, analysis of the restriction enzyme fragment length, detection by SSCP, electrophoresis, and the like.

For example, the TaqMan method is a method in which a hybridization of an allele-specific oligonucleotide with a template is carried out concomitantly with a PCR method, and SNPs are detected using a fluorescence energy transfer phenomenon. When an allele-specific probe labeled with a fluorescent dye and a quencher is hybridized with a target site and PCR is carried out using a primer designed to amplify a region including that site, the hybridized probe is cleaved by a 5' nuclease activity of Taq polymerase, concomitantly with the progress of an extension reaction from the primer. Separation of the fluorescent dye and the quencher yields fluorescence, and amplification of the template by the PCR reaction exponentially enhances a fluorescence intensity. When two allele-specific probes are labeled with different fluorescent dyes, a homozygote and a heterozygote can be distinguished from each other in one assay.

The invader method is a method using two oligonucleotide probes, and is based on an enzyme reaction which recognizes and cleaves a specific structure formed by these probes and a template DNA. A target base sequence is recognized by two different probes, i.e., an invader probe substantially complementary to a first site of the target base sequence, and an allele probe which, on its 3'-terminal side, is substantially complementary to a second site of the target base sequence and which, on its 5'-terminal side, contains a flap not complementary to the template and forming a single strand. When these probes hybridize with adjacent regions of the template, the 3'-terminus of the invader probe invades an SNP site, and the structure is cleaved by an enzyme to release the flap. By labeling the flap in advance, it is possible to quantify the flap released. By preparing two sets of flap-FRET probes and labeling them by different fluorescent dyes, a homozygote and a heterozygote can be distinguished from each other in one assay.

The MALDI-TOF mass analysis is a method in which a primer adjacent to an SNP site is prepared, a primer extension reaction of only one base is carried out using a PCR-amplified test sample DNA as a template and using ddNTP, and the ddNTP added is identified by a mass analysis of extension reaction products. The method does not need any fluorescent label of the primer, and can treat a large number of test samples in a short time.

The RCA method is a method for applying a DNA-amplifying means, in which a DNA polymerase moves on the template and synthesizes a long complementary DNA using a circular single-stranded DNA as a template, to SNP typing. Identification of an SNP is carried out by the presence or absence of amplification via the RCA method. That is to say, a single-stranded probe, which can anneal with a genomic DNA and can become circular, is hybridized with a genomic DNA to carry out the chain reaction. When the terminus of the probe is set to an SNP site to be identified, matching of the site leads to amplification via RCA because of linkage and circularization, but mismatching does not lead to RCA amplification because of no linkage and no circularization. The SNP can be determined by identification of these two amplification reactions.

The DNA chip method is a method for carrying out hybridization with a PCR-amplified, fluorescence-labeled cDNA or cRNA using a DNA chip prepared by arranging oligonucleotide probes containing a polymorphic site on a microarray. The method can detect many SNPs rapidly.

Examples of methods for determining polymorphisms in an amino acid sequence include a proteome analysis by a two-dimensional electrophoresis method or a microfluidics method, peptide mapping and an amino acid sequence analysis using a mass spectroscope, an amino acid sequence analysis by a protein sequencer, a method for detecting the interaction between a polypeptide and a ligand using a protein chip and the like.

For example, the two-dimensional electrophoresis method usually conducts isoelectric point electrophoresis for the first dimension and SDS-PAGE for the second dimension, and can separate several thousand proteins on one plate of gel. For the isoelectric point electrophoresis, an amphoteric carrier or an immobilized pH gradient gel strip is used. For the SDS-PAGE, a continuous buffer solution system using one buffer solution having a certain pH or a discontinuous buffer solution system using multiple buffer solutions having a different pH is used. It is also possible to use a low BIS concentration gel electrophoresis, a concentration gradient gel electrophoresis, tricine-SDS-PAGE and the like, depending on the type of proteins to be separated. The proteins separated can be detected using Coomassie Blue staining or silver staining or using a fluorescent reagent on the gel with high sensitivity. A western blotting method using an antibody against an ABCG2 polypeptide can be also used.

The MALDI-TOF/MS method which is one of mass analysis methods is a method in which a protein test sample is mixed with a matrix absorbing a laser beam such as sinapic acid, the mixture is dried and then irradiated with a high-energy pulse laser beam, the protein test sample is ionized by energy transfer from the matrix, and a molecular weight of the ion is analyzed on the basis of the difference in flight time of a molecular ion of the test sample by an initial acceleration. In order to fragmentize a peptide in the inside of a mass spectrometer and to obtain an amino acid sequence, an amino acid composition or the like by mass analysis of a fragment, a tandem mass spectrometry in which multiple mass separation portions are linked to each other is used. A triple quadrupole type, a hybrid type, or an ion trap type analyzer using an electrospray ionization method, and other analyzers are also used.

The protein chip method can carry out comprehensively and rapidly the interaction of a test sample with proteins, peptides, antibodies, expressed proteins, and the like, which are arranged on a basal plate.

The evaluation kit for a uric acid-related disease diathesis and an inflammation-related disease diathesis according to the present invention is a kit for evaluating whether or not a subject has a diathesis capable of inducing urate regulation failure, or a state or a disease attributable to the failure. The kit has means for detecting at least any one SNP in CNIH2-PACS1, ALDH2, MYL2-CUX2, GCKR, MAP3K11, NPT4, HIST1H2BF/HIST1H4E, HIST1H2BE/HIST1H4D, and FAM35A genes, or a gene polymorphism having a relationship of linkage disequilibrium with the SNP, or a gene polymorphism having a frequency of 1% or less, or a combination thereof with a gene polymorphism including ABCG2, GLUT9, NPT1, URAT1, and NXRN2, using a test sample containing human genes of the subject.

Similar to the above, CNIH2-PACS1, ALDH2, MYL2-CUX2, GCKR, MAP3K11, NPT4, HIST1H2BF/HIST1H4E, HIST1H2BE/HIST1H4D, and FAM35A may be combined with ABCG2, SLC2A9/GLUT9, NPT1, URAT1, and NXRN2.

As the SNPs of CNIH2-PACS1, ALDH2, MYL2-CUX2, GCKR, MAP3K11, NPT4, GLUT9, NPT1, URAT1, NXRN2, HIST1H2BF/HIST1H4E, HIST1H2BE/HIST1H4D, and FAM35A, rs4073582, rs671, rs2188380, rs1260326, rs10791821, rs56027330, rs3775948, rs1165196, rs505802, rs2285340 or rs506338, rs11758351, rs4496782, and rs7903456 can be used, respectively.

As to the ABCG2 gene, means for detecting a SNP of at least any one of R113X, F208S, L447V, S486N, R575X, C608X, P269S, E334X, V178I, N299S, E311K, G462R, V508I, V516M, A634V, F489L, and D620G, or a gene polymorphism having a relationship of linkage disequilibrium with the SNP is provided.

That is to say, a polynucleotide including an ABCG2 gene polymorphism, or a primer pair for amplifying a polynucleotide containing a polymorphism of the ABCG2 gene or a DNA fragment containing a polymorphism, or a polynucleotide for detecting a polymorphism may be provided.

Similar to the above, R113X, F208S, L447V, S486N, R575X, C608X, P269S, E334X, V178I, N299S, E311K, G462R, V508I, V516M, A634V, F489L, and D620G may be combined with V12M, Q126X, Q141K, P269S, S441N, and 506SfsX.

Examples of polynucleotides include both polyribonucleotides and polydeoxyribonucleotides. They may be unmodified RNAs or DNAs, modified RNAs or DNAs, and include, for example, DNAs, cDNAs, genomic DNAs, mRNAs, unprocessed RNAs, their fragments and the like.

Furthermore, polypeptides are those in which two or more amino acids are linked by a peptide bond, and include relatively short chain polypeptides referred to as peptides or oligopeptides, and also long chain polypeptides referred to as proteins. The polypeptides may contain amino acids other than 20 amino acids encoded genetically, and modified amino acids. The modification includes acetylation, acylation, ADP-ribosylation, amidation, biotinylation, a covalent bond with lipids and lipid derivatives, formation of a cross-linking bond, a disulfide bond, addition of a sugar chain, addition of a GPI anchor, phosphorylation, prenylation and the like in a main chain of peptide bonds, a side chain of amino acids, an amino-terminus, and a carboxyl-terminus.

The inspection object of the present invention is a non-human animal having a deficiency or overexpressing of at least any one gene selected from CNIH2-PACS1, ALDH2, MYL2-CUX2, GCKR, MAP3K11, NPT4, HIST1H2BF/HIST1H4E, HIST1H2BE/HIST1H4D, and FAM35A genes, or combination thereof with ABCG2, SLC2A9/GLUT9, NPT1, URAT1, and NXRN2 genes with the above-mentioned gene, and the inspection object may be provided with means for examining the urate transport kinetics.

Nonhuman animals include, for example, mammals such as mouse, and also include tissues and cells constituting their body. Also, test samples are those containing polynucleotides derived from organisms, and include body fluid, skin, hair root, mucosal membrane, internal organs, placenta, cord blood, and the like, collected from tissues and cells.

Similarly, nonhuman animals overexpressing a human ABCG2 gene or a nonhuman ABCG2 gene including at least any one variation (in particular, gene polymorphism) of R113X, F208S, L447V, S486N, R575X, C608X, P269S, E334X, V178I, N299S, E311K, G462R, V508I, V516M, A634V, F489L, and D620G of a human ABCG2 gene or a nonhuman ABCG2 gene; nonhuman cell lines or human cell lines having deficiency of at least any one gene of CNIH2-PACS1, ALDH2, MYL2-CUX2, GCKR, MAP3K11, NPT4, HIST1H2BF/HIST1H4E, HIST1H2BE/HIST1H4D, and FAM35A; nonhuman cell lines or human cell lines overexpressing at least any one gene of human CNIH2-PACS1, ALDH2, MYL2-CUX2, GCKR, MAP3K11, NPT4, HIST1H2BF/HIST1H4E, HIST1H2BE/HIST1H4D, and FAM35A or gene of at least any one gene of nonhuman CNIH2-PACS1, ALDH2, MYL2-CUX2, GCKR, MAP3K11, NPT4, HIST1H2BF/HIST1H4E, HIST1H2BE/HIST1H4D, and FAM35A; nonhuman cell lines or human cell lines overexpression of a human ABCG2 gene or a nonhuman ABCG2 gene including at least any of one variation of R113X, F208S, L447V, S486N, R575X, C608X, P269S, E334X, V178I, N299S, E311K, G462R, V508I, V516M, A634V, F489L, and D620G, or a cell membrane vesicle prepared by such cell lines may be used.

Similar to the above, R113X, F208S, L447V, S486N, R575X, C608X, P269S, E334X, V178I, N299S, E311K, G462R, V508I, V516M, A634V, F489L, and D620G may be combined with V12M, Q126X, Q141K, G268R, S441N, and F506SfsX.

Drugs for uric acid-related diseases and the drug for inflammation-related diseases are drugs for reducing a diathesis capable of inducing urate regulation failure, or a state or a disease attributable to the failure, and contains a polynucleotide encoding at least any one protein of CNIH2-PACS1, ALDH2, MYL2-CUX2, GCKR, MAP3K11, NPT4, HIST1H2BF/HIST1H4E, HIST1H2BE/HIST1H4D, and FAM35A in the form capable of introducing it into cells or a polypeptide corresponding to at least any one protein of CNIH2-PACS1, ALDH2, MYL2-CUX2, GCKR, MAP3K11, NPT4, HIST1H2BF/HIST1H4E, HIST1H2BE/HIST1H4D, and FAM35A in the form capable of introducing it into cells. The former drug can stably improve the urate transport for a long period, and the latter drug can easily improve the urate transport by administration via injection and the like.

Similar to the above mention, CNIH2-PACS1, ALDH2, MYL2-CUX2, GCKR, MAP3K11, NPT4, HIST1H2BF/HIST1H4E, HIST1H2BE/HIST1H4D, and FAM35A may be combined with ABCG2, SLC2A9/GLUT9, NPT1, URAT1, and NXRN2.

Note here that the form capable of introducing a polynucleotide into cells means a form allowing introduction of polynucleotide into cells and expression of any of CNIH2-PACS1, ALDH2, MYL2-CUX2, GCKR, MAP3K11, NPT4, HIST1H2BF/HIST1H4E, HIST1H2BE/HIST1H4D, and FAM35A encoded so that any of intracellular CNIH2-PACS1, ALDH2, MYL2-CUX2, GCKR, MAP3K11, NPT4, HIST1H2BF/HIST1H4E, HIST1H2BE/HIST1H4D, and FAM35A genes express at least any of CNIH2-PACS1, ALDH2, MYL2-CUX2, GCKR, MAP3K11, NPT4, HIST1H2BF/HIST1H4E, HIST1H2BE/HIST1H4D, and FAM35A, respectively. Similarly, the form capable of introducing a polypeptide into cells means a form allowing introduction of the polypeptide into cells and exertion of a function similar to that of at least any of intracellular CNIH2-PACS1, ALDH2, MYL2-CUX2, GCKR, MAP3K11, NPT4, HIST1H2BF/HIST1H4E, HIST1H2BE/HIST1H4D, and FAM35A.

CNIH2-PACS1, ALDH2, MYL2-CUX2, GCKR, MAP3K11, NPT4, HIST1H2BF/HIST1H4E, HIST1H2BE/HIST1H4D, and FAM35A polynucleotides can be obtained by a method of screening an existing cDNA library using an oligonucleotide probe prepared on the basis of a known nucleotide sequence, or a method such as RT-PCR using an oligonucleotide primer.

ABCG2 not having any SNP in R113X, F208S, L447V, S486N, R575X, C608X, P269S, E334X, V178I, N299S, E311K, G462R, V508I, V516M, A634V, F489L, and D620G, and ABCG2 not having at least an SNP in Q126X are preferred. In order to obtain a form capable of introducing the ABCG2 polynucleotide into cells, for example, a method using the polynucleotide as a bare DNA, or a method formulating the polynucleotide in a form of a recombinant virus vector is used. Virus vectors include those derived from genomes of viruses belonging to Baculoviridae, Parvoviridae, Picornoviridae, Herpesviridae, Poxyiridae, Adenoviridae, Picornaviridae and the like.

Note here that as mentioned above, R113X, F208S, L447V, S486N, R575X, C608X, P269S, E334X, V178I, N299S, E311K, G462R, V508I, V516M, A634V, F489L, and D620G may be combined with V12M, Q126X, Q141K, G268R, S441N, and F506SfsX.

Also, a polynucleotide expression vector may be introduced into tissues or cells removed from a living body, and then, the tissues or cells may be returned to the living body. In such a case, a method can be used in which an expression vector integrating a polynucleotide is introduced into cells by transfection such as, for example, a microinjection method or an electroporation method.

The polynucleotide in a virus vector or an expression vector may be linked under a control of a promoter inducing systemic or tissue-specific expression. When a virus vector is infected in a kidney-specific manner, it is possible to introduce a recombinant vector by percutaneously inserting a catheter into an artery and then inserting the catheter into a renal artery while checking the location of the catheter by X-rays.

A polypeptide such as ABCG2 can be produced by a genetic engineering technique using the above-mentioned polynucleotide such as ABCG2. That is to say, the polypeptide such as ABCG2 can be obtained in vitro by preparing an RNA by an in vitro transcription from a vector containing the polynucleotide, and carrying out an in vitro translation using it as a template. When the polynucleotide is recombined into an expression vector, it is also possible to obtain the polypeptide such as ABCG2 as an expression product from prokaryotic cells such as *Escherichia coli* or *Bacillus subtilis*, from yeast, or from eukaryotic cells such as insect cells or mammal cells.

Also, the polypeptide such as ABCG2 can be synthesized according to a known chemical synthesis method.

The polypeptide such as ABCG2 may be provided as a peptide derivative. Such a derivative contains a modification for accelerating synthesis and purification, a modification for accelerating physical and chemical stabilization, an activation modification such as stabilization and instabilization or conditioning for in vivo metabolism, and the like.

Other modifications in peptide derivatives include acetylation, acylation, ADP-ribosylation, amidation, a covalent bond of flavin, a covalent bond of a heme moiety, a covalent bond of nucleotides or nucleotide derivatives, a covalent bond of lipids or lipid derivatives, a covalent bond of phosphatidylinositol, cross-linking, cyclization, a disulfide bond, demethylation, formation of a cross-linking covalent bond, cystine formation, pyroglutamate formation, formylation, gamma-carboxylation, glycosylation, GPI-anchor formation, hydroxylation, iodination, methylation, myristoylation, oxidation, proteolytic processing, phosphorylation, prenylation, racemization, a lipid bond, sulfation, selenoylation and the like.

Specifically, the peptide derivatives can be prepared in the form of a functional group produced as a side chain or as an N-terminal group or a C-terminal group, in the range not destroying any activity of a polypeptide such as ABCG2 and not giving any toxicity to a composition containing the polypeptide. Examples thereof include derivatives containing a polyethylene glycol side chain which extends retainment of a polypeptide in the body fluid, aliphatic esters of a carboxyl group, amides of a carboxyl group by a reaction with ammonia or an amine, N-acyl derivatives of a free amino group on an amino acid residue formed with an acyl moiety, O-acyl derivatives of a free hydroxyl group formed with an acyl moiety and the like.

The polypeptide such as ABCG2 also may be provided in the form of a pharmaceutically acceptable salt. Such a salt includes both a salt of a carboxyl group and an acid addition salt of an amino group on the polypeptide.

Examples of salts of a carboxyl group include inorganic salts such as a sodium, calcium, ammonium, iron, or zinc salt, as well as salts with an organic base formed using an amine such as triethanolamine, arginine, lysine, piperidine, and procaine. Examples of salts of acid addition salts include salts with a mineral acid such as hydrochloric acid or sulfuric acid, as well as salts with an organic acid such as acetic acid or oxalic acid.

In order to formulate a polypeptide such as ABCG2 in the form capable of introducing it into cells, for example, a fused polypeptide in which a transmembrane peptide is linked to an N-terminal side of the polypeptide is used. As the transmembrane peptide, PTD of HIV-1 TAT or PTD of drosophila homeobox protein Antennapedia can be used. The fused polypeptide can be prepared by a genetic engineering technique, for example, using a fused polynucleotide prepared by linking a polynucleotide such as ABCG2 and a PTD polynucleotide. It is also possible to prepare a fused polypeptide linked with a transmembrane peptide by a method for linking a polypeptide and a PTD peptide through a cross-linking agent such as EDC or β-alanine. Such a fused polypeptide can be introduced by percutaneously inserting a catheter into an artery and then inserting the catheter into a renal artery while checking the location of the catheter by X-rays to introduce a recombinant vector.

INDUSTRIAL APPLICABILITY

The present invention effectively evaluates whether or not a subject has a diathesis capable of inducing urate regulation failure, or a state or a uric acid-related disease and an inflammation-related disease attributable to the failure, and therefore contributes to prevention and early treatment of various diseases related to abnormality in the uric acid levels, or uric acid-related genes or gout-related genes. Furthermore, the present invention contributes to treatment of uric acid-related diseases without causing other undesirable effects even after the onset. Accordingly, the present invention is effective to inflammation-related diseases such as hyperuricemia, gout, rheumatoid arthritis, osteoarthritis, infertility, cerebral stroke, neurodegenerative disease, ischemic heart disease, chronic kidney disease, renal dysfunction, urolithiasis, kidney stone, aneurysm, arrhythmia including atrial fibrillation, inflammatory bowel disease, enteritis, functional dyspepsia, viral intestinal disease, and photosensitivity, and also effective to hypertension, obesity, diabetes, a coronary artery disease, a cerebrovascular disease, a kidney disease and the like which are likely to develop as a result of complications. Furthermore, it is also possible to avoid useless medication and to present indicators for lifestyle habit for health care, and therefore the present invention is industrially useful.

We claim:

1. A method for preventing an onset of gout in a human subject, the method comprising:
   obtaining a test sample from the subject, the test sample containing nucleic acids from the subject;
   detecting in the test sample the presence of:
   (i) rs7903456 of FAM35A allele C; and
   (ii) rs2231142 of ABCG2 allele A;
   and administering to the subject a drug for uric acid related disease and inflammation related disease suitable to prevent the onset of the gout.

2. The method of claim 1, further comprising administering FAM35A to the subject.

* * * * *